US008394384B2

(12) United States Patent
Guo et al.

(10) Patent No.: US 8,394,384 B2

(45) Date of Patent: Mar. 12, 2013

(54) RECOMBINANT AVIAN INFLUENZA VACCINE AND USES THEREOF

(75) Inventors: Xuan Guo, Suwanee, GA (US); Michel Bublot, Chaponost (FR); Joyce A. Pritchard, Gainesville, GA (US); Lynn F. Dickey, Cary, NC (US)

(73) Assignees: Merial Limited, Duluth, GA (US); Biolex Therapeutics, Inc., Pittsboro, NC (US)

( * ) Notice: Subject to any disclaimer, the term of this patent is extended or adjusted under 35 U.S.C. 154(b) by 468 days.

(21) Appl. No.: 12/628,085

(22) Filed: Nov. 30, 2009

(65) Prior Publication Data

US 2010/0189731 A1 Jul. 29, 2010

Related U.S. Application Data

(60) Provisional application No. 61/118,492, filed on Nov. 28, 2008.

(51) Int. Cl.

| | |
|---|---|
| ***A61K 39/00*** | (2006.01) |
| ***A61K 39/38*** | (2006.01) |
| ***A61K 39/12*** | (2006.01) |
| ***A61K 39/14*** | (2006.01) |
| ***A61K 38/00*** | (2006.01) |
| ***A61K 48/00*** | (2006.01) |
| ***C12Q 1/00*** | (2006.01) |
| ***C12Q 1/70*** | (2006.01) |

(52) U.S. Cl. ............... 424/210.1; 424/184.1; 424/185.1; 424/204.1; 424/209.1; 435/4; 435/5; 514/1.1; 514/44 R

(58) Field of Classification Search ........................ None
See application file for complete search history.

(56) References Cited

U.S. PATENT DOCUMENTS

| | | | | |
|---|---|---|---|---|
| 3,531,565 | A * | 9/1970 | Cabasso et al. ............ | 424/239.1 |
| 6,040,498 | A | 3/2000 | Stomp et al. | |
| 6,815,184 | B2 | 11/2004 | Stomp et al. | |
| 7,022,309 | B2 | 4/2006 | Hiatt et al. | |
| 7,160,717 | B2 | 1/2007 | Everett | |
| 7,161,064 | B2 | 1/2007 | Stomp et al. | |
| 7,176,024 | B2 | 2/2007 | Branson et al. | |
| 2007/0286873 | A1 | 12/2007 | Williams et al. | |
| 2008/0107681 | A1 | 5/2008 | Karaca et al. | |

OTHER PUBLICATIONS

Treanor et al. Safety and Immunogenicity of an Inactivated Subvirion Influenza A (H5N1) Vaccine. The New England Journa of Medicine, Mar. 30, 2006, vol. 354, No. 13, pp. 1343-1351.*

Twyman, R. M. (2005) Host Plants, Systems and Expression Strategies for Molecular Farming, in Molecular Farming: Plant-Made Pharmaceuticals and Technical Proteins (eds R. Fischer and S. Schillberg), Wiley-VCH Verlag GmbH & Co. KGaA, Weinheim, FRG.*

Gasdaska et al. Advantages of Therapeutic Protein Production in the Aquatic Plant Lemna. BioProcessing Journal, Mar./Apr. 2003, vol. 2, pp. 49-56.*

De Jong et al.; Avian Influenza; J Clin Virol. Jan. 2006; 35 (1):2-13.

Olsen et al.; Global Patterns of Influenza A Virus in Wild Birds; Science. Apr. 21, 2006; 312(5772):384-8.

Chargelegue et al.; Transgenic Plants for Vaccine Production: Expectations and Limitations; Trends in Plant Science 2001, 6, 495-496.

Schillberg et al.; Opportunities for Recombinant Antigen and Antibody Expression in Transgenic Plants—Technology Assessment; Vaccine 2005, 23, 1764-1769.

Arntzen et al.; Plant-derived Vaccines and Antibodies: Potential and Limitations; Vaccine 2005, 23, 1753-1756.

Schulze et al.; Effect of Glycosylation on the Properties and Functions of Influenza Virus Hemagglutinin; J Infect Dis, 1997. 176 Suppl 1: p. S24-8.

Deshpande et al.; Glycosylation Affects Cleavage of an H5N2 Influenza Virus Hemagglutinin and Regulates Virulence; PNAS USA, 1987, 84(1) : p. 36-40.

Edelman, "An Update on Vaccine Adjuvants in Clinical Trial," Aids Research and Human Retroviruses 8(8): 1409-1411 (1992).

McElrath, "Selection of potent immunological adjuvants for vaccine construction," seminars in Cancer Biology 6:375-385 (1995).

Aucouturier et al., "Adjuvants designed for veterinary and human vaccines," Vaccine 19:2666-2672 (2001).

East et al., "Adjuvants for New Veterinary Vaccines," Chapter 1 in Progress in Vaccinology, vol. 4 Veterinary Vaccines, Springer Verlag, NY 1993, pp. 1-28.

Altman et al., "Immunomodifiers in Vaccines," Advances in Veterinary Science and Comparative Medicine 33:301-343 (1989).

Wilson et al., "Tissue Reaction and Immunity in Swine Immunized with *Actinobacillus pleuropneumoniae* Vaccines," Can J Vet Res 59:299-305 (1995).

Faye et al., "Protein modification in the plant secretory pathway: current status and practical implications in molecular pharming", Vaccine 23:1770-1778, 2005.

"Therapeutic Monoclonal Antibodies: From Bench to Clinic", 2009 John Wiley & Sons, Inc., Chapter 29 "Production of Antibodies in Plants" by Cox et al.

EMBL accession No. EF473080, Mar. 17, 2007, "influenza A virus (A/chicken/Indonesia/7/2003(H5N1)) segment 4 hegagglutinin (HA) gene, complete eds."

World HLTH Org Global Inluenza PR: "Evolution of H5N1 avian influenza viruses in Asia", Emerging Infectious Diseases, vol. 11, No. 10, p. 1515-1521, Oct. 2005.

Dugan Vivien, et al., "The evolutionary genetics and emergence of avian influenza viruses in wild birds", Plos Pathogens, vol. 4, No. 5, PE1000076, May 2008.

*Primary Examiner* — Louise Humphrey

(74) *Attorney, Agent, or Firm* — Judy Jarecki-Black; Ruoying Chen; Merial Limited

(57) ABSTRACT

The present invention encompasses influenza vaccines, in particular avian influenza vaccines. The vaccine may be a subunit vaccine based on the hemagglutinin of influenza. The hemagglutinin may be expressed in plants including duckweed. The invention also encompasses recombinant vectors encoding and expressing influenza antigens, epitopes or immunogens which can be used to protect animals against influenza. It encompasses also a vaccination regimen compatible with the DIVA strategy, including a prime-boost scheme using vector and subunit vaccines.

26 Claims, 35 Drawing Sheets

Figure 1

| SEQ ID NO | Type | Gene Name |
|---|---|---|
| 1 | DNA | Synthetic (codon-optimized) H5N1 gene |
| 2 | Protein | Protein translated from SEQ ID NO:1. mature HA peptide fragment without signal peptide. |
| 3 | DNA | H5N1 (A/chicken/Indonesia/7/2003) wild type DNA |
| 4 | Protein | Avian Influenza H5N1 ck/Indonesia/03 (mutated). The sequence contains mutated sequence of basic amino acids at HA fusion cleavage site |
| 5 | Protein | A/chicken/Indonesia/7/2003(H5N1) wild type protein |
| 6 | DNA | MerB01 vector sequence |
| 7 | DNA | EU723707, DNA of HA gene from A/whooper swan/Mongolia/244/2005(H5) |
| 8 | Protein | ACD68156, protein of HA gene from A/whooper swan/Mongolia/244/2005(H5) |
| 9 | DNA | EU124148, DNA of HA gene from A/Chicken/West Java/PWT-WIJ/2006(H5N1) |
| 10 | Protein | ABU99080, protein of HA gene from A/Chicken/West Java/PWT-WIJ/2006(H5N1) |
| 11 | DNA | CY015089, DNA of HA gene from A/turkey/Ireland/1378/1983(H5N8) |
| 12 | Protein | ABI85117, protein of HA gene from A/turkey/Ireland/1378/1983(H5N8) |
| 13 | DNA | EU122404, DNA of HA gene from A/Viet Nam/1203/2004(H5N1) |
| 14 | Protein | ABW90135, protein of HA gene from A/Viet Nam/1203/2004(H5N1) |
| 15 | DNA | M24286, Alpha amylase signal sequence |
| 16 | Protein | AAA33885, Alpha amylase signal peptide sequence |
| 17 | Protein | Multiple basic amino acid region of HA gene |
| 18 | Protein | Mutated HA cleavage region sequence |

Figure 2

Synthetic (Codon-optimized) H5N1 [A/chicken/Indonesia/7/2003) hemagglutinin (HA) DNA sequence (corresponding to the HA open reading frame after the signal cleavage site up to the stop codon (not included)] (SEQ ID NO:1)

```
   1 gaccagatct gcatcggcta ccacgccaac aattccaccg agcaggtgga cacgatcatg
  61 gaaaagaacg tgaccgtcac ccacgcccag gacatcctcg agaagacgca caacgggaag
 121 ctctgcgacc tcgacggcgt gaagccgctc atcctccgcg actgctccgt ggccggctgg
 181 ctcctgggca accccatgtg cgacgagttc atcaacgtcc cggagtggtc ctacatcgtg
 241 gagaaggcca accccgccaa cgatctgtgc tacccgggga acctcaacga ctacgaggaa
 301 ctcaagcacc tgctctcccg catcaaccac ttcgagaaga tccagatcat cccgaagtcc
 361 agctggtccg accacgaggc gtccagcggc gtcagctccg cctgcccgta ccaaggcaag
 421 tccagcttct tccggaacgt cgtgtggctg atcaagaaga actcggccta ccccaccatc
 481 aagaggagct acaacaatac gaaccaggag gacctgctcg tgctgtgggg gatccaccac
 541 ccgaacgacg cggccgagca gacccgcctg taccagaacc ccaccacgta catctccgtc
 601 gggaccagca cgctcaacca gcgcctggtg ccgaagatcg ccatccgcag caaggtgaac
 661 gggcagtcgg gtcgcatgga gttcttctgg acgatcctga agcccaacga cgccatcaac
 721 ttcgagagca acggcaactt catcgccccg gagtacgcgt acaagatcgt caagaagggg
 781 gacagcgcca tcatgaagtc ggagctggag tacgggaact gtaacacgaa gtgccagacc
 841 cccatgggcg cgatcaactc cagcatgccc ttccacaaca tccacccgct caccatcggc
 901 gagtgcccca agtacgtcaa gagcaacagg ctggtcctgg ccacgggcct ccgcaacagc
 961 ccccagcggg agacccgcgg gctcttcggg gccatcgcgg ggttcatcga gggcgggtgg
1021 cagggcatgg tggacggttg gtacggctac caccacagca acgagcaggg ctcgggctac
1081 gccgcggaca aggagtccac ccagaaggcc atcgacggcg tgaccaacaa ggtgaactcc
1141 atcatcgaca agatgaacac ccagttcgag gccgtcgggc gcgagttcaa caacctggag
1201 cgccggatcg agaacctcaa caagaagatg gaggacgggt tcctggacgt gtggacctac
1261 aacgcggagc tgctcgtgct catggagaac gagaggacgc tcgacttcca cgactccaac
1321 gtcaagaacc tgtacgacaa ggtccggctg cagctccggg acaacgccaa ggagctgggc
1381 aacggctgct tcgagttcta ccacaagtgc gacaacgagt gcatggagtc catcaggaac
1441 ggcacgtaca actacccca gtattccgag gaggctcgcc tcaagaggga ggagatcagc
1501 ggcgtcaagc tcgagtccat cgggacctac cagatcctct ccatctactc cacggtggcg
1561 tccagcctcg ccctcgccat catgatggct ggcctgtcgc tgtggatgtg ctccaacggg
1621 agcctccagt gccgcatctg catc
```

Figure 3

H5N1 (A/chicken/Indonesia/7/2003) hemagglutinin (HA) amino acid sequence translated from the codon-optimized and mutated H5N1 HA gene after cleavage of the signal sequence
(SEQ ID NO:2)

```
  1 DQICIGYHAN NSTEQVDTIM EKNVTVTHAQ DILEKTHNGK LCDLDGVKPL ILRDCSVAGW
 61 LLGNPMCDEF INVPEWSYIV EKANPANDLC YPGNLNDYEE LKHLLSRINH FEKIQIIPKS
121 SWSDHEASSG VSSACPYQGK SSFFRNVVWL IKKNSAYPTI KRSYNNTNQE DLLVLWGIHH
181 PNDAAEQTRL YQNPTTYISV GTSTLNQRLV PKIAIRSKVN GQSGRMEFFW TILKPNDAIN
241 FESNGNFIAP EYAYKIVKKG DSAIMKSELE YGNCNTKCQT PMGAINSSMP FHNIHPLTIG
301 ECPKYVKSNR LVLATGLRNS PQRETRGLFG AIAGFIEGGW QGMVDGWYGY HHSNEQGSGY
361 AADKESTQKA IDGVTNKVNS IIDKMNTQFE AVGREFNNLE RRIENLNKKM EDGFLDVWTY
421 NAELLVLMEN ERTLDFHDSN VKNLYDKVRL QLRDNAKELG NGCFEFYHKC DNECMESIRN
481 GTYNYPQYSE EARLKREEIS GVKLESIGTY QILSIYSTVA SSLALAIMMA GLSLWMCSNG
541 SLQCRICI
```

Full length H5N1 (A/chicken/Indonesia/7/2003) hemagglutinin (HA) amino acid sequence translated from the codon-optimized and mutated H5N1 HA gene
(SEQ ID NO:4)

```
  1 MEKIVLLLAI VSLVKSDQIC IGYHANNSTE QVDTIMEKNV TVTHAQDILE KTHNGKLCDL
 61 DGVKPLILRD CSVAGWLLGN PMCDEFINVP EWSYIVEKAN PANDLCYPGN LNDYEELKHL
121 LSRINHFEKI QIIPKSSWSD HEASSGVSSA CPYQGKSSFF RNVVWLIKKN SAYPTIKRSY
181 NNTNQEDLLV LWGIHHPNDA AEQTRLYQNP TTYISVGTST LNQRLVPKIA IRSKVNGQSG
241 RMEFFWTILK PNDAINFESN GNFIAPEYAY KIVKKGDSAI MKSELEYGNC NTKCQTPMGA
301 INSSMPFHNI HPLTIGECPK YVKSNRLVLA TGLRNSPQRE TRGLFGAIAG FIEGGWQGMV
361 DGWYGYHHSN EQGSGYAADK ESTQKAIDGV TNKVNSIIDK MNTQFEAVGR EFNNLERRIE
421 NLNKKMEDGF LDVWTYNAEL LVLMENERTL DFHDSNVKNL YDKVRLQLRD NAKELGNGCF
481 EFYHKCDNEC MESIRNGTYN YPQYSEEARL KREEISGVKL ESIGTYQILS IYSTVASSLA
541 LAIMMAGLSL WMCSNGSLQC RICI*
```

A/chicken/Indonesia/7/2003(H5N1) wild type HA protein
(SEQ ID NO:5)

```
  1 mekivlllai vslvksdqic igyhannste qvdtimeknv tvthaqdile kthngklcdl
 61 dgvkplilrd csvagwllgn pmcdefinvp ewsyivekan pandlcypgn lndyeelkhl
121 lsrinhfeki qiipksswsd heassgvssa cpyqgkssff rnvvwlikkn sayptikrsy
181 nntnqedllv lwgihhpnda aeqtrlyqnp ttyisvgtst lnqrlvpkia irskvngqsg
241 rmeffwtilk pndainfesn gnfiapeyay kivkkgdsai mkseleygnc ntkcqtpmga
301 inssmpfhni hpltigecpk yvksnrlvla tglrnspqre rrrkkrglfg aiagfieggw
361 qgmvdgwygy hhsneqgsgy aadkestqka idgvtnkvns iidkmntqfe avgrefnnle
421 rrienlnkkm edgfldvwty naellvlmen ertldfhdsn vknlydkvrl qlrdnakelg
481 ngcfefyhkc dnecmesirn gtynypqyse earlkreeis gvklesigty qilsiystva
541 sslalaimma glslwmcsng slqcrici
```

Figure 4

A/chicken/Indonesia/7/2003(H5N1) wild type (native) HA cDNA sequence
(GenBank Accession No. EF473080) (SEQ ID NO:3)

```
   1 atggagaaaa tagtgcttct tcttgcaata gtcagtcttg ttaaaagtga tcagatttgc
  61 attggttacc atgcaaacaa ttcaacagag caggttgaca caataatgga aaagaacgtt
 121 actgttacac atgcccaaga catactggaa aagacacaca acgggaagct ctgcgatcta
 181 gatggagtga agcctctaat tttaagagat tgtagtgtag ctggatggct cctcgggaat
 241 ccaatgtgtg acgaattcat caatgtaccg gaatggtctt acatagtgga gaaggccaat
 301 ccagccaatg acctctgtta cccagggaat ctcaacgact atgaagaact aaaacaccta
 361 ttgagcagaa taaaccattt tgagaaaatt cagatcatcc ccaaaagttc ttggtccgat
 421 catgaagcct catcaggggt gagctcagca tgtccatacc agggaaagtc ctcctttttt
 481 agaaatgtgg tatggcttat caaaaagaac agtgcatacc caacaataaa gagaagctac
 541 aataatacca accaagaaga tcttttggta ctgtggggga ttcaccatcc taatgatgcg
 601 gcagagcaga caaggctata tcaaaaccca accacctata tttccgttgg gacatcaaca
 661 ctaaaccaga gattggtacc aaaaatagct attagatcca aagtaaacgg gcaaagtgga
 721 agaatggagt tcttctggac aattttaaaa ccgaatgatg caatcaactt cgagagtaat
 781 ggaaatttca ttgctccaga atatgcatac aaaattgtca agaaagggga ctctgcaatt
 841 atgaaaagtg aattggaata tggtaactgc aacaccaagt gtcaaactcc aatgggggcg
 901 ataaactcta gtatgccatt ccacaacata caccctctca ccatcgggga atgccccaaa
 961 tatgtgaaat caaacagatt agtccttgcg actgggctca gaaatagccc tcaaagagag
1021 agaagaagaa aaaagagagg actatttgga gctatagcag gttttataga gggaggatgg
1081 cagggaatgg tagatggttg gtatgggtac caccatagca atgagcaggg gagtgggtac
1141 gctgcagaca aagaatccac tcaaaaggca atagatgggg tcaccaataa ggtcaactcg
1201 atcattgaca aaatgaacac tcagtttgag gccgttggaa gggaatttaa taacttagaa
1261 aggagaatag agaatttaaa caagaagatg gaagacggat tcctagatgt ctggacttat
1321 aatgctgaac ttctggttct catggaaaat gagagaactc tagactttca tgactcaaat
1381 gttaagaacc tctacgacaa ggtccgacta cagcttaggg ataatgcaaa ggagctgggt
1441 aacggttgtt tcgagttcta tcacaaatgt gataatgaat gtatggaaag tataagaaac
1501 ggaacgtata actacccgca gtattcagaa gaagcaagat taaaaagaga agaaataagt
1561 ggagtaaaat tggaatcaat aggaacttac caaatactgt caatttattc aacagtggcg
1621 agttccctag cactggcaat catgatggct ggtctatctt tatggatgtg ctccaatgga
1681 tcgttacaat gcagaatttg catttaa
```

Figure 5 (1/5)

```
                          1                                      40
SEQ ID NO:2         (1)   ----------------DQICIGYHANNSTEQVDTIMEKNV
SEQ ID NO:4         (1)   MEKIVLLLAIVSLVKSDQICIGYHANNSTEQVDTIMEKNV
SEQ ID NO:5         (1)   MEKIVLLLAIVSLVKSDQICIGYHANNSTEQVDTIMEKNV
                          41                                     80
SEQ ID NO:2        (25)   TVTHAQDILEKTHNGKLCDLDGVKPLILRDCSVAGWLLGN
SEQ ID NO:4        (41)   TVTHAQDILEKTHNGKLCDLDGVKPLILRDCSVAGWLLGN
SEQ ID NO:5        (41)   TVTHAQDILEKTHNGKLCDLDGVKPLILRDCSVAGWLLGN
                          81                                    120
SEQ ID NO:2        (65)   PMCDEFINVPEWSYIVEKANPANDLCYPGNLNDYEELKHL
SEQ ID NO:4        (81)   PMCDEFINVPEWSYIVEKANPANDLCYPGNLNDYEELKHL
SEQ ID NO:5        (81)   PMCDEFINVPEWSYIVEKANPANDLCYPGNLNDYEELKHL
                          121                                   160
SEQ ID NO:2       (105)   LSRINHFEKIQIIPKSSWSDHEASSGVSSACPYQGKSSFF
SEQ ID NO:4       (121)   LSRINHFEKIQIIPKSSWSDHEASSGVSSACPYQGKSSFF
SEQ ID NO:5       (121)   LSRINHFEKIQIIPKSSWSDHEASSGVSSACPYQGKSSFF
                          161                                   200
SEQ ID NO:2       (145)   RNVVWLIKKNSAYPTIKRSYNNTNQEDLLVLWGIHHPNDA
SEQ ID NO:4       (161)   RNVVWLIKKNSAYPTIKRSYNNTNQEDLLVLWGIHHPNDA
SEQ ID NO:5       (161)   RNVVWLIKKNSAYPTIKRSYNNTNQEDLLVLWGIHHPNDA
                          201                                   240
SEQ ID NO:2       (185)   AEQTRLYQNPTTYISVGTSTLNQRLVPKIAIRSKVNGQSG
SEQ ID NO:4       (201)   AEQTRLYQNPTTYISVGTSTLNQRLVPKIAIRSKVNGQSG
SEQ ID NO:5       (201)   AEQTRLYQNPTTYISVGTSTLNQRLVPKIAIRSKVNGQSG
                          241                                   280
SEQ ID NO:2       (225)   RMEFFWTILKPNDAINFESNGNFIAPEYAYKIVKKGDSAI
SEQ ID NO:4       (241)   RMEFFWTILKPNDAINFESNGNFIAPEYAYKIVKKGDSAI
SEQ ID NO:5       (241)   RMEFFWTILKPNDAINFESNGNFIAPEYAYKIVKKGDSAI
                          281                                   320
SEQ ID NO:2       (265)   MKSELEYGNCNTKCQTPMGAINSSMPFHNIHPLTIGECPK
SEQ ID NO:4       (281)   MKSELEYGNCNTKCQTPMGAINSSMPFHNIHPLTIGECPK
SEQ ID NO:5       (281)   MKSELEYGNCNTKCQTPMGAINSSMPFHNIHPLTIGECPK
                          321                                   360
SEQ ID NO:2       (305)   YVKSNRLVLATGLRNSPQRE----TRGLFGAIAGFIEGGW
SEQ ID NO:4       (321)   YVKSNRLVLATGLRNSPQRE----TRGLFGAIAGFIEGGW
SEQ ID NO:5       (321)   YVKSNRLVLATGLRNSPQRERRRKKRGLFGAIAGFIEGGW
                          361                                   400
SEQ ID NO:2       (341)   QGMVDGWYGYHHSNEQGSGYAADKESTQKAIDGVTNKVNS
SEQ ID NO:4       (357)   QGMVDGWYGYHHSNEQGSGYAADKESTQKAIDGVTNKVNS
SEQ ID NO:5       (361)   QGMVDGWYGYHHSNEQGSGYAADKESTQKAIDGVTNKVNS
                          401                                   440
SEQ ID NO:2       (381)   IIDKMNTQFEAVGREFNNLERRIENLNKKMEDGFLDVWTY
SEQ ID NO:4       (397)   IIDKMNTQFEAVGREFNNLERRIENLNKKMEDGFLDVWTY
SEQ ID NO:5       (401)   IIDKMNTQFEAVGREFNNLERRIENLNKKMEDGFLDVWTY
                          441                                   480
```

Figure 5 (2/5)

```
SEQ ID NO:2  (421) NAELLVLMENERTLDFHDSNVKNLYDKVRLQLRDNAKELG
SEQ ID NO:4  (437) NAELLVLMENERTLDFHDSNVKNLYDKVRLQLRDNAKELG
SEQ ID NO:5  (441) NAELLVLMENERTLDFHDSNVKNLYDKVRLQLRDNAKELG
                   481                                   520
SEQ ID NO:2  (461) NGCFEFYHKCDNECMESIRNGTYNYPQYSEEARLKREEIS
SEQ ID NO:4  (477) NGCFEFYHKCDNECMESIRNGTYNYPQYSEEARLKREEIS
SEQ ID NO:5  (481) NGCFEFYHKCDNECMESIRNGTYNYPQYSEEARLKREEIS
                   521                                   560
SEQ ID NO:2  (501) GVKLESIGTYQILSIYSTVASSLALAIMMAGLSLWMCSNG
SEQ ID NO:4  (517) GVKLESIGTYQILSIYSTVASSLALAIMMAGLSLWMCSNG
SEQ ID NO:5  (521) GVKLESIGTYQILSIYSTVASSLALAIMMAGLSLWMCSNG
                   561
SEQ ID NO:2  (541) SLQCRICI-
SEQ ID NO:4  (557) SLQCRICI-
SEQ ID NO:5  (561) SLQCRICI-
```

```
                      1                                      40
SEQ ID NO:10     (1)  MEKIVLLLAIVSLVKSDQICIGYHANNSTEQVDTIMEKNV
SEQ ID NO:12     (1)  MEKIVLLFAIVSLVRSDQICIGYHANNSTKQVDTIMEKNV
SEQ ID NO:14     (1)  MEKIVLLFAIVSLVKSDQICIGYHANNSTEQVDTIMEKNV
 SEQ ID NO:2     (1)  ----------------DQICIGYHANNSTEQVDTIMEKNV
 SEQ ID NO:4     (1)  MEKIVLLLAIVSLVKSDQICIGYHANNSTEQVDTIMEKNV
 SEQ ID NO:5     (1)  MEKIVLLLAIVSLVKSDQICIGYHANNSTEQVDTIMEKNV
                      41                                     80
SEQ ID NO:10    (41)  TVTHAQDILEKTHNGKLCDLDGVKPLILRDCSVAGWLLGN
SEQ ID NO:12    (41)  TVTHAQDILEKTHNGKLCSLNGVKPLILRDCSVAGWLLGN
SEQ ID NO:14    (41)  TVTHAQDILEKKHNGKLCDLDGVKPLILRDCSVAGWLLGN
 SEQ ID NO:2    (25)  TVTHAQDILEKTHNGKLCDLDGVKPLILRDCSVAGWLLGN
 SEQ ID NO:4    (41)  TVTHAQDILEKTHNGKLCDLDGVKPLILRDCSVAGWLLGN
 SEQ ID NO:5    (41)  TVTHAQDILEKTHNGKLCDLDGVKPLILRDCSVAGWLLGN
                      81                                    120
SEQ ID NO:10    (81)  PMCDEFIKVQEWSYIVEKASPTNDLCYPGSFNDYEELKHL
SEQ ID NO:12    (81)  PMCDEFLNVPEWSYIVEKDNPVNGLCYPGDFNDYEELKHL
SEQ ID NO:14    (81)  PMCDEFINVPEWSYIVEKANPVNDLCYPGDFNDYEELKHL
 SEQ ID NO:2    (65)  PMCDEFINVPEWSYIVEKANPANDLCYPGNLNDYEELKHL
 SEQ ID NO:4    (81)  PMCDEFINVPEWSYIVEKANPANDLCYPGNLNDYEELKHL
 SEQ ID NO:5    (81)  PMCDEFINVPEWSYIVEKANPANDLCYPGNLNDYEELKHL
```

Figure 5 (3/5)

```
                          121                                    160
SEQ ID NO:10   (121)  LSRIKHFEKIRIIPKSDWSDHEASLGVSSACPYLGSPSFF
SEQ ID NO:12   (121)  LSCTKHFEKIRIIPRDSWPNHEASLGVSSACPYNGRSSFF
SEQ ID NO:14   (121)  LSRINHFEKIQIIPKSSWSSHEASLGVSSACPYQGKSSFF
 SEQ ID NO:2   (105)  LSRINHFEKIQIIPKSSWSDHEASSGVSSACPYQGKSSFF
 SEQ ID NO:4   (121)  LSRINHFEKIQIIPKSSWSDHEASSGVSSACPYQGKSSFF
 SEQ ID NO:5   (121)  LSRINHFEKIQIIPKSSWSDHEASSGVSSACPYQGKSSFF
                      161                                    200
SEQ ID NO:10   (161)  RNVVWLIKKNSTYPTIKKSYKNTNQEDLLVLWGIHHSNNV
SEQ ID NO:12   (161)  RNVVWLIKKNNAYPTIKRSYSNTNKEDLLILWGIHHPNDA
SEQ ID NO:14   (161)  RNVVWLINKNSTYPTIKRSYNNTNQEDLLVLWGIHHPNDA
 SEQ ID NO:2   (145)  RNVVWLIKKNSAYPTIKRSYNNTNQEDLLVLWGIHHPNDA
 SEQ ID NO:4   (161)  RNVVWLIKKNSAYPTIKRSYNNTNQEDLLVLWGIHHPNDA
 SEQ ID NO:5   (161)  RNVVWLIKKNSAYPTIKRSYNNTNQEDLLVLWGIHHPNDA
                      201                                    240
SEQ ID NO:10   (201)  EEQTRLYQNPITYISIGTSTLNQRLVPKIATRSKVHGQSG
SEQ ID NO:12   (201)  AEQTKLYQNPTTYVSVGTSTLNQRSIPKIATRPELNGQSG
SEQ ID NO:14   (201)  AEQTKLYQNPTTYISVGTSTLNQRLVPRIATRSKVNGQSG
 SEQ ID NO:2   (185)  AEQTRLYQNPTTYISVGTSTLNQRLVPKIAIRSKVNGQSG
 SEQ ID NO:4   (201)  AEQTRLYQNPTTYISVGTSTLNQRLVPKIAIRSKVNGQSG
 SEQ ID NO:5   (201)  AEQTRLYQNPTTYISVGTSTLNQRLVPKIAIRSKVNGQSG
                      241                                    280
SEQ ID NO:10   (241)  RMDFFWTILNPNDTINFESNGNFIAPEYAYKIVKKGDSAI
SEQ ID NO:12   (241)  RMEFFWTILKPSDTINFESNGNFIAPEYAYKIVKKGDSAI
SEQ ID NO:14   (241)  RMEFFWTILKPNDAINFESNGNFIAPEYAYKIVKKGDSTI
 SEQ ID NO:2   (225)  RMEFFWTILKPNDAINFESNGNFIAPEYAYKIVKKGDSAI
 SEQ ID NO:4   (241)  RMEFFWTILKPNDAINFESNGNFIAPEYAYKIVKKGDSAI
 SEQ ID NO:5   (241)  RMEFFWTILKPNDAINFESNGNFIAPEYAYKIVKKGDSAI
                      281                                    320
SEQ ID NO:10   (281)  MKSELEYGDCNTKCQTPMGAINSSMPFHNIHPLTIGECPK
SEQ ID NO:12   (281)  MKSGLEYGNCNTKCQTPIGAINSSMPLHNIHPLTIGECPK
SEQ ID NO:14   (281)  MKSELEYGNCNTKCQTPMGAINSSMPFHNIHPLTIGECPK
 SEQ ID NO:2   (265)  MKSELEYGNCNTKCQTPMGAINSSMPFHNIHPLTIGECPK
 SEQ ID NO:4   (281)  MKSELEYGNCNTKCQTPMGAINSSMPFHNIHPLTIGECPK
 SEQ ID NO:5   (281)  MKSELEYGNCNTKCQTPMGAINSSMPFHNIHPLTIGECPK
                      321                                    360
SEQ ID NO:10   (321)  YVKSNRLVLATGLRNSPQRESRRKKRGLFGAIAGFIEGGW
SEQ ID NO:12   (321)  YVKSDRLVLATGLRNTPQRK--RKKRGLFGAIAGFIEGGW
SEQ ID NO:14   (321)  YVKSNRLVLATGLRNSPQRE----TRGLFGAIAGFIEGGW
 SEQ ID NO:2   (305)  YVKSNRLVLATGLRNSPQRE----TRGLFGAIAGFIEGGW
 SEQ ID NO:4   (321)  YVKSNRLVLATGLRNSPQRE----TRGLFGAIAGFIEGGW
 SEQ ID NO:5   (321)  YVKSNRLVLATGLRNSPQRERRRKKRGLFGAIAGFIEGGW
```

Figure 5 (4/5)

```
                     361                                    400
SEQ ID NO:10  (361)  QGMVDGWYGYHHSNEQGSGYAADKESTQKAIDGVTNKVNS
SEQ ID NO:12  (359)  QGMVDGWYGYHHSNEQGSGYAADKESTQRAIDGITNKVNS
SEQ ID NO:14  (357)  QGMVDGWYGYHHSNEQGSGYAADKESTQKAIDGVTNKVNS
 SEQ ID NO:2  (341)  QGMVDGWYGYHHSNEQGSGYAADKESTQKAIDGVTNKVNS
 SEQ ID NO:4  (357)  QGMVDGWYGYHHSNEQGSGYAADKESTQKAIDGVTNKVNS
 SEQ ID NO:5  (361)  QGMVDGWYGYHHSNEQGSGYAADKESTQKAIDGVTNKVNS
                     401                                    440
SEQ ID NO:10  (401)  IIDKMNTQFEAVGREFNNLERRIENLNKKMEDGFLDVWTY
SEQ ID NO:12  (399)  IIDKMNTQFEAVGKEFNNLERRIENLNKKMEDGFLDVWTY
SEQ ID NO:14  (397)  IIDKMNTQFEAVGREFNNLERRIENLNKKMEDGFLDVWTY
 SEQ ID NO:2  (381)  IIDKMNTQFEAVGREFNNLERRIENLNKKMEDGFLDVWTY
 SEQ ID NO:4  (397)  IIDKMNTQFEAVGREFNNLERRIENLNKKMEDGFLDVWTY
 SEQ ID NO:5  (401)  IIDKMNTQFEAVGREFNNLERRIENLNKKMEDGFLDVWTY
                     441                                    480
SEQ ID NO:10  (441)  NAELLVLMENERTLDFHDSNVKNLYDKVRLQLRDNAKELG
SEQ ID NO:12  (439)  NAELLVLMENERTLDFHDANVKSLYDKVRLQLKDNARELG
SEQ ID NO:14  (437)  NAELLVLMENERTLDFHDSNVKNLYDKVRLQLRDNAKELG
 SEQ ID NO:2  (421)  NAELLVLMENERTLDFHDSNVKNLYDKVRLQLRDNAKELG
 SEQ ID NO:4  (437)  NAELLVLMENERTLDFHDSNVKNLYDKVRLQLRDNAKELG
 SEQ ID NO:5  (441)  NAELLVLMENERTLDFHDSNVKNLYDKVRLQLRDNAKELG
                     481                                    520
SEQ ID NO:10  (481)  NGCFEFYHKCDNECMESIRNGTYNYPQYSEEARLKREEIS
SEQ ID NO:12  (479)  NGCFEFYHKCDNECMESIRNGTYNYPQYSEEARLNREEIS
SEQ ID NO:14  (477)  NGCFEFYHKCDNECMESVRNGTYDYPQYSEEARLKREEIS
 SEQ ID NO:2  (461)  NGCFEFYHKCDNECMESIRNGTYNYPQYSEEARLKREEIS
 SEQ ID NO:4  (477)  NGCFEFYHKCDNECMESIRNGTYNYPQYSEEARLKREEIS
 SEQ ID NO:5  (481)  NGCFEFYHKCDNECMESIRNGTYNYPQYSEEARLKREEIS
                     521                                    560
SEQ ID NO:10  (521)  GVKLESIGTYQILSIYSTVASSLALAIMMAGLSLWMCSNG
SEQ ID NO:12  (519)  GVKLESMGIYQILSIYSTVASSLALAIMIAGLSFWMCSNG
SEQ ID NO:14  (517)  GVKLESIGIYQILSIYSTVASSLALAIMVAGLSLWMCSNG
 SEQ ID NO:2  (501)  GVKLESIGTYQILSIYSTVASSLALAIMMAGLSLWMCSNG
 SEQ ID NO:4  (517)  GVKLESIGTYQILSIYSTVASSLALAIMMAGLSLWMCSNG
 SEQ ID NO:5  (521)  GVKLESIGTYQILSIYSTVASSLALAIMMAGLSLWMCSNG
                     561
SEQ ID NO:10  (561)  SLQCRICI-
SEQ ID NO:12  (559)  SLQCRICI-
SEQ ID NO:14  (557)  SLQCRICI-
 SEQ ID NO:2  (541)  SLQCRICI-
 SEQ ID NO:4  (557)  SLQCRICI-
 SEQ ID NO:5  (561)  SLQCRICI-
```

Figure 5 (5/5)

Sequence identity percentage at the protein level

| SEQ ID NO: | 2 | 4 | 5 | 8 | 10 | 12 | 14 |
|---|---|---|---|---|---|---|---|
| 2 | 100 | 97.0% | 96.1% | 93.7% | 91.4% | 87.5% | 94.3% |
| 4 | | 100 | 98.9% | 96.3% | 94.0% | 89.8% | 96.8% |
| 5 | | | 100 | 97.0% | 94.7% | 90.0% | 96.0% |
| 8 | | | | 100 | 94.5% | 90.0% | 95.6% |
| 10 | | | | | 100 | 88.2% | 93.0% |
| 12 | | | | | | 100 | 90.1% |
| 14 | | | | | | | 100 |

Figure 6 (1/6)

MerB01 vector sequence (SEQ ID NO:6)

1 aattcaccat gcaggtcctg aacacgatgg tcaacaagca cttcctctcc ctgtccgtcc
61 tcatcgtcct cctcgggctg agcagcaacc tcaccgccgg cgaccagatc tgcatcggct
121 accacgccaa caattccacc gagcaggtgg acacgatcat ggaaaagaac gtgaccgtca
181 cccacgccca ggacatcctc gagaagacgc acaacgggaa gctctgcgac ctcgacggcg
241 tgaagccgct catcctccgc gactgctccg tggccggctg gctcctgggc aaccccatgt
301 gcgacgagtt catcaacgtc ccggagtggt cctacatcgt ggagaaggcc aaccccgcca
361 acgatctgtg ctacccgggg aacctcaacg actacgagga actcaagcac ctgctctccc
421 gcatcaacca cttcgagaag atccagatca tcccgaagtc cagctggtcc gaccacgagg
481 cgtccagcgg cgtcagctcc gcctgcccgt accaaggcaa gtccagcttc ttccggaacg
541 tcgtgtggct gatcaagaag aactcggcct accccaccat caagaggagc tacaacaata
601 cgaaccagga ggacctgctc gtgctgtggg ggatccacca cccgaacgac gcggccgagc
661 agacccgcct gtaccagaac cccaccacgt acatctccgt cgggaccagc acgctcaacc
721 agcgcctggt gccgaagatc gccatccgca gcaaggtgaa cgggcagtcg ggtcgcatgg
781 agttcttctg gacgatcctg aagcccaacg acgccatcaa cttcgagagc aacggcaact
841 tcatcgcccc ggagtacgcg tacaagatcg tcaagaaggg ggacagcgcc atcatgaagt
901 cggagctgga gtacgggaac tgtaacacga agtgccagac ccccatgggc gcgatcaact
961 ccagcatgcc cttccacaac atccacccgc tcaccatcgg cgagtgcccc aagtacgtca
1021 agagcaacag gctggtcctg gccacgggcc tccgcaacag cccccagcgg gagacccgcg
1081 ggctcttcgg ggccatcgcg gggttcatcg agggcgggtg gcagggcatg gtggacggtt
1141 ggtacggcta ccaccacagc aacgagcagg gctcgggcta cgccgcggac aaggagtcca
1201 cccagaaggc catcgacggc gtgaccaaca aggtgaactc catcatcgac aagatgaaca
1261 cccagttcga ggccgtcggg cgcgagttca acaacctgga gcgccggatc gagaacctca
1321 acaagaagat ggaggacggg ttcctggacg tgtggaccta caacgcggag ctgctcgtgc
1381 tcatggagaa cgagaggacg ctcgacttcc acgactccaa cgtcaagaac ctgtacgaca
1441 aggtccggct gcagctccgg gacaacgcca aggagctggg caacggctgc ttcgagttct
1501 accacaagtg cgacaacgag tgcatggagt ccatcaggaa cggcacgtac aactaccccc
1561 agtattccga ggaggctcgc ctcaagaggg aggagatcag cggcgtcaag ctcgagtcca
1621 tcgggaccta ccagatcctc tccatctact ccacggtggc gtccagcctc gccctcgcca
1681 tcatgatggc tggcctgtcg ctgtggatgt gctccaacgg gagcctccag tgccgcatct
1741 gcatctaaga gctcgaattt ccccgatcgt tcaaacattt ggcaataaag tttcttaaga
1801 ttgaatcctg ttgccggtct tgcgatgatt atcatataat ttctgttgaa ttacgttaag
1861 catgtaataa ttaacatgta atgcatgacg ttatttatga gatgggtttt tatgattaga
1921 gtcccgcaat tatacattta atacgcgata gaaaacaaaa tatagcgcgc aaactaggat
1981 aaattatcgc gcgcggtgtc atctatgtta ctagatcggg aattaattca gatcggctga
2041 gtggctcctt caacgttgcg gttctgtcag ttccaaacgt aaaacggctt gtcccgcgtc
2101 atcggcgggg gtcataacgt gactccctta attctccgct catgatcaga ttgtcgtttc
2161 ccgccttcag tttaaactat cagtgtttga caggatatat tggcgggtaa acctaagaga
2221 aaagagcgtt tattagaata atcggatatt taaaagggcg tgaaaaggtt tatccgttcg
2281 tccatttgta tgtgcatgcc aaccacaggg ttccccagat ctggcgccgg ccagcgagac
2341 gagcaagatt ggccgccgcc cgaaacgatc cgacagcgcg cccagcacag gtgcgcaggc
2401 aaattgcacc aacgcataca gcgccagcag aatgccatag tgggcggtga cgtcgttcga
2461 gtgaaccaga tcgcgcagga ggcccggcag caccggcata atcaggccga tgccgacagc
2521 gtcgagcgcg acagtgctca gaattacgat caggggtatg ttgggtttca cgtctggcct
2581 ccggaccagc ctccgctggt ccgattgaac gcgcggattc tttatcactg ataagttggt
2641 ggacatatta tgtttatcag tgataaagtg tcaagcatga caaagttgca gccgaataca
2701 gtgatccgtg ccgccctgga cctgttgaac gaggtcggcg tagacggtct gacgacacgc

Figure 6 (2/6)

```
2761 aaactggcgg aacggttggg ggttcagcag ccggcgcttt actggcactt caggaacaag
2821 cgggcgctgc tcgacgcact ggccgaagcc atgctggcgg agaatcatac gcattcggtg
2881 ccgagagccg acgacgactg gcgctcattt ctgatcggga atgcccgcag cttcaggcag
2941 gcgctgctcg cctaccgcga tggcgcgcgc atccatgccg gcacgcgacc gggcgcaccg
3001 cagatggaaa cggccgacgc gcagcttcgc ttcctctgcg aggcgggttt ttcggccggg
3061 gacgccgtca atgcgctgat gacaatcagc tacttcactg ttggggccgt gcttgaggag
3121 caggccggcg acagcgatgc cggcgagcgc ggcggcaccg ttgaacaggc tccgctctcg
3181 ccgctgttgc gggccgcgat agacgccttc gacgaagccg gtccggacgc agcgttcgag
3241 cagggactcg cggtgattgt cgatggattg gcgaaaagga ggctcgttgt caggaacgtt
3301 gaaggaccga gaaagggtga cgattgatca ggaccgctgc cggagcgcaa cccactcact
3361 acagcagagc catgtagaca acatcccctc cccctttcca ccgcgtcaga cgcccgtagc
3421 agcccgctac gggctttttc atgccctgcc ctagcgtcca agcctcacgg ccgcgctcgg
3481 cctctctggc ggccttctgg cgctcttccg cttcctcgct cactgactcg ctgcgctcgg
3541 tcgttcggct gcggcgagcg gtatcagctc actcaaaggc ggtaatacgg ttatccacag
3601 aatcagggga taacgcagga aagaacatgt gagcaaaagg ccagcaaaag gccaggaacc
3661 gtaaaaaggc cgcgttgctg gcgtttttcc ataggctccg cccccctgac gagcatcaca
3721 aaaatcgacg ctcaagtcag aggtggcgaa acccgacagg actataaaga taccaggcgt
3781 ttccccctgg aagctccctc gtgcgctctc ctgttccgac cctgccgctt accggatacc
3841 tgtccgcctt tctcccttcg ggaagcgtgg cgctttctcg ctgcataacc ctgcttcggg
3901 gtcattatag cgatttttc ggtatatcca tcctttttcg cacgatatac aggattttgc
3961 caaagggttc gtgtagactt tccttggtgt atccaacggc gtcagccggg caggataggt
4021 gaagtaggcc cacccgcgag cgggtgttcc ttcttcactg tcccttattc gcacctggcg
4081 gtgctcaacg ggaatcctgc tctgcgaggc tggccggcta ccgccggcgt aacagatgag
4141 ggcaagcgga tggctgatga aaccaagcca accaggaagg gcagcccacc tatcaaggtg
4201 tactgccttc cagacgaacg aagagcgatt gaggaaaagg cggcggcggc cggcatgagc
4261 ctgtcggcct acctgctggc cgtcggccag ggctacaaaa tcacgggcgt cgtggactat
4321 gagcacgtcc gcgagctggc ccgcatcaat ggcgacctgg gccgcctggg cggcctgctg
4381 aaactctggc tcaccgacga cccgcgcacg gcgcggttcg gtgatgccac gatcctcgcc
4441 ctgctggcga agatcgaaga gaagcaggac gagcttggca aggtcatgat gggcgtggtc
4501 cgcccgaggg cagagccatg acttttttag ccgctaaaac ggccgggggg tgcgcgtgat
4561 tgccaagcac gtccccatgc gctccatcaa gaagagcgac ttcgcggagc tggtgaagta
4621 catcaccgac gagcaaggca agaccgagcg cctttgcgac gctcaccggg ctggttgccc
4681 tcgccgctgg gctggcggcc gtctatggcc ctgcaaacgc gccagaaacg ccgtcgaagc
4741 cgtgtgcgag acaccgcggc cgccggcgtt gtggatacct cgcggaaaac ttggccctca
4801 ctgacagatg aggggcggac gttgacactt gaggggccga ctcacccggc gcggcgttga
4861 cagatgaggg gcaggctcga tttcggccgg cgacgtggag ctggccagcc tcgcaaatcg
4921 gcgaaaacgc ctgattttac gcgagtttcc cacagatgat gtggacaagc ctggggataa
4981 gtgccctgcg gtattgacac ttgaggggcg cgactactga cagatgaggg gcgcgatcct
5041 tgacacttga ggggcagagt gctgacagat gaggggcgca cctattgaca tttgaggggc
5101 tgtccacagg cagaaaatcc agcatttgca agggtttccg cccgtttttc ggccaccgct
5161 aacctgtctt ttaacctgct tttaaaccaa tatttataaa ccttgttttt aaccagggct
5221 gcgccctgtg cgcgtgaccg cgcacgccga aggggggtgc ccccccttct cgaaccctcc
5281 cggcccgcta acgcgggcct cccatccccc caggggctgc gcccctcggc cgcgaacggc
5341 ctcaccccaa aaatggcagc gctggcagtc cttgccattg ccgggatcgg ggcagtaacg
5401 ggatgggcga tcagcccgag cgcgacgccc ggaagcattg acgtgccgca ggtgctggca
5461 tcgacattca gcgaccaggt gccgggcagt gagggcggcg gcctgggtgg cggcctgccc
5521 ttcacttcgg ccgtcggggc attcacggac ttcatggcgg ggccggcaat ttttaccttg
5581 ggcattcttg gcatagtggt cgcgggtgcc gtgctcgtgt tcggggtgc gataaaccca
5641 gcgaaccatt tgaggtgata ggtaagatta taccgaggta tgaaaacgag aattggacct
```

Figure 6 (3/6)

5701 ttacagaatt actctatgaa gcgccatatt taaaaagcta ccaagacgaa gaggatgaag
5761 aggatgagga ggcagattgc cttgaatata ttgacaatac tgataagata atatatcttt
5821 tatatagaag atatcgccgt atgtaaggat ttcagggggc aaggcatagg cagcgcgctt
5881 atcaatatat ctatagaatg ggcaaagcat aaaaacttgc atggactaat gcttgaaacc
5941 caggacaata accttatagc ttgtaaattc tatcataatt gggtaatgac tccaacttat
6001 tgatagtgtt ttatgttcag ataatgcccg atgactttgt catgcagctc caccgatttt
6061 gagaacgaca gcgacttccg tcccagccgt gccaggtgct gcctcagatt caggttatgc
6121 cgctcaattc gctgcgtata tcgcttgctg attacgtgca gctttccctt caggcgggat
6181 tcatacagcg gccagccatc cgtcatccat atcaccacgt caaagggtga cagcaggctc
6241 ataagacgcc ccagcgtcgc catagtgcgt tcaccgaata cgtgcgcaac aaccgtcttc
6301 cggagactgt catacgcgta aaacagccag cgctggcgcg atttagcccc gacatagccc
6361 cactgttcgt ccatttccgc gcagacgatg acgtcactgc ccggctgtat gcgcgaggtt
6421 accgactgcg gcctgagttt tttaagtgac gtaaaatcgt gttgaggcca acgcccataa
6481 tgcgggctgt tgcccggcat ccaacgccat tcatggccat atcaatgatt ttctggtgcg
6541 taccgggttg agaagcggtg taagtgaact gcagttgcca tgttttacgg cagtgagagc
6601 agagatagcg ctgatgtccg gcggtgcttt tgccgttacg caccaccccg tcagtagctg
6661 aacaggaggg acagctgata gacacagaag ccactggagc acctcaaaaa caccatcata
6721 cactaaatca gtaagttggc agcatcaccc ataattgtgg tttcaaaatc ggctccgtcg
6781 atactatgtt atacgccaac tttgaaaaca actttgaaaa agctgttttc tggtatttaa
6841 ggttttagaa tgcaaggaac agtgaattgg agttcgtctt gttataatta gcttcttggg
6901 gtatctttaa atactgtaga aaagaggaag gaaataataa atggctaaaa tgagaatatc
6961 accggaattg aaaaaactga tcgaaaaata ccgctgcgta aaagatacgg aaggaatgtc
7021 tcctgctaag gtatataagc tggtgggaga aaatgaaaac ctatatttaa aaatgacgga
7081 cagccggtat aaagggacca cctatgatgt ggaacgggaa aaggacatga tgctatggct
7141 ggaaggaaag ctgcctgttc caaaggtcct gcactttgaa cggcatgatg gctggagcaa
7201 tctgctcatg agtgaggccg atggcgtcct ttgctcggaa gagtatgaag atgaacaaag
7261 ccctgaaaag attatcgagc tgtatgcgga gtgcatcagg ctctttcact ccatcgacat
7321 atcggattgt ccctatacga atagcttaga cagccgctta gccgaattgg attacttact
7381 gaataacgat ctggccgatg tggattgcga aaactgggaa gaagacactc catttaaaga
7441 tccgcgcgag ctgtatgatt ttttaaagac ggaaaagccc gaagaggaac ttgtcttttc
7501 ccacggcgac ctgggagaca gcaacatctt tgtgaaagat ggcaaagtaa gtggctttat
7561 tgatcttggg agaagcggca gggcggacaa gtggtatgac attgccttct gcgtccggtc
7621 gatcagggag gatatcgggg aagaacagta tgtcgagcta ttttttgact tactggggat
7681 caagcctgat tgggagaaaa taaaatatta tattttactg gatgaattgt tttagtacct
7741 agatgtggcg caacgatgcc ggcgacaagc aggagcgcac cgacttcttc cgcatcaagt
7801 gttttggctc tcaggccgag gcccacggca agtatttggg caaggggtcg ctggtattcg
7861 tgcagggcaa gattcggaat accaagtacg agaaggacgg ccagacggtc tacgggaccg
7921 acttcattgc cgataaggtg gattatctgg acaccaaggc accaggcggg tcaaatcagg
7981 aataagggca cattgccccg gcgtgagtcg gggcaatccc gcaaggaggg tgaatgaatc
8041 ggacgtttga ccggaaggca tacaggcaag aactgatcga cgcggggttt tccgccgagg
8101 atgccgaaac catcgcaagc cgcaccgtca tgcgtgcgcc ccgcgaaacc ttccagtccg
8161 tcggctcgat ggtccagcaa gctacggcca agatcgagcg cgacagcgtg caactggctc
8221 cccctgccct gcccgcgcca tcggccgccg tggagcgttc gcgtcgtctc gaacaggagg
8281 cggcaggttt ggcgaagtcg atgaccatcg acacgcgagg aactatgacg accaagaagc
8341 gaaaaaccgc cggcgaggac ctggcaaaac aggtcagcga ggccaagcag gccgcgttgc
8401 tgaaacacac gaagcagcag atcaaggaaa tgcagctttc cttgttcgat attgcgccgt
8461 ggccggacac gatgcgagcg atgccaaacg acacggcccg ctctgccctg ttcaccacgc
8521 gcaacaagaa aatcccgcgc gaggcgctgc aaaacaaggt cattttccac gtcaacaagg
8581 acgtgaagat cacctacacc ggcgtcgagc tgcgggccga cgatgacgaa ctggtgtggc

Figure 6 (4/6)

```
8641 agcaggtgtt ggagtacgcg aagcgcaccc ctatcggcga gccgatcacc ttcacgttct
8701 acgagctttg ccaggacctg ggctggtcga tcaatggccg gtattacacg aaggccgagg
8761 aatgcctgtc gcgcctacag gcgacggcga tgggcttcac gtccgaccgc gttgggcacc
8821 tggaatcggt gtcgctgctg caccgcttcc gcgtcctgga ccgtggcaag aaaacgtccc
8881 gttgccaggt cctgatcgac gaggaaatcg tcgtgctgtt tgctggcgac cactacacga
8941 aattcatatg ggagaagtac cgcaagctgt cgccgacggc ccgacggatg ttcgactatt
9001 tcagctcgca ccgggagccg tacccgctca agctggaaac cttccgcctc atgtgcggat
9061 cggattccac ccgcgtgaag aagtggcgcg agcaggtcgg cgaagcctgc gaagagttgc
9121 gaggcagcgg cctggtggaa cacgcctggg tcaatgatga cctggtgcat tgcaaacgct
9181 agggccttgt ggggtcagtt ccggctgggg gttcagcagc cagcgcttta ctggcatttc
9241 aggaacaagc gggcactgct cgacgcactt gcttcgctca gtatcgctcg ggacgcacgg
9301 cgcgctctac gaactgccga taaacagagg attaaaattg acaattgtga ttaaggctca
9361 gattcgacgg cttggagcgg ccgacgtgca ggatttccgc gagatccgat tgtcggccct
9421 gaagaaagct ccagagatgt tcgggtccgt ttacgagcac gaggagaaaa agcccatgga
9481 ggcgttcgct gaacggttgc gagatgccgt ggcattcggc gcctacatcg acggcgagat
9541 cattgggctg tcggtcttca aacaggagga cggccccaag gacgctcaca aggcgcatct
9601 gtccggcgtt ttcgtggagc ccgaacagcg aggccgaggg gtcgccggta tgctgctgcg
9661 ggcgttgccg gcgggtttat tgctcgtgat gatcgtccga cagattccaa cgggaatctg
9721 gtggatgcgc atcttcatcc tcggcgcact taatatttcg ctattctgga gcttgttgtt
9781 tatttcggtc taccgcctgc cgggcggggt cgcggcgacg gtaggcgctg tgcagccgct
9841 gatggtcgtg ttcatctctg ccgctctgct aggtagcccg atacgattga tggcggtcct
9901 gggggctatt tgcggaactg cgggcgtggc gctgttggtg ttgacaccaa acgcagcgct
9961 agatcctgtc ggcgtcgcag cgggcctggc gggggcggtt tccatggcgt tcggaaccgt
10021 gctgacccgc aagtggcaac ctcccgtgcc tctgctcacc tttaccgcctggcaactggc
10081 ggccggagga cttctgctcg ttccagtagc tttagtgttt gatccgccaatcccgatgcc
10141 tacaggaacc aatgttctcg gcctggcgtg gctcggcctg atcggagcgggtttaaccta
10201 cttcctttgg ttccggggga tctcgcgact cgaacctaca gttgtttccttactgggctt
10261 tctcagcccc agatctgggg tcgatcagcc ggggatgcat caggccgacagtcggaactt
10321 cgggtccccg acctgtacca ttcggtgagc aatggatagg ggagttgatatcgtcaacgt
10381 tcacttctaa agaaatagcg ccactcagct tcctcagcgg ctttatccagcgatttccta
10441 ttatgtcggc atagttctca agatcgacag cctgtcacgg ttaagcgagaaatgaataag
10501 aaggctgata attcggatct ctgcgaggga gatgatattt gatcacaggcagcaacgctc
10561 tgtcatcgtt acaatcaaca tgctaccctc cgcgagatca tccgtgtttcaaacccggca
10621 gcttagttgc cgttcttccg aatagcatcg gtaacatgag caaagtctgccgccttacaa
10681 cggctctccc gctgacgccg tcccggactg atgggctgcc tgtatcgagtggtgattttg
10741 tgccgagctg ccggtcgggg agctgttggc tggctggtgg caggatatattgtggtgtaa
10801 acaaattgac gcttagacaa cttaataaca cattgcggac gtttttaatgtactggggtg
10861 gtttttcttt tcaccagtga gacgggcaac agctgattgc ccttcaccgcctggccctga
10921 gagagttgca gcaagcggtc cacgctggtt tgccccagca ggcgaaaatcctgtttgatg
10981 gtggttccga aatcggcaaa atcccttata aatcaaaaga atagcccgagatagggttga
11041 gtgttgttcc agtttggaac aagagtccac tattaaagaa cgtggactccaacgtcaaag
11101 ggcgaaaaac cgtctatcag ggcgatggcc cactacgtga accatcacccaaatcaagtt
11161 ttttggggtc gaggtgccgt aaagcactaa atcggaaccc taaagggagcccccgattta
11221 gagcttgacg gggaaagccg gcgaacgtgg cgagaaagga agggaagaaagcgaaaggag
11281 cgggcgccat tcaggctgcg caactgttgg gaagggcgat cggtgcgggcctcttcgcta
11341 ttacgccagc tggcgaaagg gggatgtgct gcaaggcgat taagttgggtaacgccaggg
11401 ttttcccagt cacgacgttg taaaacgacg gccagtgaat tgccatcttgaaagaaatat
11461 agtttaaata tttattgata aaataagtca ggtattatag tccaagcaaaaacataattt
11521 attgatgcaa agtttaaatt cagaaatatt tcaataactg attatatcagctggtacatt
```

Figure 6 (5/6)

```
11581 gccgtagatg aaagactgag tgcgatatta tgtgtaatac ataaattgatgatatagcta
11641 gcttagctca tcgggggatc cttaatcgac tctagctaga acgaattgttaggtggcggt
11701 acttgggtcg atatcaaagt gcatcacttc ttcccgtatg cccaactttgtatagagagc
11761 cactgcggga tcgtcaccgt aatctgcttg cacgtagatc acataagcaccaagcgcgtt
11821 ggcctcatgc ttgaggagat tgatgagcgc ggtggcaatg ccctgcctccggtgctcgcc
11881 ggagactgcg agatcataga tatagatctc actacgcggc tgctcaaacctgggcagaac
11941 gtaagccgcg agagcgccaa caaccgcttc ttggtcgaag gcagcaagcgcgatgaatgt
12001 cttactacgg agcaagttcc cgaggtaatc ggagtccggc tgatgttgggagtaggtggc
12061 tacgtctccg aactcacgac cgaaaagatc aagagcagcc cgcatggatttgacttggtc
12121 agggccgagc ctacatgtgc gaatgatgcc catacttgag ccacctaactttgttttagg
12181 gcgactgccc tgctgcgtaa catcgttgct gctgcgtacc atggagatctggattgagag
12241 tgaatatgag actctaattg gataccgagg ggaatttatg gaagtcagtggagcattttt
12301 gacaagaaat atttgctagc tgatagtgac cttaggcgac ttttgaacgcgcaataatgg
12361 tttctgacgt atgtgcttag ctcattaaac tccagaaacc cgcggctgagtggctccttc
12421 aacgttgcgg ttctgtcagt tccaaacgta aaacggcttg tcccgcgtcatcggcggggg
12481 tcataacgtg actcccttaa ttctccgctc atgatcttga tcccctgcgccatcagatcc
12541 ttggcggcaa gaaagccatc cagtttactt tgcagggctt cccaaccttaccagagggcg
12601 ccccagctgg caattccggt tcgcttgctg tccataaaac cgcccagtctagctatcgcc
12661 atgtaagccc actgcaagct acctgctttc tctttgcgct tgcgttttcccttgtccaga
12721 tagcccagta gctgacattc atccggggtc agcaccgttt ctgcggactggctttctacg
12781 tgttccgctt cctttagcag cccttgcgcc ctgagtgctt gcggcagcgtgaagctctgg
12841 acatcatgtt ggatatgaaa caactattat ttatctacat gttttagatgttatctgatt
12901 atttttatac cgtagtcttc tattgatgag gagtctaagg ctatagaattatatatctaa
12961 atgattaata tatatattat taataattaa caataattaa tatattataatttatatata
13021 tatattttat attattataa taatattctt acaaatataa ttattatattcgacggtatc
13081 gataagctcg ggatccctga aagcgacgtt ggatgttaac atctacaaattgccttttct
13141 tatcgaccat gtacgtaagc gcttacgttt ttggtggacc cttgaggaaactggtagctg
13201 ttgtgggcct gtggtctcaa gatggatcat taatttccac cttcacctacgatgggggc
13261 atcgcaccgg tgagtaatat tgtacggcta agagcgaatt tggcctgtaggatccctgaa
13321 agcgacgttg gatgttaaca tctacaaatt gccttttctt atcgaccatgtacgtaagcg
13381 cttacgtttt tggtggaccc ttgaggaaac tggtagctgt tgtgggcctgtggtctcaag
13441 atggatcatt aatttccacc ttcacctacg atgggggca tcgcaccggtgagtaatatt
13501 gtacggctaa gagcgaattt ggcctgtagg atccctgaaa gcgacgttggatgttaacat
13561 ctacaaattg ccttttctta tcgaccatgt acgtaagcgc ttacgtttttggtggaccct
13621 tgaggaaact ggtagctgtt gtgggcctgt ggtctcaaga tggatcattaatttccacct
13681 tcacctacga tgggggcat cgcaccggtg agtaatattg tacggctaagagcgaatttg
13741 gcctgtagga tccgcgagct ggtcaatccc attgcttttg aagcagctcaacattgatct
13801 ctttctcgat cgagggagat ttttcaaatc agtgcgcaag acgtgacgtaagtatccgag
13861 tcagttttta tttttctact aatttggtcg tttatttcgg cgtgtaggacatggcaaccg
13921 ggcctgaatt tcgcgggtat tctgtttcta ttccaacttt ttcttgatccgcagccatta
13981 acgacttttg aatagatacg ctgacacgcc aagcctcgct agtcaaaagtgtaccaaaca
14041 acgctttaca gcaagaacgg aatgcgcgtg acgctcgcgg tgacgccatttcgccttttc
14101 agaaatggat aaatagcctt gcttcctatt atatcttccc ccaaattaattaagaaactc
14161 ccgaggtgag caaggatccg gagtcgagcg cgaagaagag aaagagggaaagcgcgggta
14221 ccgggccccc ccctcgacgg atcaagtgca aaggtccgcc ttgtttctcctctgtctctt
14281 gatctgacta atcttggttt atgattcgtt gagtaatttt ggggaaagctagcttcgtcc
14341 acagtttttt tttcgatgaa cagtgccgca gtggcgctga tcttgtatgctatcctgcaa
14401 tcgtggtgaa cttatttctt ttatatcctt cactcccatg aaaaggctagtaatctttct
14461 cgatgtaaca tcgtccagca ctgctattac cgtgtggtcc atccgacagtctggctgaac
```

Figure 6 (6/6)

```
14521 acatcatacg atattgagca aagatcgatc tatcttccct gttctttaatgaaagacgtc
14581 attttcatca gtatgatcta agaatgttgc aacttgcaag gaggcgtttctttctttgaa
14641 tttaactaac tcgttgagtg gccctgtttc tcggacgtaa ggcctttgctgctccacaca
14701 tgtccattcg aattttaccg tgtttagcaa gggcgaaaag tttgcatcttgatgatttag
14761 cttgactatg cgattgcttt cctggacccg tgcagctgcg gacggatcccccgctcgagg
14821 tcgacggtat cgataagctt gatcagatct gatcg
```

```
               ADH1
  RbcS leader    |
   AmasPmas      |      Alpha amylase signal sequence
     Aocs        |
     Aocs        |      Avian influenza H5N1
     Aocs        |      Glycoprotein HA
                        SEQ ID NO:1

  PNos                             Tnos
                                    RB
  aacCl

  pAg7              MerB01
                    14855 bp
   LB

                                   ORiV

             NptIII
```

Figure 8 (1/3)

```
SEQ ID NO:1     (1) --------------------------------------------------GA
SEQ ID NO:3     (1) ATGGAGAAAATAGTGCTTCTTCTTGCAATAGTCAGTCTTGTTAAAAGTGA

SEQ ID NO:1     (3) CCAGATCTGCATCGGCTACCACGCCAACAATTCCACCGAGCAGGTGGACA
SEQ ID NO:3    (51) TCAGATTTGCATTGGTTACCATGCAAACAATTCAACAGAGCAGGTTGACA

SEQ ID NO:1    (53) CGATCATGGAAAAGAACGTGACCGTCACCCACGCCCAGGACATCCTCGAG
SEQ ID NO:3   (101) CAATAATGGAAAAGAACGTTACTGTTACACATGCCCAAGACATACTGGAA

SEQ ID NO:1   (103) AAGACGCACAACGGGAAGCTCTGCGACCTCGACGGCGTGAAGCCGCTCAT
SEQ ID NO:3   (151) AAGACACACAACGGGAAGCTCTGCGATCTAGATGGAGTGAAGCCTCTAAT

SEQ ID NO:1   (153) CCTCCGCGACTGCTCCGTGGCCGGCTGGCTCCTGGGCAACCCCATGTGCG
SEQ ID NO:3   (201) TTTAAGAGATTGTAGTGTAGCTGGATGGCTCCTCGGGAATCCAATGTGTG

SEQ ID NO:1   (203) ACGAGTTCATCAACGTCCCGGAGTGGTCCTACATCGTGGAGAAGGCCAAC
SEQ ID NO:3   (251) ACGAATTCATCAATGTACCGGAATGGTCTTACATAGTGGAGAAGGCCAAT

SEQ ID NO:1   (253) CCCGCCAACGATCTGTGCTACCCGGGGAACCTCAACGACTACGAGGAACT
SEQ ID NO:3   (301) CCAGCCAATGACCTCTGTTACCCAGGGAATCTCAACGACTATGAAGAACT

SEQ ID NO:1   (303) CAAGCACCTGCTCTCCCGCATCAACCACTTCGAGAAGATCCAGATCATCC
SEQ ID NO:3   (351) AAAACACCTATTGAGCAGAATAAACCATTTTGAGAAAATTCAGATCATCC

SEQ ID NO:1   (353) CGAAGTCCAGCTGGTCCGACCACGAGGCGTCCAGCGGCGTCAGCTCCGCC
SEQ ID NO:3   (401) CCAAAAGTTCTTGGTCCGATCATGAAGCCTCATCAGGGGTGAGCTCAGCA

SEQ ID NO:1   (403) TGCCCGTACCAAGGCAAGTCCAGCTTCTTCCGGAACGTCGTGTGGCTGAT
SEQ ID NO:3   (451) TGTCCATACCAGGGAAAGTCCTCCTTTTTTAGAAATGTGGTATGGCTTAT

SEQ ID NO:1   (453) CAAGAAGAACTCGGCCTACCCCACCATCAAGAGGAGCTACAACAATACGA
SEQ ID NO:3   (501) CAAAAAGAACAGTGCATACCCAACAATAAAGAGAAGCTACAATAATACCA

SEQ ID NO:1   (503) ACCAGGAGGACCTGCTCGTGCTGTGGGGGATCCACCACCCGAACGACGCG
SEQ ID NO:3   (551) ACCAAGAAGATCTTTTGGTACTGTGGGGGATTCACCATCCTAATGATGCG

SEQ ID NO:1   (553) GCCGAGCAGACCCGCCTGTACCAGAACCCCACCACGTACATCTCCGTCGG
SEQ ID NO:3   (601) GCAGAGCAGACAAGGCTATATCAAAACCCAACCACCTATATTTCCGTTGG

SEQ ID NO:1   (603) GACCAGCACGCTCAACCAGCGCCTGGTGCCGAAGATCGCCATCCGCAGCA
SEQ ID NO:3   (651) GACATCAACACTAAACCAGAGATTGGTACCAAAAATAGCTATTAGATCCA

SEQ ID NO:1   (653) AGGTGAACGGGCAGTCGGGTCGCATGGAGTTCTTCTGGACGATCCTGAAG
SEQ ID NO:3   (701) AACTAAACGGGCAAAGTGGAAGAATGGAGTTCTTCTGGACAATTTTAAAA

SEQ ID NO:1   (703) CCCAACGACGCCATCAACTTCGAGAGCAACGGCAACTTCATCGCCCCGGA
SEQ ID NO:3   (751) CCGAATGATGCAATCAACTTCGAGAGTAATGGAAATTTCATTGCTCCAGA

SEQ ID NO:1   (753) GTACGCGTACAAGATCGTCAAGAAGGGGGACAGCGCCATCATGAAGTCGG
SEQ ID NO:3   (801) ATATGCATACAAAATTGTCAAGAAAGGGGACTCTGCAATTATGAAAGTG
```

Figure 8 (2/3)

```
SEQ ID NO:1    (803)  AGCTGGAGTACGGGAACTGTAACACGAAGTGCCAGACCCCCATGGGCGCG
SEQ ID NO:3    (851)  AATTGGAATATGGTAACTGCAACACCAAGTGTCAAACTCCAATGGGGGCG

SEQ ID NO:1    (853)  ATCAACTCCAGCATGCCCTTCCACAACATCCACCCGCTCACCATCGGCGA
SEQ ID NO:3    (901)  ATAAACTCTAGTATGCCATTCCACAACATACACCCTCTCACCATCGGGGA

SEQ ID NO:1    (903)  GTGCCCCAAGTACGTCAAGAGCAACAGGCTGGTCCTGGCCACGGGCCTCC
SEQ ID NO:3    (951)  ATGCCCCAAATATGTGAAATCAAACAGATTAGTCCTTGCGACTGGGCTCA

SEQ ID NO:1    (953)  GCAACAGCCCCCAGCGGAGACCCGC-------------GGGCTCTTCGGG
SEQ ID NO:3   (1001)  GAAATAGCCCTCAAAGAGAGAGAAGAAGAAAAAAGAGAGGACTATTTGGA

SEQ ID NO:1    (991)  GCCATCGCGGGGTTCATCGAGGGCGGGTGGCAGGGCATGGTGGACGGTTG
SEQ ID NO:3   (1051)  GCTATAGCAGGTTTTATAGAGGGAGGATGGCAGGGAATGGTAGATGGTTG

SEQ ID NO:1   (1041)  GTACGGCTACCACCACAGCAACGAGCAGGGCTCGGCTACGCCGCGGACA
SEQ ID NO:3   (1101)  GTATGGGTACCACCATAGCAATGAGCAGGGGAGTGGGTACGCTGCAGACA

SEQ ID NO:1   (1091)  AGGAGTCCACCCAGAAGGCCATCGACGGCGTGACCAACAAGGTGAACTCC
SEQ ID NO:3   (1151)  AAGAATCCACTCAAAAGGCAATAGATGGGGTCACCAATAAGGTCAACTCG

SEQ ID NO:1   (1141)  ATCATCGACAAGATGAACACCCAGTTCGAGGCCGTCGGGCGCGAGTTCAA
SEQ ID NO:3   (1201)  ATCATTGACAAAATGAACACTCAGTTTGAGGCCGTTGGAAGGGAATTTAA

SEQ ID NO:1   (1191)  CAACCTGGAGCGCCGGATCGAGAACCTCAACAAGAAGATGGAGGACGGGT
SEQ ID NO:3   (1251)  TAACTTAGAAAGGAGAATAGAGAATTTAAACAAGAAGATGGAAGACGGAT

SEQ ID NO:1   (1241)  TCCTGGACGTGTGGACCTACAACGCGGAGCTGCTCGTGCTCATGGAGAAC
SEQ ID NO:3   (1301)  TCCTAGATGTCTGGACTTATAATGCTGAACTTCTGGTTCTCATGGAAAAT

SEQ ID NO:1   (1291)  GAGAGGACGCTCGACTTCCACGACTCCAACGTCAAGAACCTGTACGACAA
SEQ ID NO:3   (1351)  GAGAGAACTCTAGACTTTCATGACTCAAATGTTAAGAACCTCTACGACAA

SEQ ID NO:1   (1341)  GGTCCGGCTGCAGCTCCGGGACAACGCCAAGGAGCTGGGCAACGGCTGCT
SEQ ID NO:3   (1401)  GGTCCGACTACAGCTTAGGGATAATGCAAAGGAGCTGGGTAACGGTTGTT

SEQ ID NO:1   (1391)  TCGAGTTCTACCACAAGTGCGACAACGAGTGCATGGAGTCCATCAGGAAC
SEQ ID NO:3   (1451)  TCGAGTTCTATCACAAATGTGATAATGAATGTATGGAAAGTATAAGAAAC

SEQ ID NO:1   (1441)  GGCACGTACAACTACCCCCAGTATTCCGAGGAGGCTCGCCTCAAGAGGGA
SEQ ID NO:3   (1501)  GGAACGTATAACTACCCGCAGTATTCAGAAGAAGCAAGATTAAAAAGAGA

SEQ ID NO:1   (1491)  GGAGATCAGCGGCGTCAAGCTCGAGTCCATCGGGACCTACCAGATCCTCT
SEQ ID NO:3   (1551)  AGAAATAAGTGGAGTAAAATTGGAATCAATAGGAACTTACCAAATACTGT

SEQ ID NO:1   (1541)  CCATCTACTCCACGGTGGCGTCCAGCCTCGCCCTCGCCATCATGATGGCT
SEQ ID NO:3   (1601)  CAATTTATTCAACAGTGGCGAGTTCCCTAGCACTGGCAATCATGATGGCT
```

Figure 8 (3/3)

```
SEQ ID NO:1  (1591) GGCCTGTCGCTGTGGATGTGCTCCAACGGGAGCCTCCAGTGCCGCATCTG
SEQ ID NO:3  (1651) GGTCTATCTTTATGGATGTGCTCCAATGGATCGTTACAATGCAGAATTTG

SEQ ID NO:1  (1641) CATC---
SEQ ID NO:3  (1701) CATTTAA
```

Figure 8 (3/3)

The sequence identity between the DNA from different strains are analyzed and summarized in the table below.

| SEQ ID NO: | 1 | 3 | 7 | 9 | 11 | 13 |
|---|---|---|---|---|---|---|
| 1 | 100 | 74.2% | 73.1% | 72.7% | 71.6% | 74.1% |
| 3 | | 100 | 97.2% | 96.7% | 87.6% | 96.1% |
| 7 | | | 100 | 95.0% | 87.3% | 95.6% |
| 9 | | | | 100 | 87.1% | 94.2% |
| 11 | | | | | 100 | 87.7% |
| 13 | | | | | | 100 |

Figure 9
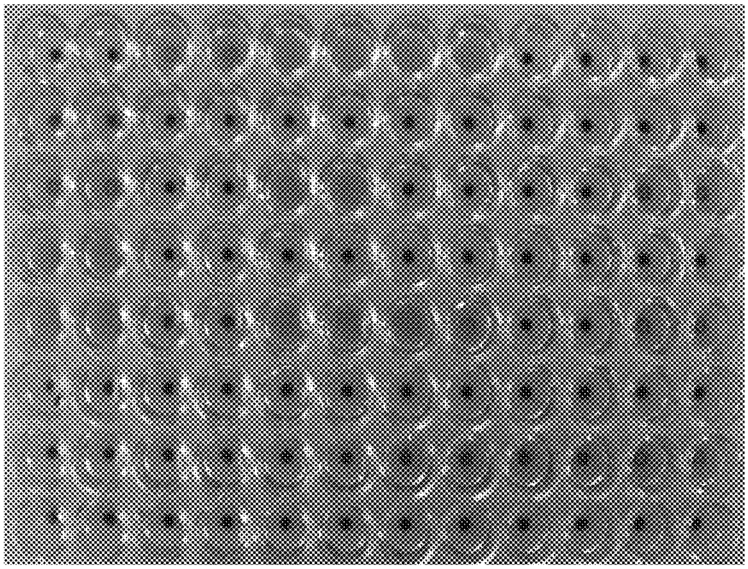
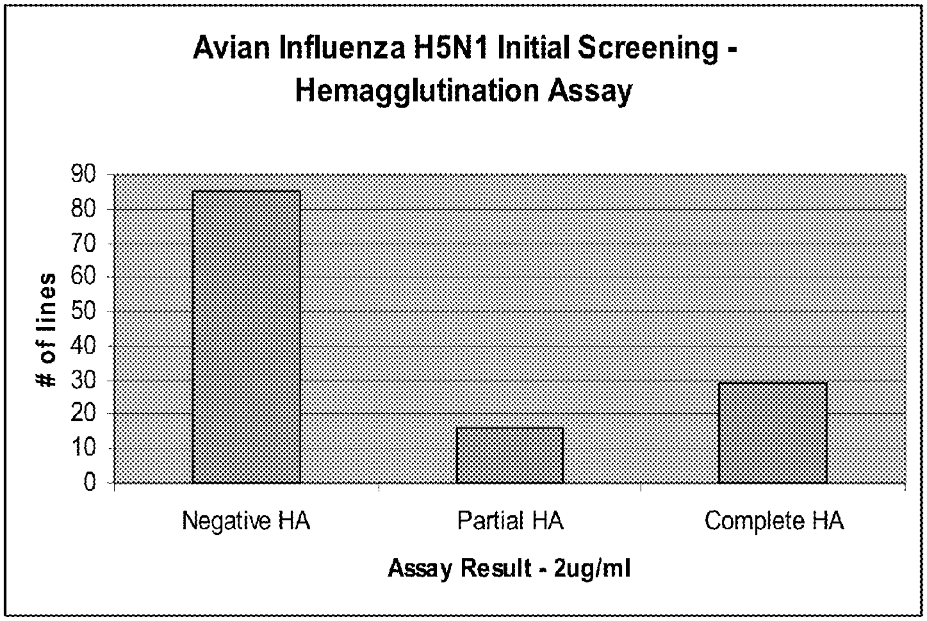

Hemagglutination Activity

-50ul samples were diluted 2-fold across the plate in duplicate
-50ul of a 10% turkey red blood cells suspension was added to all test wells

Figure 11

Estimated yield of target formulation

| | | | |
|---|---|---|---|
| Crude extract | (g biomass/ml buffer) | 0.5 | 0.5 |
| Crude extract 1x | (HAU/50μl) | 51200 | 51200 |
| Crude extract 1x | (HAU/ml) | 1024000 | 1024000 |
| Formulation | (HAU/dose) | 655 | 6550 |
| Minimum formulation dose | | 800 | 800 |
| HAU/800 doses | | 524000 | 5240000 |
| **Volume 1x per dose** | **(ml)** | **0.0006** | **0.006** |
| **Wt biomass per dose** | **(g)** | **0.0003** | **0.003** |
| **Volume 1x per 800 doses** | **(ml)** | **0.51** | **5.12** |
| **Wt biomass per 800 doses** | **(g)** | **0.26** | **2.56** |

Hemagglutination Inhibition Assay with Rockland mAB

1:100   1:2  mAB dilution →

| H5N1 Indo/7/03 inactivated virus | | | | | |
|---|---|---|---|---|---|
| Rec. H5N1 HA Ag | | | | | |
| Biolex H5N1 HA Ag | | | | | |
| Biolex wild type Ag | | | | | |
| Antigen only control | H5N1 Indo/7/03 HA | Rec. H5N1 | Biolex H5N1 HA | Biolex wild type | |

Hemagglutination Inhibition Assay with Anti-H5N1 Chicken Serum

| | 1:10 1:2 Ab dilution → | | | | | |
|---|---|---|---|---|---|---|
| H5N1 Indo/7/03 inactivated virus | | | | | | |
| Rec. H5N1 HA Ag | | | | | | |
| Biolex H5N1 HA Ag | | | | | | |
| Biolex wild type Ag | | | | | | |
| Antigen only control | | | | | | |
| | H5N1 Indo/7/03 HA | Rec. H5N1 HA | Biolex H5N1 HA | Biolex wild type | PBS | |

Hemagglutination Inhibition Assay with FP2211 Chicken Serum

| | |
|---|---|
| H5N1 Indo/7/03 inactivated virus |  |
| Rec. H5N1 HA Ag | |
| Biolex H5N1 HA Ag | |
| Biolex wild type Ag | |
| Antigen only control | |

| | | | | | | |
|---|---|---|---|---|---|---|
| | H5N1 Indo/7/03 | Rec. H5N1 HA | Biolex H5N1 HA | Biolex wild type | PBS | |

Figure 15 (1/2)
(A)
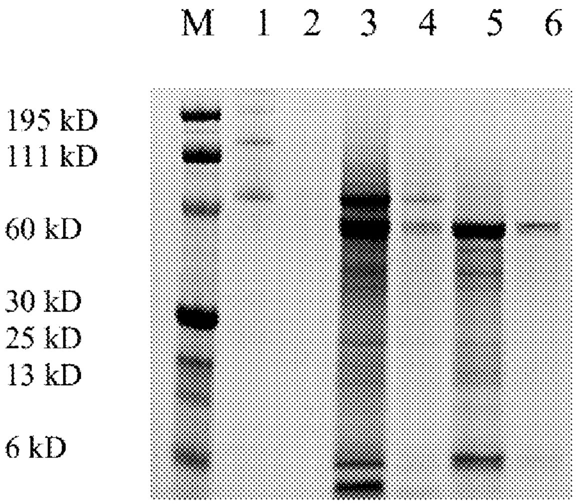
(B)
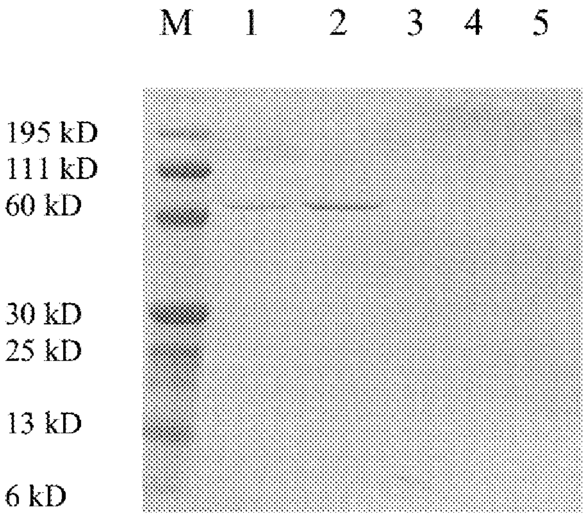

1 – Bio-Rad Kaleidoscope MW Standard - 8μL
2 – Rec. HA (1.3μg) – non-reduced – 15μL
3 – Biolex MerB H5N1 HA Extract – non-reduced – 15μL
4 – Biolex Wild Type – non-reduced – 15μL
5 – Biolex Wild Type – non-reduced – 15μL
6 – Biolex MerB H5N1 HA Extract – non-reduced – 15μL
7 – Rec. HA (1.3μg) – non-reduced – 15μL
8 – Bio-Rad Kaleidoscope MW Standard – 8μL Primary Antibody:
A. Monoclonal Anti-H5 HA of A/Vietnam/1203/04 Influenza Virus (Rockland)
B. Monoclonal Anti-H5N1 Ab pool of CP62 and 354/1 (CDC)
Secondary Antibody: HRP-labeled Goat Anti-Mouse – 1:2500 (Jackson Immuno)

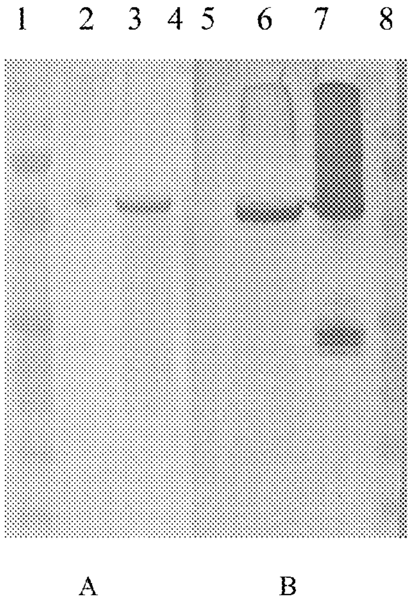

1. MW Std.
2. H5N1 ck/Indonesia/03 (mutated)
3. HA Rec. Protein
4. Biolex Wild Type Extract
5. Biolex H5N1 Extract MW Std – Bio-Rad Kaleidoscope MW Standard – 8µL
H5N1 ck/Indonesia/03 (mutated) – native, non-reduced – 15µL
HA Rec. Protein A/Vietnam/1203/2004 (Protein Sci. Corp., lot 45-05034RA-2) – native, non-reduced – 3.4µL
Biolex WT Extract (30Oct07) – native, non-reduced – 15µL
Biolex H5N1 Extract (MerB Line #76, 30 OCT 07) – native, non-reduced – 15µL

Figure 18

| Group | SPF bird age | Vaccines | Vaccination days |
|---|---|---|---|
| 1 | 3wk | *Lemna* wild type | D0/D21 |
| 2 | 3wk | *Lemna* 655 HAU | D0/D21 |
| 3 | 3wk | *Lemna* 6550 HAU | D0/D21 |
| 4 | 3wk | *Lemna* 26200 HAU | D0/D21 |
| 5 | 3wk | *Lemna* 655 HAU | D0 |
| 6 | 3wk | *Lemna* 6550 HAU | D0 |
| 7 | 3wk | *Lemna* 26200 HAU | D0 |
| 8 | Day old | TROVAC*/*Lemna* 6550 HAU | D0/D21 |

*TROVAC®-AIV H5 vaccine (Merial Select, Inc., Gainesville, GA; TROVAC is a registered trademark of Merial in the USA and elsewhere)

Figure 19

| Group | SPF bird age | Vaccines | Challenge | Mortality | Viral shedding[1] (EID50) | | NP based ELISA | |
|---|---|---|---|---|---|---|---|---|
| | | | Virus | MDT [2](days) | 2 dpc[3] | 4dpc | Pre-C | Post-C |
| 1 | 3wk | Lemna WT | Indo/03[4] | 20/20[5](2.1) | 10/10 (6.9) | | | |
| 2 | 3wk | Lemna 655HAU | Indo/03 | 0/20(-) | 4/10 (<3.1) | 0/10(<2.8) | | |
| 3 | 3wk | Lemna 6550HAU | Indo/03 | 0/10(-) | 1/10 (<2.9) | 0/10(<2.8) | | |
| 4 | 3wk | Experimental recombinant HA | PWT/06[6] | 10/10(2.2) | 10/10 (7.1) | | | |
| 5 | 3wk | Lemna 6550HAU | PWT/06 | 1/10($10^7$) | 1/10 (<3.6) | 2/10(<3.8) | 0/10 | 9/9 |
| 6 | 3wk | Lemna 26200HAU | PWT/06 | 2/10(5) | 2/10 (<3.8) | 2/10(<4.1) | 0/10 | 8/8 |
| 7 | Day old | TROVAC/Lemna 6550HAU | PWT/06 | 0/20(-) | 1/10 (<3.6) | 0/10(<3.5) | 0/10 | 8/10 |

Figure 20 (1/2)
(A)
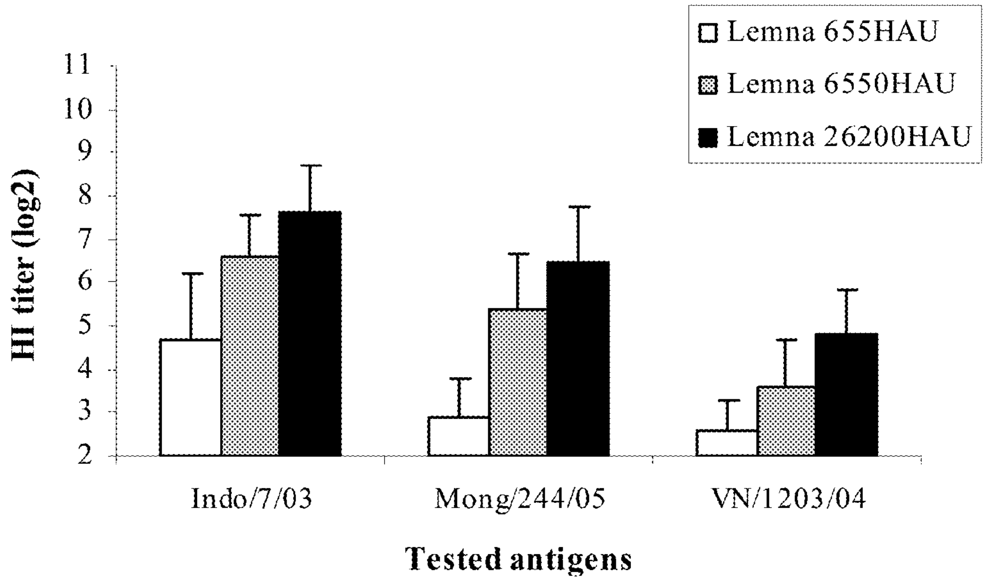
(B)
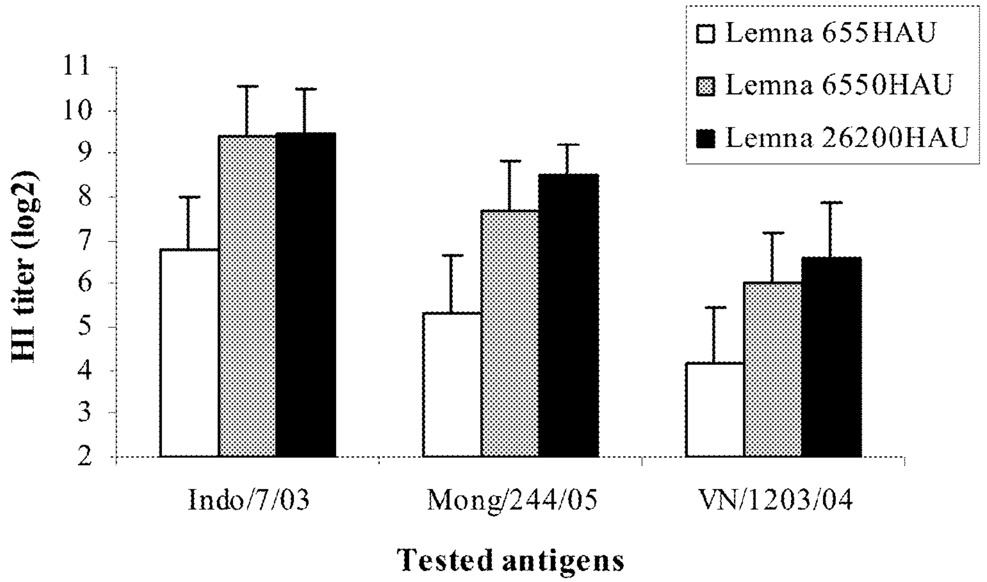

Figure 20 (2/2)
(C)
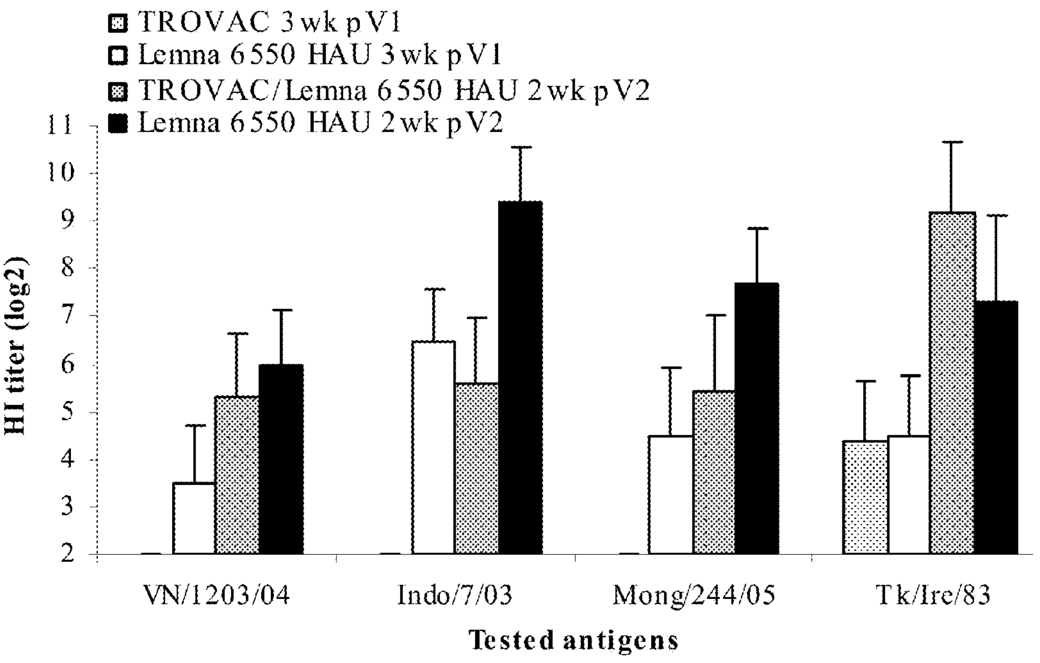

Figure 21

Table summarizing the number of positive serums/total and the mean HI titers (expressed in Log2) against various H5 antigens obtained after vaccination of chickens with different formulations before (Pre-C; D42) and after (Post-C; D56) challenge.

| Group | Vaccines | Challenge Virus | HI titer (log2) against a panel of antigens | | | | | | |
|---|---|---|---|---|---|---|---|---|---|
| | | | Ire/83[3] | VN/04[4] | Mong/05[5] | Indo/03[6] | | PWT/06[7] | |
| | | | Pre-C | Pre-C | Pre-C | Pre-C | Post-C | Pre-C | Post-C |
| 1 | *Lemna* wild type | Indo/03 | | | | 0/10[1] | | | |
| 2 | *Lemna* 655 HAU | Indo/03 | | 5/10 (2.9±1.3)[2] | 6/10 (3.0±1.1) | 9/10 (4.5±1.4) | 10/10 (7.1±1.4) | 0/10 | 6/10 (2.7±0.7) |
| 3 | *Lemna* 6550 HAU | Indo/03 | 10/10 (5.6±1.0) | 10/10 (4.2±0.8) | 10/10 (4.9±1.4) | 10/10 (6.9±1.0) | 10/10 (8.2±0.8) | 2/10 (2.2±0.4) | 8/10 (3.8±1.5) |
| 4 | *Lemna* HA biomass | Indo/03 | | | | 0/10 | | | |
| 5 | Recombinant HA 5000 HAU | PWT/06 | | 3/10 (2.4±0.7) | | | | | |
| 6 | *Lemna* 6550HAU | PWT/06 | | | | | 9/9 (8.6±1.0) | | 9/9 (6.0±1.8) |
| 7 | *Lemna* 26200HAU | PWT/06 | | 10/10 (4.1±1.1) | 10/10 (5.3±1.2) | 10/10 (6.8±0.8) | 8/8 (9.0±1.2) | 2/10 (2.2±0.4) | 8/8 (6.3±1.5) |
| 8 | TROVAC®/ *Lemna* 6550HAU | PWT/06 | 10/10 (11.0±1.2) | 10/10 (7.0±1.1) | 10/10 (6.8±1.2) | 10/10 (7.1±1.4) | 10/10 (7.7±0.9) | 5/10 (7.7±0.9) | 10/10 (4.9±1.7) |

[1] Number of positive/total number
[2] Mean HI titer (log2)± standard deviation
[3] H5N8 A/turkey/Ireland/1378/1983
[4] H5N1 A/Vietnam/1203/2004
[5] H5N1 A/Whooper swan/Mongolia/244/2005
[6] H5N1 A/chicken/Indonesia/7/2003
[7] H5N1 A/chicken/West Java/PWT-WIJ/2006

SEQUENCE LISTING

<160> NUMBER OF SEQ ID NOS: 18

<210> SEQ ID NO 1
<211> LENGTH: 1644
<212> TYPE: DNA
<213> ORGANISM: artificial
<220> FEATURE:
<223> OTHER INFORMATION: codon-optimized

<400> SEQUENCE: 1

```
gaccagatct gcatcggcta ccacgccaac aattccaccg agcaggtgga cacgatcatg     60
gaaaagaacg tgaccgtcac ccacgcccag gacatcctcg agaagacgca caacgggaag    120
ctctgcgacc tcgacggcgt gaagccgctc atcctccgcg actgctccgt ggccggctgg    180
ctcctgggca accccatgtg cgacgagttc atcaacgtcc cggagtggtc ctacatcgtg    240
gagaaggcca accccgccaa cgatctgtgc tacccgggga acctcaacga ctacgaggaa    300
ctcaagcacc tgctctcccg catcaaccac ttcgagaaga tccagatcat cccgaagtcc    360
agctggtccg accacgaggc gtccagcggc gtcagctccg cctgcccgta ccaaggcaag    420
tccagcttct tccggaacgt cgtgtggctg atcaagaaga actcggccta ccccaccatc    480
aagaggagct acaacaatac gaaccaggag gacctgctcg tgctgtgggg gatccaccac    540
ccgaacgacg cggccgagca gacccgcctg taccagaacc ccaccacgta catctccgtc    600
gggaccagca cgctcaacca gcgcctggtg ccgaagatcg ccatccgcag caaggtgaac    660
gggcagtcgg gtcgcatgga gttcttctgg acgatcctga agcccaacga cgccatcaac    720
ttcgagagca acggcaactt catcgccccg gagtacgcgt acaagatcgt caagaagggg    780
gacagcgcca tcatgaagtc ggagctggag tacgggaact gtaacacgaa gtgccagacc    840
cccatgggcg cgatcaactc cagcatgccc ttccacaaca tccaccccgct caccatcggc    900
gagtgcccca agtacgtcaa gagcaacagg ctggtcctgg ccacgggcct ccgcaacagc    960
ccccagcggg agacccgcgg gctcttcggg gccatcgcgg ggttcatcga gggcgggtgg   1020
cagggcatgg tggacggttg gtacggctac caccacagca acgagcaggg ctcgggctac   1080
gccgcggaca aggagtccac ccagaaggcc atcgacggcg tgaccaacaa ggtgaactcc   1140
atcatcgaca agatgaacac ccagttcgag gccgtcgggc gcgagttcaa caacctggag   1200
cgccggatcg agaacctcaa caagaagatg gaggacgggt tcctggacgt gtggacctac   1260
aacgcggagc tgctcgtgct catggagaac gagaggacgc tcgacttcca cgactccaac   1320
gtcaagaacc tgtacgacaa ggtccggctg cagctccggg acaacgccaa ggagctgggc   1380
aacggctgct tcgagttcta ccacaagtgc gacaacgagt gcatggagtc catcaggaac   1440
ggcacgtaca actaccccca gtattccgag gaggctcgcc tcaagaggga ggagatcagc   1500
ggcgtcaagc tcgagtccat cgggacctac cagatcctct ccatctactc cacggtggcg   1560
tccagcctcg ccctcgccat catgatggct ggcctgtcgc tgtggatgtg ctccaacggg   1620
agcctccagt gccgcatctg catc                                          1644
```

<210> SEQ ID NO 2
<211> LENGTH: 548
<212> TYPE: PRT
<213> ORGANISM: artificial
<220> FEATURE:
<223> OTHER INFORMATION: translation of codon-optimized H5N1 gene

<400> SEQUENCE: 2

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Leu Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Lys Ser Ser Phe Phe
    130                 135                 140

Arg Asn Val Val Trp Leu Ile Lys Lys Asn Ser Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Ile Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430
```

```
Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Ile Arg Asn
465                 470                 475                 480

Gly Thr Tyr Asn Tyr Pro Gln Tyr Ser Glu Glu Ala Arg Leu Lys Arg
                485                 490                 495

Glu Glu Ile Ser Gly Val Lys Leu Glu Ser Ile Gly Thr Tyr Gln Ile
            500                 505                 510

Leu Ser Ile Tyr Ser Thr Val Ala Ser Ser Leu Ala Leu Ala Ile Met
        515                 520                 525

Met Ala Gly Leu Ser Leu Trp Met Cys Ser Asn Gly Ser Leu Gln Cys
    530                 535                 540

Arg Ile Cys Ile
545

<210> SEQ ID NO 3
<211> LENGTH: 1707
<212> TYPE: DNA
<213> ORGANISM: artificial
<220> FEATURE:
<223> OTHER INFORMATION: Chicken/Indonesia/7/2003

<400> SEQUENCE: 3
atggagaaaa tagtgcttct tcttgcaata gtcagtcttg ttaaaagtga tcagatttgc      60
attggttacc atgcaaacaa ttcaacagag caggttgaca caataatgga aaagaacgtt     120
actgttacac atgcccaaga catactggaa aagacacaca acgggaagct ctgcgatcta     180
gatggagtga agcctctaat tttaagagat tgtagtgtag ctggatggct cctcgggaat     240
ccaatgtgtg acgaattcat caatgtaccg gaatggtctt acatagtgga gaaggccaat     300
ccagccaatg acctctgtta cccagggaat ctcaacgact atgaagaact aaaacaccta     360
ttgagcagaa taaaccattt tgagaaaatt cagatcatcc ccaaaagttc ttggtccgat     420
catgaagcct catcaggggt gagctcagca tgtccatacc agggaaagtc ctcctttttt     480
agaaatgtgg tatggcttat caaaaagaac agtgcatacc caacaataaa gagaagctac     540
aataatacca accaagaaga tcttttggta ctgtggggga ttcaccatcc taatgatgcg     600
gcagagcaga caaggctata tcaaaaccca accacctata tttccgttgg gacatcaaca     660
ctaaaccaga gattggtacc aaaaatagct attagatcca aagtaaacgg gcaaagtgga     720
agaatggagt tcttctggac aattttaaaa ccgaatgatg caatcaactt cgagagtaat     780
ggaaatttca ttgctccaga atatgcatac aaaattgtca agaaagggga ctctgcaatt     840
atgaaaagtg aattggaata tggtaactgc aacaccaagt gtcaaactcc aatgggggcg     900
ataaactcta gtatgccatt ccacaacata caccctctca ccatcgggga atgccccaaa     960
tatgtgaaat caaacagatt agtccttgcg actgggctca gaaatagccc tcaaagagag    1020
agaagaagaa aaaagagagg actatttgga gctatagcag gttttataga gggaggatgg    1080
cagggaatgg tagatggttg gtatgggtac caccatagca atgagcaggg gagtgggtac    1140
gctgcagaca aagaatccac tcaaaaggca atagatgggg tcaccaataa ggtcaactcg    1200
atcattgaca aaatgaacac tcagtttgag gccgttggaa gggaatttaa taacttagaa    1260
aggagaatag agaatttaaa caagaagatg gaagacggat tcctagatgt ctggacttat    1320
aatgctgaac ttctggttct catggaaaat gagagaactc tagactttca tgactcaaat    1380
```

-continued

```
gttaagaacc tctacgacaa ggtccgacta cagcttaggg ataatgcaaa ggagctgggt   1440

aacggttgtt tcgagttcta tcacaaatgt gataatgaat gtatggaaag tataagaaac   1500

ggaacgtata actacccgca gtattcagaa gaagcaagat taaaaagaga agaaataagt   1560

ggagtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaa                                       1707
```

```
<210> SEQ ID NO 4
<211> LENGTH: 564
<212> TYPE: PRT
<213> ORGANISM: artificial
<220> FEATURE:
<223> OTHER INFORMATION: Chicken/Indonesia/7/2003(mutated)

<400> SEQUENCE: 4

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Ile Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300
```

```
Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Leu Trp Met Cys Ser Asn Gly Ser Leu Gln Cys
545                 550                 555                 560

Arg Ile Cys Ile


<210> SEQ ID NO 5
<211> LENGTH: 568
<212> TYPE: PRT
<213> ORGANISM: artificial
<220> FEATURE:
<223> OTHER INFORMATION: Chicken/Indonesia/7/2003 (wildtype)

<400> SEQUENCE: 5

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Leu Asn
            100                 105                 110
```

-continued

```
Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Ile Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
```

```
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565


<210> SEQ ID NO 6
<211> LENGTH: 14855
<212> TYPE: DNA
<213> ORGANISM: artificial
<220> FEATURE:
<223> OTHER INFORMATION: plasmid construct

<400> SEQUENCE: 6

aattcaccat gcaggtcctg aacacgatgg tcaacaagca cttcctctcc ctgtccgtcc      60

tcatcgtcct cctcgggctg agcagcaacc tcaccgccgg cgaccagatc tgcatcggct     120

accacgccaa caattccacc gagcaggtgg acacgatcat ggaaaagaac gtgaccgtca     180

cccacgccca ggacatcctc gagaagacgc acaacgggaa gctctgcgac ctcgacggcg     240

tgaagccgct catcctccgc gactgctccg tggccggctg gctcctgggc aaccccatgt     300

gcgacgagtt catcaacgtc ccggagtggt cctacatcgt ggagaaggcc aaccccgcca     360

acgatctgtg ctacccgggg aacctcaacg actacgagga actcaagcac ctgctctccc     420

gcatcaacca cttcgagaag atccagatca tcccgaagtc cagctggtcc gaccacgagg     480

cgtccagcgg cgtcagctcc gcctgcccgt accaaggcaa gtccagcttc ttccggaacg     540

tcgtgtggct gatcaagaag aactcggcct accccaccat caagaggagc tacaacaata     600

cgaaccagga ggacctgctc gtgctgtggg ggatccacca cccgaacgac gcggccgagc     660

agacccgcct gtaccagaac cccaccacgt acatctccgt cgggaccagc acgctcaacc     720

agcgcctggt gccgaagatc gccatccgca gcaaggtgaa cgggcagtcg ggtcgcatgg     780

agttcttctg gacgatcctg aagcccaacg acgccatcaa cttcgagagc aacggcaact     840

tcatcgcccc ggagtacgcg tacaagatcg tcaagaaggg ggacagcgcc atcatgaagt     900

cggagctgga gtacgggaac tgtaacacga agtgccagac ccccatgggc gcgatcaact     960

ccagcatgcc cttccacaac atccacccgc tcaccatcgg cgagtgcccc aagtacgtca    1020

agagcaacag gctggtcctg gccacgggcc tccgcaacag cccccagcgg gagacccgcg    1080

ggctcttcgg ggccatcgcg gggttcatcg agggcgggtg gcagggcatg gtggacggtt    1140

ggtacggcta ccaccacagc aacgagcagg gctcgggcta cgccgcggac aaggagtcca    1200

cccagaaggc catcgacggc gtgaccaaca aggtgaactc catcatcgac aagatgaaca    1260

cccagttcga ggccgtcggg cgcgagttca acaacctgga gcgccggatc gagaacctca    1320

acaagaagat ggaggacggg ttcctggacg tgtggaccta caacgcggag ctgctcgtgc    1380

tcatggagaa cgagaggacg ctcgacttcc acgactccaa cgtcaagaac ctgtacgaca    1440

aggtccggct gcagctccgg gacaacgcca aggagctggg caacggctgc ttcgagttct    1500

accacaagtg cgacaacgag tgcatggagt ccatcaggaa cggcacgtac aactaccccc    1560

agtattccga ggaggctcgc ctcaagaggg aggagatcag cggcgtcaag ctcgagtcca    1620

tcgggaccta ccagatcctc tccatctact ccacggtggc gtccagcctc gccctcgcca    1680

tcatgatggc tggcctgtcg ctgtggatgt gctccaacgg gagcctccag tgccgcatct    1740

gcatctaaga gctcgaattt ccccgatcgt tcaaacattt ggcaataaag tttcttaaga    1800

ttgaatcctg ttgccggtct tgcgatgatt atcatataat ttctgttgaa ttacgttaag    1860
```

-continued

```
catgtaataa ttaacatgta atgcatgacg ttatttatga gatgggtttt tatgattaga   1920
gtcccgcaat tatacattta atacgcgata gaaaacaaaa tatagcgcgc aaactaggat   1980
aaattatcgc gcgcggtgtc atctatgtta ctagatcggg aattaattca gatcggctga   2040
gtggctcctt caacgttgcg gttctgtcag ttccaaacgt aaaacggctt gtcccgcgtc   2100
atcggcgggg gtcataacgt gactccctta attctccgct catgatcaga ttgtcgtttc   2160
ccgccttcag tttaaactat cagtgtttga caggatatat tggcgggtaa acctaagaga   2220
aaagagcgtt tattagaata atcggatatt taaaagggcg tgaaaaggtt tatccgttcg   2280
tccatttgta tgtgcatgcc aaccacaggg ttccccagat ctggcgccgg ccagcgagac   2340
gagcaagatt ggccgccgcc cgaaacgatc cgacagcgcg cccagcacag gtgcgcaggc   2400
aaattgcacc aacgcataca gcgccagcag aatgccatag tgggcggtga cgtcgttcga   2460
gtgaaccaga tcgcgcagga ggcccggcag caccggcata atcaggccga tgccgacagc   2520
gtcgagcgcg acagtgctca gaattacgat caggggtatg ttgggtttca cgtctggcct   2580
ccggaccagc ctccgctggt ccgattgaac gcgcggattc tttatcactg ataagttggt   2640
ggacatatta tgtttatcag tgataaagtg tcaagcatga caaagttgca gccgaataca   2700
gtgatccgtg ccgccctgga cctgttgaac gaggtcggcg tagacggtct gacgacacgc   2760
aaactggcgg aacggttggg ggttcagcag ccggcgcttt actggcactt caggaacaag   2820
cgggcgctgc tcgacgcact ggccgaagcc atgctggcgg agaatcatac gcattcggtg   2880
ccgagagccg acgacgactg gcgctcattt ctgatcggga atgcccgcag cttcaggcag   2940
gcgctgctcg cctaccgcga tggcgcgcgc atccatgccg gcacgcgacc gggcgcaccg   3000
cagatggaaa cggccgacgc gcagcttcgc ttcctctgcg aggcgggttt ttcggccggg   3060
gacgccgtca atgcgctgat gacaatcagc tacttcactg ttggggccgt gcttgaggag   3120
caggccggcg acagcgatgc cggcgagcgc ggcggcaccg ttgaacaggc tccgctctcg   3180
ccgctgttgc gggccgcgat agacgccttc gacgaagccg gtccggacgc agcgttcgag   3240
cagggactcg cggtgattgt cgatggattg gcgaaaagga ggctcgttgt caggaacgtt   3300
gaaggaccga gaaagggtga cgattgatca ggaccgctgc cggagcgcaa cccactcact   3360
acagcagagc catgtagaca acatcccctc cccctttcca ccgcgtcaga cgcccgtagc   3420
agcccgctac gggctttttc atgccctgcc ctagcgtcca agcctcacgg ccgcgctcgg   3480
cctctctggc ggccttctgg cgctcttccg cttcctcgct cactgactcg ctgcgctcgg   3540
tcgttcggct gcggcgagcg gtatcagctc actcaaaggc ggtaatacgg ttatccacag   3600
aatcagggga taacgcagga aagaacatgt gagcaaaagg ccagcaaaag gccaggaacc   3660
gtaaaaaggc cgcgttgctg gcgtttttcc ataggctccg cccccctgac gagcatcaca   3720
aaaatcgacg ctcaagtcag aggtggcgaa acccgacagg actataaaga taccaggcgt   3780
ttccccctgg aagctccctc gtgcgctctc ctgttccgac cctgccgctt accggatacc   3840
tgtccgcctt tctcccttcg ggaagcgtgg cgcttttccg ctgcataacc ctgcttcggg   3900
gtcattatag cgatttttttc ggtatatcca tcctttttcg cacgatatac aggattttgc   3960
caaagggttc gtgtagactt tccttggtgt atccaacggc gtcagccggg caggataggt   4020
gaagtaggcc cacccgcgag cgggtgttcc ttcttcactg tcccttattc gcacctggcg   4080
gtgctcaacg ggaatcctgc tctgcgaggc tggccggcta ccgccggcgt aacagatgag   4140
ggcaagcgga tggctgatga aaccaagcca accaggaagg gcagcccacc tatcaaggtg   4200
tactgccttc cagacgaacg aagagcgatt gaggaaaagg cggcggcggc cggcatgagc   4260
```

-continued

```
ctgtcggcct acctgctggc cgtcggccag ggctacaaaa tcacgggcgt cgtggactat   4320
gagcacgtcc gcgagctggc ccgcatcaat ggcgacctgg gccgcctggg cggcctgctg   4380
aaactctggc tcaccgacga cccgcgcacg gcgcggttcg gtgatgccac gatcctcgcc   4440
ctgctggcga agatcgaaga gaagcaggac gagcttggca aggtcatgat gggcgtggtc   4500
cgcccgaggg cagagccatg actttttag ccgctaaaac ggccgggggg tgcgcgtgat   4560
tgccaagcac gtccccatgc gctccatcaa gaagagcgac ttcgcggagc tggtgaagta   4620
catcaccgac gagcaaggca agaccgagcg cctttgcgac gctcaccggg ctggttgccc   4680
tcgccgctgg gctggcggcc gtctatggcc ctgcaaacgc gccagaaacg ccgtcgaagc   4740
cgtgtgcgag acaccgcggc cgccggcgtt gtggatacct cgcggaaaac ttggccctca   4800
ctgacagatg aggggcggac gttgacactt gaggggccga ctcacccggc gcggcgttga   4860
cagatgaggg gcaggctcga tttcggccgg cgacgtggag ctggccagcc tcgcaaatcg   4920
gcgaaaacgc ctgattttac gcgagtttcc cacagatgat gtggacaagc ctggggataa   4980
gtgccctgcg gtattgacac ttgaggggcg cgactactga cagatgaggg gcgcgatcct   5040
tgacacttga ggggcagagt gctgacagat gaggggcgca cctattgaca tttgaggggc   5100
tgtccacagg cagaaaatcc agcatttgca agggtttccg cccgtttttc ggccaccgct   5160
aacctgtctt ttaacctgct tttaaaccaa tatttataaa ccttgttttt aaccagggct   5220
gcgccctgtg cgcgtgaccg cgcacgccga aggggggtgc ccccccttct cgaaccctcc   5280
cggcccgcta acgcgggcct cccatccccc caggggctgc gcccctcggc cgcgaacggc   5340
ctcaccccaa aaatggcagc gctggcagtc cttgccattg ccgggatcgg ggcagtaacg   5400
ggatgggcga tcagcccgag cgcgacgccc ggaagcattg acgtgccgca ggtgctggca   5460
tcgacattca gcgaccaggt gccgggcagt gagggcggcg gcctgggtgg cggcctgccc   5520
ttcacttcgg ccgtcggggc attcacggac ttcatggcgg ggccggcaat ttttaccttg   5580
ggcattcttg gcatagtggt cgcgggtgcc gtgctcgtgt tcgggggtgc gataaaccca   5640
gcgaaccatt tgaggtgata ggtaagatta taccgaggta tgaaaacgag aattggacct   5700
ttacagaatt actctatgaa gcgccatatt taaaaagcta ccaagacgaa gaggatgaag   5760
aggatgagga ggcagattgc cttgaatata ttgacaatac tgataagata atatatcttt   5820
tatatagaag atatcgccgt atgtaaggat ttcagggggc aaggcatagg cagcgcgctt   5880
atcaatatat ctatagaatg ggcaaagcat aaaaacttgc atggactaat gcttgaaacc   5940
caggacaata accttatagc ttgtaaattc tatcataatt gggtaatgac tccaacttat   6000
tgatagtgtt ttatgttcag ataatgcccg atgactttgt catgcagctc caccgatttt   6060
gagaacgaca gcgacttccg tcccagccgt gccaggtgct gcctcagatt caggttatgc   6120
cgctcaattc gctgcgtata tcgcttgctg attacgtgca gctttccctt caggcgggat   6180
tcatacagcg gccagccatc cgtcatccat atcaccacgt caaagggtga cagcaggctc   6240
ataagacgcc ccagcgtcgc catagtgcgt tcaccgaata cgtgcgcaac aaccgtcttc   6300
cggagactgt catacgcgta aaacagccag cgctggcgcg atttagcccc gacatagccc   6360
cactgttcgt ccatttccgc gcagacgatg acgtcactgc ccggctgtat gcgcgaggtt   6420
accgactgcg gcctgagttt tttaagtgac gtaaaatcgt gttgaggcca acgcccataa   6480
tgcgggctgt tgcccggcat ccaacgccat tcatggccat atcaatgatt ttctggtgcg   6540
taccgggttg agaagcggtg taagtgaact gcagttgcca tgttttacgg cagtgagagc   6600
agagatagcg ctgatgtccg gcggtgcttt tgccgttacg caccaccccg tcagtagctg   6660
```

-continued

```
aacaggaggg acagctgata gacacagaag ccactggagc acctcaaaaa caccatcata   6720
cactaaatca gtaagttggc agcatcaccc ataattgtgg tttcaaaatc ggctccgtcg   6780
atactatgtt atacgccaac tttgaaaaca actttgaaaa agctgttttc tggtatttaa   6840
ggttttagaa tgcaaggaac agtgaattgg agttcgtctt gttataatta gcttcttggg   6900
gtatctttaa atactgtaga aaagaggaag gaaataataa atggctaaaa tgagaatatc   6960
accggaattg aaaaaactga tcgaaaaata ccgctgcgta aaagatacgg aaggaatgtc   7020
tcctgctaag gtatataagc tggtgggaga aaatgaaaac ctatatttaa aaatgacgga   7080
cagccggtat aaagggacca cctatgatgt ggaacgggaa aaggacatga tgctatggct   7140
ggaaggaaag ctgcctgttc caaaggtcct gcactttgaa cggcatgatg gctggagcaa   7200
tctgctcatg agtgaggccg atggcgtcct ttgctcggaa gagtatgaag atgaacaaag   7260
ccctgaaaag attatcgagc tgtatgcgga gtgcatcagg ctctttcact ccatcgacat   7320
atcggattgt ccctatacga atagcttaga cagccgctta gccgaattgg attacttact   7380
gaataacgat ctggccgatg tggattgcga aaactgggaa gaagacactc catttaaaga   7440
tccgcgcgag ctgtatgatt ttttaaagac ggaaaagccc gaagaggaac ttgtcttttc   7500
ccacggcgac ctgggagaca gcaacatctt tgtgaaagat ggcaaagtaa gtggctttat   7560
tgatcttggg agaagcggca gggcggacaa gtggtatgac attgccttct gcgtccggtc   7620
gatcagggag gatatcgggg aagaacagta tgtcgagcta ttttttgact tactggggat   7680
caagcctgat tgggagaaaa taaaatatta tattttactg gatgaattgt tttagtacct   7740
agatgtggcg caacgatgcc ggcgacaagc aggagcgcac cgacttcttc cgcatcaagt   7800
gttttggctc tcaggccgag gcccacggca agtatttggg caaggggtcg ctggtattcg   7860
tgcagggcaa gattcggaat accaagtacg agaaggacgg ccagacggtc tacgggaccg   7920
acttcattgc cgataaggtg gattatctgg acaccaaggc accaggcggg tcaaatcagg   7980
aataagggca cattgccccg gcgtgagtcg gggcaatccc gcaaggaggg tgaatgaatc   8040
ggacgtttga ccggaaggca tacaggcaag aactgatcga cgcggggttt tccgccgagg   8100
atgccgaaac catcgcaagc cgcaccgtca tgcgtgcgcc ccgcgaaacc ttccagtccg   8160
tcggctcgat ggtccagcaa gctacggcca agatcgagcg cgacagcgtg caactggctc   8220
cccctgccct gcccgcgcca tcggccgccg tggagcgttc gcgtcgtctc gaacaggagg   8280
cggcaggttt ggcgaagtcg atgaccatcg acacgcgagg aactatgacg accaagaagc   8340
gaaaaaccgc cggcgaggac ctggcaaaac aggtcagcga ggccaagcag gccgcgttgc   8400
tgaaacacac gaagcagcag atcaaggaaa tgcagctttc cttgttcgat attgcgccgt   8460
ggccggacac gatgcgagcg atgccaaacg acacggcccg ctctgccctg ttcaccacgc   8520
gcaacaagaa aatcccgcgc gaggcgctgc aaaacaaggt cattttccac gtcaacaagg   8580
acgtgaagat cacctacacc ggcgtcgagc tgcgggccga cgatgacgaa ctggtgtggc   8640
agcaggtgtt ggagtacgcg aagcgcaccc ctatcggcga gccgatcacc ttcacgttct   8700
acgagctttg ccaggacctg ggctggtcga tcaatggccg gtattacacg aaggccgagg   8760
aatgcctgtc gcgcctacag gcgacggcga tgggcttcac gtccgaccgc gttgggcacc   8820
tggaatcggt gtcgctgctg caccgcttcc gcgtcctgga ccgtggcaag aaaacgtccc   8880
gttgccaggt cctgatcgac gaggaaatcg tcgtgctgtt tgctggcgac cactacacga   8940
aattcatatg ggagaagtac cgcaagctgt cgccgacggc ccgacggatg ttcgactatt   9000
tcagctcgca ccgggagccg tacccgctca agctggaaac cttccgcctc atgtgcggat   9060
```

-continued

```
cggattccac ccgcgtgaag aagtggcgcg agcaggtcgg cgaagcctgc gaagagttgc   9120
gaggcagcgg cctggtggaa cacgcctggg tcaatgatga cctggtgcat tgcaaacgct   9180
agggccttgt ggggtcagtt ccggctgggg gttcagcagc cagcgcttta ctggcatttc   9240
aggaacaagc gggcactgct cgacgcactt gcttcgctca gtatcgctcg ggacgcacgg   9300
cgcgctctac gaactgccga taaacagagg attaaaattg acaattgtga ttaaggctca   9360
gattcgacgg cttggagcgg ccgacgtgca ggatttccgc gagatccgat tgtcggccct   9420
gaagaaagct ccagagatgt tcgggtccgt ttacgagcac gaggagaaaa agcccatgga   9480
ggcgttcgct gaacggttgc gagatgccgt ggcattcggc gcctacatcg acggcgagat   9540
cattgggctg tcggtcttca aacaggagga cggccccaag gacgctcaca aggcgcatct   9600
gtccggcgtt ttcgtggagc ccgaacagcg aggccgaggg gtcgccggta tgctgctgcg   9660
ggcgttgccg gcgggtttat tgctcgtgat gatcgtccga cagattccaa cgggaatctg   9720
gtggatgcgc atcttcatcc tcggcgcact taatatttcg ctattctgga gcttgttgtt   9780
tatttcggtc taccgcctgc cgggcggggt cgcggcgacg gtaggcgctg tgcagccgct   9840
gatggtcgtg ttcatctctg ccgctctgct aggtagcccg atacgattga tggcggtcct   9900
gggggctatt tgcggaactg cgggcgtggc gctgttggtg ttgacaccaa acgcagcgct   9960
agatcctgtc ggcgtcgcag cgggcctggc gggggcggtt tccatggcgt tcggaaccgt  10020
gctgacccgc aagtggcaac ctcccgtgcc tctgctcacc tttaccgcct ggcaactggc  10080
ggccggagga cttctgctcg ttccagtagc tttagtgttt gatccgccaa tcccgatgcc  10140
tacaggaacc aatgttctcg gcctggcgtg gctcggcctg atcggagcgg gtttaaccta  10200
cttcctttgg ttccgggga tctcgcgact cgaacctaca gttgtttcct tactgggctt  10260
tctcagcccc agatctgggg tcgatcagcc ggggatgcat caggccgaca gtcggaactt  10320
cgggtccccg acctgtacca ttcggtgagc aatggatagg ggagttgata tcgtcaacgt  10380
tcacttctaa agaaatagcg ccactcagct tcctcagcgg ctttatccag cgatttccta  10440
ttatgtcggc atagttctca agatcgacag cctgtcacgg ttaagcgaga aatgaataag  10500
aaggctgata attcggatct ctgcgaggga gatgatattt gatcacaggc agcaacgctc  10560
tgtcatcgtt acaatcaaca tgctaccctc cgcgagatca tccgtgtttc aaacccggca  10620
gcttagttgc cgttcttccg aatagcatcg gtaacatgag caaagtctgc cgccttacaa  10680
cggctctccc gctgacgccg tcccggactg atgggctgcc tgtatcgagt ggtgattttg  10740
tgccgagctg ccggtcgggg agctgttggc tggctggtgg caggatatat tgtggtgtaa  10800
acaaattgac gcttagacaa cttaataaca cattgcggac gtttttaatg tactggggtg  10860
gtttttcttt tcaccagtga gacgggcaac agctgattgc ccttcaccgc ctggccctga  10920
gagagttgca gcaagcggtc cacgctggtt tgccccagca ggcgaaaatc ctgtttgatg  10980
gtggttccga aatcggcaaa atcccttata aatcaaaaga atagcccgag atagggttga  11040
gtgttgttcc agtttggaac aagagtccac tattaaagaa cgtggactcc aacgtcaaag  11100
ggcgaaaaac cgtctatcag ggcgatggcc cactacgtga accatcaccc aaatcaagtt  11160
ttttggggtc gaggtgccgt aaagcactaa atcggaaccc taaagggagc ccccgattta  11220
gagcttgacg gggaaagccg gcgaacgtgg cgagaaagga agggaagaaa gcgaaaggag  11280
cgggcgccat tcaggctgcg caactgttgg gaagggcgat cggtgcgggc ctcttcgcta  11340
ttacgccagc tggcgaaagg gggatgtgct gcaaggcgat taagttgggt aacgccaggg  11400
ttttcccagt cacgacgttg taaaacgacg gccagtgaat tgccatcttg aaagaaatat  11460
```

-continued

```
agtttaaata tttattgata aaataagtca ggtattatag tccaagcaaa aacataattt  11520
attgatgcaa agtttaaatt cagaaatatt tcaataactg attatatcag ctggtacatt  11580
gccgtagatg aaagactgag tgcgatatta tgtgtaatac ataaattgat gatatagcta  11640
gcttagctca tcgggggatc cttaatcgac tctagctaga acgaattgtt aggtggcggt  11700
acttgggtcg atatcaaagt gcatcacttc ttcccgtatg cccaactttg tatagagagc  11760
cactgcggga tcgtcaccgt aatctgcttg cacgtagatc acataagcac caagcgcgtt  11820
ggcctcatgc ttgaggagat tgatgagcgc ggtggcaatg ccctgcctcc ggtgctcgcc  11880
ggagactgcg agatcataga tatagatctc actacgcggc tgctcaaacc tgggcagaac  11940
gtaagccgcg agagcgccaa caaccgcttc ttggtcgaag gcagcaagcg cgatgaatgt  12000
cttactacgg agcaagttcc cgaggtaatc ggagtccggc tgatgttggg agtaggtggc  12060
tacgtctccg aactcacgac cgaaaagatc aagagcagcc cgcatggatt tgacttggtc  12120
agggccgagc ctacatgtgc gaatgatgcc catacttgag ccacctaact ttgttttagg  12180
gcgactgccc tgctgcgtaa catcgttgct gctgcgtacc atggagatct ggattgagag  12240
tgaatatgag actctaattg gataccgagg ggaatttatg gaagtcagtg gagcattttt  12300
gacaagaaat atttgctagc tgatagtgac cttaggcgac ttttgaacgc gcaataatgg  12360
tttctgacgt atgtgcttag ctcattaaac tccagaaacc cgcggctgag tggctccttc  12420
aacgttgcgg ttctgtcagt tccaaacgta aaacggcttg tcccgcgtca tcggcggggg  12480
tcataacgtg actcccttaa ttctccgctc atgatcttga tcccctgcgc catcagatcc  12540
ttggcggcaa gaaagccatc cagtttactt tgcagggctt cccaacctta ccagagggcg  12600
ccccagctgg caattccggt tcgcttgctg tccataaaac cgcccagtct agctatcgcc  12660
atgtaagccc actgcaagct acctgctttc tctttgcgct tgcgttttcc cttgtccaga  12720
tagcccagta gctgacattc atccggggtc agcaccgttt ctgcggactg gctttctacg  12780
tgttccgctt cctttagcag cccttgcgcc ctgagtgctt gcggcagcgt gaagctctgg  12840
acatcatgtt ggatatgaaa caactattat ttatctacat gttttagatg ttatctgatt  12900
atttttatac cgtagtcttc tattgatgag gagtctaagg ctatagaatt atatatctaa  12960
atgattaata tatatattat taataattaa caataattaa tatattataa tttatatata  13020
tatattttat attattataa taatattctt acaaatataa ttattatatt cgacggtatc  13080
gataagctcg ggatccctga aagcgacgtt ggatgttaac atctacaaat tgccttttct  13140
tatcgaccat gtacgtaagc gcttacgttt ttggtggacc cttgaggaaa ctggtagctg  13200
ttgtgggcct gtggtctcaa gatggatcat taatttccac cttcacctac gatgggggc  13260
atcgcaccgg tgagtaatat tgtacggcta agagcgaatt tggcctgtag gatccctgaa  13320
agcgacgttg gatgttaaca tctacaaatt gccttttctt atcgaccatg tacgtaagcg  13380
cttacgtttt tggtggaccc ttgaggaaac tggtagctgt tgtgggcctg tggtctcaag  13440
atggatcatt aatttccacc ttcacctacg atgggggca tcgcaccggt gagtaatatt  13500
gtacggctaa gagcgaattt ggcctgtagg atccctgaaa gcgacgttgg atgttaacat  13560
ctacaaattg ccttttctta tcgaccatgt acgtaagcgc ttacgttttt ggtggaccct  13620
tgaggaaact ggtagctgtt gtgggcctgt ggtctcaaga tggatcatta atttccacct  13680
tcacctacga tgggggcat cgcaccggtg agtaatattg tacggctaag agcgaatttg  13740
gcctgtagga tccgcgagct ggtcaatccc attgcttttg aagcagctca acattgatct  13800
ctttctcgat cgagggagat ttttcaaatc agtgcgcaag acgtgacgta agtatccgag  13860
```

-continued

```
tcagttttta tttttctact aatttggtcg tttatttcgg cgtgtaggac atggcaaccg  13920

ggcctgaatt tcgcgggtat tctgtttcta ttccaacttt ttcttgatcc gcagccatta  13980

acgacttttg aatagatacg ctgacacgcc aagcctcgct agtcaaaagt gtaccaaaca  14040

acgctttaca gcaagaacgg aatgcgcgtg acgctcgcgg tgacgccatt tcgccttttc  14100

agaaatggat aaatagcctt gcttcctatt atatcttccc ccaaattaat taagaaactc  14160

ccgaggtgag caaggatccg gagtcgagcg cgaagaagag aaagagggaa agcgcgggta  14220

ccgggccccc ccctcgacgg atcaagtgca aaggtccgcc ttgtttctcc tctgtctctt  14280

gatctgacta atcttggttt atgattcgtt gagtaatttt ggggaaagct agcttcgtcc  14340

acagtttttt tttcgatgaa cagtgccgca gtggcgctga tcttgtatgc tatcctgcaa  14400

tcgtggtgaa cttatttctt ttatatcctt cactcccatg aaaaggctag taatctttct  14460

cgatgtaaca tcgtccagca ctgctattac cgtgtggtcc atccgacagt ctggctgaac  14520

acatcatacg atattgagca aagatcgatc tatcttccct gttctttaat gaaagacgtc  14580

attttcatca gtatgatcta agaatgttgc aacttgcaag gaggcgtttc tttctttgaa  14640

tttaactaac tcgttgagtg gccctgtttc tcggacgtaa ggcctttgct gctccacaca  14700

tgtccattcg aattttaccg tgtttagcaa gggcgaaaag tttgcatctt gatgatttag  14760

cttgactatg cgattgcttt cctggacccg tgcagctgcg gacggatccc ccgctcgagg  14820

tcgacggtat cgataagctt gatcagatct gatcg                             14855


<210> SEQ ID NO 7
<211> LENGTH: 1748
<212> TYPE: DNA
<213> ORGANISM: artificial
<220> FEATURE:
<223> OTHER INFORMATION: whooper swan/Mongolia/244/2005

<400> SEQUENCE: 7

tcaatctgtc aaaatggaga aaatagtgct tcttcttgca atagtcagtc ttgttaaaag     60

tgatcagatt tgcattggtt accatgcaaa caactcgaca gagcaggttg acacaataat    120

ggaaaagaac gtcactgtta cacacgcaca agacatactg gaaaagacac acaacgggaa    180

actctgcgat ctagatggag tgaagcctct aattttaaga gattgtagtg tagctggatg    240

gctcctcggg aacccaatgt gtgacgaatt cctcaatgtg ccggaatggt cttacatagt    300

ggagaagatc aatccagcca atgacctctg ttacccaggg aatttcaacg actatgaaga    360

actgaaacac ctattgagca gaataaacca ttttgagaaa attcagatca tccccaaaag    420

ttcttggtca gatcatgaag cctcatcagg ggtgagctca gcatgtccat accagggaag    480

gtcctccttt tttagaaatg tggtatggct tatcaaaaag gacaatgcat acccaacaat    540

aaagagaagt tacaataata ccaaccaaga agatcttttg gtactgtggg ggattcacca    600

tccaaatgat gcggcagagc agacaaggct ctatcaaaac ccaaccacct atatttccgt    660

tgggacatca acactaaacc agagactggt accaaaaata gctactagat ccaaggtaaa    720

cgggcaaagt ggaaggatgg agttcttttg gacaatttta aaaccgaatg atgcaataaa    780

ctttgagagt aatggaaatt tcattgctcc agaaaatgca tacaaaattg tcaagaaagg    840

ggactcaaca attatgaaaa gtgaattgga atatggtaac tgcaacacca agtgtcaaac    900

tccaataggg gcgataaact ctagtatgcc attccacaac atccaccctc tcaccatcgg    960

ggaatgcccc aaatatgtga aatcaaacag attagtcctt gcgactgggc tcagaaatag   1020

ccctcaagga gagagaagaa gaagaaagag aggactattt ggagctatag caggttttat   1080
```

```
agagggagga tggcagggaa tggtagatgg ttggtatggg taccaccata gcaacgagca   1140

ggggagtggg tacgctgcag acaaagaatc cactcaaaag gcaatagatg gagtcaccaa   1200

taaggtcaac tcgatcattg acaaaatgaa cactcagttt gaggctgttg gaagggaatt   1260

taataactta gaaaggagaa tagaaaattt aaacaagaag atggaagacg gattcctaga   1320

tgtctggact tataatgctg aacttctggt tctcatggaa aatgagagaa ctctagactt   1380

tcatgactca aatgtcaaga acctttacga caaggtccga ctacagctta gggataatgc   1440

aaaggagctt ggtaacggtt gtttcgagtt ctatcataga tgtgataatg aatgtatgga   1500

aagtgtaaga aacggaacgt atgactaccc gcagtattca gaagaagcaa gattaaaaag   1560

agaggaaata agtggagtaa aattggaatc aataggaact taccaaatac tgtcaattta   1620

ttcaacagtg gcgagctccc tagcactggc aatcatggtg gctggtctat ctttatggat   1680

gtgctccaat ggatcgttac aatgcagaat ttgcatttaa atttgtgagt tcagattgta   1740

gttaaaaa                                                            1748
```

```
<210> SEQ ID NO 8
<211> LENGTH: 568
<212> TYPE: PRT
<213> ORGANISM: artificial
<220> FEATURE:
<223> OTHER INFORMATION: whooper swan/Mongolia/244/2005

<400> SEQUENCE: 8

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
```

-continued 245 250 255

Phe Glu Ser Asn Gly Asn Phe Ile Ala Pro Glu Asn Ala Tyr Lys Ile
260 265 270

Val Lys Lys Gly Asp Ser Thr Ile Met Lys Ser Glu Leu Glu Tyr Gly
275 280 285

Asn Cys Asn Thr Lys Cys Gln Thr Pro Ile Gly Ala Ile Asn Ser Ser
290 295 300

Met Pro Phe His Asn Ile His Pro Leu Thr Ile Gly Glu Cys Pro Lys
305 310 315 320

Tyr Val Lys Ser Asn Arg Leu Val Leu Ala Thr Gly Leu Arg Asn Ser
325 330 335

Pro Gln Gly Glu Arg Arg Arg Arg Lys Arg Gly Leu Phe Gly Ala Ile
340 345 350

Ala Gly Phe Ile Glu Gly Gly Trp Gln Gly Met Val Asp Gly Trp Tyr
355 360 365

Gly Tyr His His Ser Asn Glu Gln Gly Ser Gly Tyr Ala Ala Asp Lys
370 375 380

Glu Ser Thr Gln Lys Ala Ile Asp Gly Val Thr Asn Lys Val Asn Ser
385 390 395 400

Ile Ile Asp Lys Met Asn Thr Gln Phe Glu Ala Val Gly Arg Glu Phe
405 410 415

Asn Asn Leu Glu Arg Arg Ile Glu Asn Leu Asn Lys Lys Met Glu Asp
420 425 430

Gly Phe Leu Asp Val Trp Thr Tyr Asn Ala Glu Leu Leu Val Leu Met
435 440 445

Glu Asn Glu Arg Thr Leu Asp Phe His Asp Ser Asn Val Lys Asn Leu
450 455 460

Tyr Asp Lys Val Arg Leu Gln Leu Arg Asp Asn Ala Lys Glu Leu Gly
465 470 475 480

Asn Gly Cys Phe Glu Phe Tyr His Arg Cys Asp Asn Glu Cys Met Glu
485 490 495

Ser Val Arg Asn Gly Thr Tyr Asp Tyr Pro Gln Tyr Ser Glu Glu Ala
500 505 510

Arg Leu Lys Arg Glu Glu Ile Ser Gly Val Lys Leu Glu Ser Ile Gly
515 520 525

Thr Tyr Gln Ile Leu Ser Ile Tyr Ser Thr Val Ala Ser Ser Leu Ala
530 535 540

Leu Ala Ile Met Val Ala Gly Leu Ser Leu Trp Met Cys Ser Asn Gly
545 550 555 560

Ser Leu Gln Cys Arg Ile Cys Ile
565

<210> SEQ ID NO 9
<211> LENGTH: 1735
<212> TYPE: DNA
<213> ORGANISM: artificial
<220> FEATURE:
<223> OTHER INFORMATION: Chicken/West Java/PWT-WIJ/2006

<400> SEQUENCE: 9
atggagaaaa tagtgcttct tcttgcaata gtcagccttg ttaaaagtga tcagatttgc 60
attggttacc atgcaaacaa ttcaacagag caggttgaca caatcatgga aaagaacgtt 120
actgttacac atgcccaaga catactggaa aagacacaca acgggaagct ctgcgatcta 180
gatggagtga agcctctaat tttaagagat tgtagtgtag ctggatggct cctcgggaac 240

-continued

```
ccaatgtgtg acgaattcat caaagtacag gaatggtctt acatagtgga gaaggccagt    300

ccaaccaatg acctctgtta tccagggagt ttcaacgact atgaagaact gaaacaccta    360

ttgagcagaa taaaacattt tgagaaaatt cgaatcatcc ccaaaagtga ttggtccgat    420

catgaagcct cattaggagt gagctcagca tgtccatacc tgggaagtcc ctcctttttt    480

agaaatgtgg tatggcttat caaaaagaac agtacatacc caacaataaa gaaaagctac    540

aagaatacca accaagaaga tcttttggta ctgtggggaa ttcaccattc taataatgtg    600

gaagagcaga caaggctata tcaaaaccca atcacctata tttccattgg gacatcaaca    660

ctaaaccaga gattggtacc aaaaatagct actagatcca aagtacacgg gcaaagtgga    720

aggatggatt tcttctggac aattttaaat cctaatgata caatcaactt cgagagtaat    780

ggaaatttca ttgctccaga atatgcatac aaaattgtca agaaagggga ctcagcaatt    840

atgaaaagtg aattggaata tggtgactgc aacactaagt gtcaaactcc aatgggggcg    900

ataaactcta gtatgccatt ccacaacata caccctctca ccatcgggga atgccccaaa    960

tatgtgaaat caaacagatt agtccttgca acagggctca gaaatagccc tcaaagagag   1020

agcagaagaa aaaagagagg actatttgga gctatagcag gttttataga gggaggatgg   1080

cagggaatgg tagatggttg gtatgggtac caccatagca atgagcaggg gagtgggtac   1140

gctgcagaca aagaatccac tcaaaaggca atagatggag tcaccaataa ggtcaactca   1200

atcattgaca aaatgaacac tcagtttgag gccgttggaa gggaatttaa taacttagaa   1260

aggagaatag agaatttaaa caagaagatg gaagacgggt ttctagatgt ttggacttat   1320

aatgccgaac ttctggttct catggaaaat gagagaactc tagactttca tgactcaaat   1380

gttaagaacc tctacgacaa ggtccgacta cagcttaggg ataatgcaaa ggagttgggt   1440

aacggttgtt tcgagttcta tcacaaatgt gataatgaat gtatggaaag tataagaaac   1500

ggaacgtaca actatccgca gtattcagaa gaagcaagat taaaaagaga ggaaataagt   1560

ggggtaaaat tggaatcaat aggaacttac caaatactgt caatttattc aacagtggcg   1620

agttccctag cactggcaat catgatggct ggtctatctt tatggatgtg ctccaatgga   1680

tcgttacaat gcagaatttg catttaaatt tgtgagttca gattgtagtt aaaaa        1735


<210> SEQ ID NO 10
<211> LENGTH: 568
<212> TYPE: PRT
<213> ORGANISM: artificial
<220> FEATURE:
<223> OTHER INFORMATION: Chicken/West Java/PWT-WIJ/2006

<400> SEQUENCE: 10

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Lys Val Gln Glu Trp Ser Tyr Ile Val
                85                  90                  95

Glu Lys Ala Ser Pro Thr Asn Asp Leu Cys Tyr Pro Gly Ser Phe Asn
            100                 105                 110
```

-continued

```
Asp Tyr Glu Glu Leu Lys His Leu Leu Ser Arg Ile Lys His Phe Glu
        115                 120                 125

Lys Ile Arg Ile Ile Pro Lys Ser Asp Trp Ser Asp His Glu Ala Ser
    130                 135                 140

Leu Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Lys Asn Thr Asn Gln Glu Asp Leu Leu Val Leu Trp
            180                 185                 190

Gly Ile His His Ser Asn Asn Val Glu Glu Gln Thr Arg Leu Tyr Gln
        195                 200                 205

Asn Pro Ile Thr Tyr Ile Ser Ile Gly Thr Ser Thr Leu Asn Gln Arg
    210                 215                 220

Leu Val Pro Lys Ile Ala Thr Arg Ser Lys Val His Gly Gln Ser Gly
225                 230                 235                 240

Arg Met Asp Phe Phe Trp Thr Ile Leu Asn Pro Asn Asp Thr Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asp Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
```

530 535 540

Leu Ala Ile Met Met Ala Gly Leu Ser Leu Trp Met Cys Ser Asn Gly
545 550 555 560

Ser Leu Gln Cys Arg Ile Cys Ile
565

<210> SEQ ID NO 11
<211> LENGTH: 1773
<212> TYPE: DNA
<213> ORGANISM: artificial
<220> FEATURE:
<223> OTHER INFORMATION: Turkey/Ireland/1378/1983

<400> SEQUENCE: 11
agcaaaagca ggggtataat ctgtcaaaat ggagaaaata gtgcttcttt ttgcaatagt 60
cagtcttgtc agaagtgacc agatttgcat tggttaccat gcaaacaact caacaaaaca 120
ggtcgacaca ataatggaaa agaatgttac tgtcacacat gcccaagaca tacttgaaaa 180
aacacacaac gggaagctct gcagcctaaa tggagtgaag cctctcattt tgagggattg 240
tagtgtagct ggatggctcc tcggaaatcc tatgtgtgac gaattcctta atgtgccaga 300
gtggtcttac atagtagaaa aggataatcc agtcaatggc ctttgctacc caggggattt 360
caacgactac gaagaactga aacatctatt aagttgtacg aaacattttg agaaaattcg 420
aatcatcccc agagattcct ggcccaacca tgaagcctca ttaggagtaa gctctgcatg 480
tccatacaat gggaggtctt ctttttcag gaatgtggta tggcttatca aaaagaacaa 540
tgcataccca acaataaaga ggagttacag caatactaat aaagaagatc ttctaatact 600
gtggggaatt caccatccta atgatgcagc agagcaaacc aagctctatc aaaacccaac 660
cacttatgtc tccgtcggaa catcaacact gaatcaaaga tcaattccaa aaatagccac 720
taggcccgaa ttaaatgggc aaagtggaag aatggaattc ttttggacga ttttgaagcc 780
aagtgatacc atcaattttg agagtaatgg aaacttcatt gctccagagt atgcctataa 840
aattgtcaag aagggggact cagcaatcat gaaaagtgga ttggaatatg gtaactgcaa 900
tactaagtgt caaactccaa taggtgcgat aaattccagc atgccactcc acaatataca 960
tcctcttacc attggagaat gccccaaata cgtgaaatca gatagattgg tccttgcaac 1020
tggactcagg aacacccctc aaagaaaaag aaaaaagaga ggtctatttg gagctatagc 1080
aggcttcata gaggggggat ggcagggaat ggtagacggt tggtatggtt accaccatag 1140
caacgagcag gggagtggat atgctgcaga caaagaatcc acccaaaggg caatagatgg 1200
aatcaccaat aaggtcaact caatcattga caaaatgaac acccagtttg aggcagttgg 1260
gaaggaattt aataacttag agagaagaat agaaaatttg aacaagaaaa tggaagacgg 1320
gtttctagat gtttggactt ataatgctga acttctagtt ctcatggaaa atgaaagaac 1380
tctagatttt catgacgcaa acgtcaagag cctttacgac aaggttcgac tacagcttaa 1440
ggataatgca agggaactgg gtaatggttg tttcgagttc taccataaat gtgacaatga 1500
atgtatggaa agcatcagaa acggaacata taactatcca cagtattcag aagaggcaag 1560
actaaacagg gaagaaataa gtggggtcaa attggaatca atgggaattt atcaaatact 1620
gtcaatttat tcaacagtgg cgagttccct agcactggca atcatgatag ctggtctatc 1680
tttctggatg tgctccaatg gatcattgca gtgcagaatt tgcatttaaa attattagtt 1740
cagattgtag ttaaaaacac ccttgtttct act 1773

<210> SEQ ID NO 12

<211> LENGTH: 566
<212> TYPE: PRT
<213> ORGANISM: artificial
<220> FEATURE:
<223> OTHER INFORMATION: Turkey/Ireland/1378/1983

<400> SEQUENCE: 12

```
Met Glu Lys Ile Val Leu Leu Phe Ala Ile Val Ser Leu Val Arg Ser
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Ser Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Val Asn Gly Leu Cys Tyr Pro Gly Asp Phe Asn
            100                 105                 110

Asp Tyr Glu Glu Leu Lys His Leu Leu Ser Cys Thr Lys His Phe Glu
        115                 120                 125

Lys Ile Arg Ile Ile Pro Arg Asp Ser Trp Pro Asn His Glu Ala Ser
    130                 135                 140

Leu Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Ser Tyr Ser Asn Thr Asn Lys Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Pro Thr Thr Tyr Val Ser Val Gly Thr Ser Thr Leu Asn Gln Arg
    210                 215                 220

Ser Ile Pro Lys Ile Ala Thr Arg Pro Glu Leu Asn Gly Gln Ser Gly
225                 230                 235                 240

Arg Met Glu Phe Phe Trp Thr Ile Leu Lys Pro Ser Asp Thr Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Gly Leu Glu Tyr Gly
        275                 280                 285

Asn Cys Asn Thr Lys Cys Gln Thr Pro Ile Gly Ala Ile Asn Ser Ser
    290                 295                 300

Met Pro Leu His Asn Ile His Pro Leu Thr Ile Gly Glu Cys Pro Lys
305                 310                 315                 320

Tyr Val Lys Ser Asp Arg Leu Val Leu Ala Thr Gly Leu Arg Asn Thr
                325                 330                 335

Pro Gln Arg Lys Arg Lys Lys Arg Gly Leu Phe Gly Ala Ile Ala Gly
            340                 345                 350

Phe Ile Glu Gly Gly Trp Gln Gly Met Val Asp Gly Trp Tyr Gly Tyr
        355                 360                 365

His His Ser Asn Glu Gln Gly Ser Gly Tyr Ala Ala Asp Lys Glu Ser
    370                 375                 380
```

-continued

```
Thr Gln Arg Ala Ile Asp Gly Ile Thr Asn Lys Val Asn Ser Ile Ile
385                 390                 395                 400

Asp Lys Met Asn Thr Gln Phe Glu Ala Val Gly Lys Glu Phe Asn Asn
                405                 410                 415

Leu Glu Arg Arg Ile Glu Asn Leu Asn Lys Lys Met Glu Asp Gly Phe
            420                 425                 430

Leu Asp Val Trp Thr Tyr Asn Ala Glu Leu Leu Val Leu Met Glu Asn
        435                 440                 445

Glu Arg Thr Leu Asp Phe His Asp Ala Asn Val Lys Ser Leu Tyr Asp
    450                 455                 460

Lys Val Arg Leu Gln Leu Lys Asp Asn Ala Arg Glu Leu Gly Asn Gly
465                 470                 475                 480

Cys Phe Glu Phe Tyr His Lys Cys Asp Asn Glu Cys Met Glu Ser Ile
                485                 490                 495

Arg Asn Gly Thr Tyr Asn Tyr Pro Gln Tyr Ser Glu Glu Ala Arg Leu
            500                 505                 510

Asn Arg Glu Glu Ile Ser Gly Val Lys Leu Glu Ser Met Gly Ile Tyr
        515                 520                 525

Gln Ile Leu Ser Ile Tyr Ser Thr Val Ala Ser Ser Leu Ala Leu Ala
    530                 535                 540

Ile Met Ile Ala Gly Leu Ser Phe Trp Met Cys Ser Asn Gly Ser Leu
545                 550                 555                 560

Gln Cys Arg Ile Cys Ile
                565
```

<210> SEQ ID NO 13
<211> LENGTH: 1695
<212> TYPE: DNA
<213> ORGANISM: artificial
<220> FEATURE:
<223> OTHER INFORMATION: Viet Nam/1203/2004

<400> SEQUENCE: 13

```
atggagaaaa tagtgcttct tttgcaata gtcagtcttg ttaaaagtga tcagatttgc     60

attggttacc atgcaaacaa ctcgacagag caggttgaca caataatgga aaagaacgtt    120

actgttacac atgcccaaga catactggaa aagaaacaca acgggaagct ctgcgatcta    180

gatggagtga agcctctaat tttgagagat tgtagcgtag ctggatggct cctcggaaac    240

ccaatgtgtg acgaattcat caatgtgccg gaatggtctt acatagtgga gaaggccaat    300

ccagtcaatg acctctgtta cccaggggat ttcaatgact atgaagaatt gaaacaccta    360

ttgagcagaa taaaccattt tgagaaaatt cagatcatcc ccaaaagttc ttggtccagt    420

catgaagcct cattaggggt gagctcagca tgcccatacc agggaaagtc ctcctttttc    480

agaaatgtgg tatggcttat caacaagaac agtacatacc caacaataaa gaggagctac    540

aataatacca accaagaaga tcttttggta ctgtgggga ttcaccatcc taatgatgcg    600

gcagagcaga caaagctcta tcaaaaccca accacctata tttccgttgg gacatcaaca    660

ctaaaccaga gattggtacc aagaatagct actagatcca aagtaaacgg gcaaagtgga    720

aggatggagt tcttctggac aattttaaag ccgaatgatg caatcaactt cgagagtaat    780

ggaaatttca ttgctccaga atatgcatac aaaattgtca agaaagggga ctcaacaatt    840

atgaaaagtg aattggaata tggtaactgc aacaccaagt gtcaaactcc aatggggggcg   900

ataaactcta gcatgccatt ccacaatata caccctctca ccattgggga atgccccaaa    960

tatgtgaaat caaacagatt agtccttgcg actgggctca gaaatagccc tcaacgagag   1020
```

```
acgcgaggat tatttggagc tatagcaggt tttatagagg gaggatggca gggaatggta   1080

gatggttggt atgggtacca ccatagcaat gagcagggga gtgggtacgc tgcagacaaa   1140

gaatccactc aaaaggcaat agatggagtc accaataagg tcaactcgat cattgacaaa   1200

atgaacactc agtttgaggc cgttggaagg gaatttaaca acttagaaag gagaatagag   1260

aatttaaaca agaagatgga agacgggttc ctagatgtct ggacttataa tgctgaactt   1320

ctggttctca tggaaaatga gagaactcta gactttcatg actcaaatgt caagaacctt   1380

tacgacaagg tccgactaca gcttagggat aatgcaaagg agctgggtaa cggttgtttc   1440

gagttctatc ataaatgtga taatgaatgt atggaaagtg taagaaatgg aacgtatgac   1500

tacccgcagt attcagaaga agcgagacta aaaagagagg aaataagtgg agtaaaattg   1560

gaatcaatag gaatttacca aatactgtca atttattcta cagtggcgag ttccctagca   1620

ctggcaatca tggtagctgg tctatcctta tggatgtgct ccaatggatc gttacaatgc   1680

agaatttgca tttaa                                                    1695
```

```
<210> SEQ ID NO 14
<211> LENGTH: 564
<212> TYPE: PRT
<213> ORGANISM: artificial
<220> FEATURE:
<223> OTHER INFORMATION: Viet Nam/1203/2004

<400> SEQUENCE: 14

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Asn Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
```

-continued

```
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile


<210> SEQ ID NO 15
<211> LENGTH: 1305
<212> TYPE: DNA
<213> ORGANISM: artificial
<220> FEATURE:
<223> OTHER INFORMATION: rice

<400> SEQUENCE: 15

atgcaggtgc tgaacaccat ggtgaacaaa cacttcttgt ccctttcggt cctcatcgtc      60

ctccttggcc tctcctccaa cttgacagcc gggcaagtcc tgtttcaggg attcaactgg     120

gagtcgtgga aggagaatgg cgggtggtac aacttcctga tgggcaaggt ggacgacatc     180

gccgcagccg gcatcaccca cgtctggctc cctccgccgt ctcactctgt cggcgagcaa     240

ggctacatgc ctgggcggct gtacgatctg gacgcgtcta agtacggcaa cgaggcgcag     300
```

```
ctcaagtcgc tgatcgaggc gttccatggc aagggcgtcc aggtgatcgc cgacatcgtc    360

atcaaccacc gcacggcgga gcacaaggac ggccgcggca tctactgcct cttcgagggc    420

gggacgcccg actcccgcct cgactggggc ccgcacatga tctgccgcga cgacccctac    480

ggcgatggca ccggcaaccc ggacaccggc gccgacttcg ccgccgcgcc ggacatcgac    540

cacctcaaca agcgcgtcca gcgggagctc attggctggc tcgactggct caagatggac    600

atcggcttcg acgcgtggcg cctcgacttc gccaagggct actccgccga catggcaaag    660

atctacatcg acgccaccga gccgagcttc gccgtggccg agatatggac gtccatggcg    720

aacggcgggg acggcaagcc gaactacgac cagaacgcgc accggcagga gctggtcaac    780

tgggtcgatc gtgtcggcgg cgccaacagc aacggcacgg cgttcgactt caccaccaag    840

ggcatcctca acgtcgccgt ggagggcgag ctgtggcgcc tccgcggcga ggacggcaag    900

gcgcccggca tgatcgggtg gtggccggcc aaggcgacga ccttcgtcga caaccacgac    960

accggctcga cgcagcacct gtggccgttc ccctccgaca aggtcatgca gggctacgca   1020

tacatcctca cccaccccgg caacccatgc atcttctacg accatttctt cgattggggt   1080

ctcaaggagg agatcgagcg cctggtgtca atcagaaacc ggcaggggat ccacccggcg   1140

agcgagctgc gcatcatgga agctgacagc gatctctacc tcgcggagat cgatggcaag   1200

gtgatcacaa agattggacc aagatacgac gtcgaacacc tcatccccga aggcttccag   1260

gtcgtcgcgc acggtgatgg ctacgcaatc tgggagaaaa tctga                   1305
```

```
<210> SEQ ID NO 16
<211> LENGTH: 434
<212> TYPE: PRT
<213> ORGANISM: artificial
<220> FEATURE:
<223> OTHER INFORMATION: rice

<400> SEQUENCE: 16

Met Gln Val Leu Asn Thr Met Val Asn Lys His Phe Leu Ser Leu Ser
1               5                   10                  15

Val Leu Ile Val Leu Leu Gly Leu Ser Ser Asn Leu Thr Ala Gly Gln
            20                  25                  30

Val Leu Phe Gln Gly Phe Asn Trp Glu Ser Trp Lys Glu Asn Gly Gly
        35                  40                  45

Trp Tyr Asn Phe Leu Met Gly Lys Val Asp Asp Ile Ala Ala Ala Gly
    50                  55                  60

Ile Thr His Val Trp Leu Pro Pro Pro Ser His Ser Val Gly Glu Gln
65                  70                  75                  80

Gly Tyr Met Pro Gly Arg Leu Tyr Asp Leu Asp Ala Ser Lys Tyr Gly
                85                  90                  95

Asn Glu Ala Gln Leu Lys Ser Leu Ile Glu Ala Phe His Gly Lys Gly
            100                 105                 110

Val Gln Val Ile Ala Asp Ile Val Ile Asn His Arg Thr Ala Glu His
        115                 120                 125

Lys Asp Gly Arg Gly Ile Tyr Cys Leu Phe Glu Gly Gly Thr Pro Asp
    130                 135                 140

Ser Arg Leu Asp Trp Gly Pro His Met Ile Cys Arg Asp Asp Pro Tyr
145                 150                 155                 160

Gly Asp Gly Thr Gly Asn Pro Asp Thr Gly Ala Asp Phe Ala Ala Ala
                165                 170                 175

Pro Asp Ile Asp His Leu Asn Lys Arg Val Gln Arg Glu Leu Ile Gly
            180                 185                 190
```

```
Trp Leu Asp Trp Leu Lys Met Asp Ile Gly Phe Asp Ala Trp Arg Leu
        195                 200                 205

Asp Phe Ala Lys Gly Tyr Ser Ala Asp Met Ala Lys Ile Tyr Ile Asp
    210                 215                 220

Ala Thr Glu Pro Ser Phe Ala Val Ala Glu Ile Trp Thr Ser Met Ala
225                 230                 235                 240

Asn Gly Gly Asp Gly Lys Pro Asn Tyr Asp Gln Asn Ala His Arg Gln
                245                 250                 255

Glu Leu Val Asn Trp Val Asp Arg Val Gly Gly Ala Asn Ser Asn Gly
            260                 265                 270

Thr Ala Phe Asp Phe Thr Thr Lys Gly Ile Leu Asn Val Ala Val Glu
        275                 280                 285

Gly Glu Leu Trp Arg Leu Arg Gly Glu Asp Gly Lys Ala Pro Gly Met
    290                 295                 300

Ile Gly Trp Trp Pro Ala Lys Ala Thr Thr Phe Val Asp Asn His Asp
305                 310                 315                 320

Thr Gly Ser Thr Gln His Leu Trp Pro Phe Pro Ser Asp Lys Val Met
                325                 330                 335

Gln Gly Tyr Ala Tyr Ile Leu Thr His Pro Gly Asn Pro Cys Ile Phe
            340                 345                 350

Tyr Asp His Phe Phe Asp Trp Gly Leu Lys Glu Glu Ile Glu Arg Leu
        355                 360                 365

Val Ser Ile Arg Asn Arg Gln Gly Ile His Pro Ala Ser Glu Leu Arg
    370                 375                 380

Ile Met Glu Ala Asp Ser Asp Leu Tyr Leu Ala Glu Ile Asp Gly Lys
385                 390                 395                 400

Val Ile Thr Lys Ile Gly Pro Arg Tyr Asp Val Glu His Leu Ile Pro
                405                 410                 415

Glu Gly Phe Gln Val Val Ala His Gly Asp Gly Tyr Ala Ile Trp Glu
            420                 425                 430

Lys Ile


<210> SEQ ID NO 17
<211> LENGTH: 8
<212> TYPE: PRT
<213> ORGANISM: artificial
<220> FEATURE:
<223> OTHER INFORMATION: basic amino acid region of HA gene

<400> SEQUENCE: 17

Arg Glu Arg Arg Arg Lys Lys Arg
1               5


<210> SEQ ID NO 18
<211> LENGTH: 4
<212> TYPE: PRT
<213> ORGANISM: artificial
<220> FEATURE:
<223> OTHER INFORMATION: mutated HA cleavage site

<400> SEQUENCE: 18

Arg Glu Thr Arg
1
```

RECOMBINANT AVIAN INFLUENZA VACCINE AND USES THEREOF

CROSS-REFERENCE TO RELATED APPLICATIONS

This application claims benefit of U.S. provisional application Ser. No. 61/118,492 filed Nov. 28, 2008.

FIELD OF THE INVENTION

The present invention encompasses influenza vaccines, in particular avian influenza vaccines. The vaccine may be a recombinant avian vaccine.

BACKGROUND OF THE INVENTION

Avian influenza, sometimes avian flu, and commonly bird flu refers to influenza caused by viruses adapted to birds. Avian influenza virus (AIV) is an RNA virus belonging to the family of Orthomyxoviridae, and is classified as a type A influenza virus, which relates to its nucleoprotein and membrane proteins. AIV has a lipid envelope that features two distinct glycoproteins: hemagglutinin (HA), which facilitates entry of the virus into the host cells, and neuraminidase (NA), which assists in the release of progeny virus from infected cells (de Jong et al., J Clin Virol. 2006 January; 35(1):2-13). The H5N1 subtype (virus featuring HA 5 and NA 1) has specifically been associated with recent outbreaks in Asia, Russia, the Middle East, Europe and Africa (Olsen et al., Science. 2006 Apr. 21; 312(5772):384-8).

The highly pathogenic Influenza A virus subtype H5N1 virus is an emerging avian influenza virus that has been causing global concern as a potential pandemic threat. H5N1 has killed millions of poultry in a growing number of countries throughout Asia, Europe and Africa. Health experts are concerned that the co-existence of human flu viruses and avian flu viruses (especially H5N1) will provide an opportunity for genetic material to be exchanged between species-specific viruses, possibly creating a new virulent influenza strain that is easily transmissible and lethal to humans (Food Safety Research Information Office. "A Focus on Avian Influenza". Created May 2006, Updated November 2007).

Since the first H5N1 outbreak occurred in 1997, there have been an increasing number of HPAI H5N1 bird-to-human transmissions leading to clinically severe and fatal human infections. However, because there is a significant species barrier that exists between birds and humans, the virus does not easily cross over to humans. Although millions of birds have become infected with the virus since its discovery, over 200 humans have died from Avian Flu in Indonesia, Laos, Vietnam, Romania, China, Turkey and Russia.

Recently, plants have been investigated as a source for the production of therapeutic agents such as vaccines, antibodies, and biopharmaceuticals. However, the production of vaccines, antibodies, proteins, and biopharmaceuticals from plants is far from a remedial process, and there are numerous obstacles that are commonly associated with such vaccine production. Limitations to successfully producing plant vaccines include low yield of the bioproduct or expressed antigen (Chargelegue et al., Trends in Plant Science 2001, 6, 495-496), protein instability, inconsistencies in product quality (Schillberg et al., Vaccine 2005, 23, 1764-1769), and insufficient capacity to produce viral-like products of expected size and immunogenicity (Arntzen et al., Vaccine 2005, 23, 1753-1756).

Considering the susceptibility of animals, including humans, to AIV, a method of preventing AIV infection and protecting animals is essential. Accordingly, there is a need for methods to produce effective vaccines against influenza.

SUMMARY OF THE INVENTION

Compositions comprising an influenza polypeptide and fragments and variants thereof are provided. The polypeptide or antigen is produced in a plant, and is highly immunogenic and protective.

The polypeptides and fragments and variants thereof can be formulated into vaccines and/or pharmaceutical or immunological compositions. Such vaccines or compositions can be used to vaccinate an animal and provide protection against at homologous and heterologous influenza strains.

Methods of the invention include methods of use including administering to an animal an effective amount of an antigenic polypeptide or fragment or variant thereof to produce a protective immunogenic response. Methods also include methods for making the antigenic polypeptides in duckweed plant. After production in duckweed the antigenic polypeptide can be partially or substantially purified for use as a vaccine or immunological composition.

Kits comprising at least one antigenic polypeptide or fragment or variant thereof and instructions for use are also provided.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 is a table showing the SEQ ID NO assigned to the polynucleotide and protein sequence.

FIG. 2 provides the Synthetic (Codon-optimized) and mutated DNA sequence coding for the A/chicken/Indonesia/7/2003H5N1 hemagglutinin (HA) (SEQ ID NO:1).

FIG. 3 provides the native and synthetic/mutated A/chicken/Indonesia/7/2003H5N1 (HA) protein sequences FIG. 4 provides A/chicken/Indonesia/7/2003(H5N1) wild type (native) cDNA sequence of the HA gene (GenBank Accession No. EF473080) (SEQ ID NO:3).

FIG. 5 shows the HA protein sequence alignment and sequence identity table. The sequence identity between SEQ ID NO:4 and SEQ ID NO:5 is 99% using Vector NTI 11.0 (PC) software package (Invitrogen, 1600 Faraday Ave., Carlsbad, Calif.). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides.

FIG. 6 depicts the MerB01 vector sequence (SEQ ID NO:6)

FIG. 8 shows the DNA sequence alignment and sequence identity table. The sequence identity between SEQ ID NO:1 and SEQ ID NO:3 is 74% using Vector NTI 11.0 (PC) software package (Invitrogen, 1600 Faraday Ave., Carlsbad, Calif.). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. The percent identity was calculated based on the shorter sequence.

FIG. 9 shows a plate example of the HA screening of positive transgenic plants and the HA assay results.

FIG. 11 provides a table showing the estimated yield of target formulation.

FIG. 12: The Rockland mAB was diluted 1:100 in the first well then 1:2 across the plate and the Biolex and recombinant H5N1 HA antigens were diluted 1:10000 and the inactivated H5N1 virus (EID50=$10^{8.5}$/ml) was diluted 1:32. The mAB endpoint titer against inactivated H5N1 virus was 400; the titer against Rec. H5N1 HA was 100; and the titer against Biolex H5N1 HA was 100.

FIG. 13: Anti-H5N1 chicken serum (Indo/7/03 vaccinated) was diluted 1:10 in the first well then 1:2 across the plate and the Biolex and recombinant H5N1 HA antigens were diluted 1:10000 and the inactivated H5N1 virus (EID50=$10^{8.5}$/ml) was diluted 1:32. The anti-H5N1 chicken serum endpoint titer against inactivated H5N1 virus was 640; the titer against Rec. H5N1 HA was 320; and the titer against Biolex H5N1 HA was 80.

FIG. 14: Anti-H5N1 chicken serum (FP2211) was diluted 1:10 in the first well then 1:2 across the plate and the Biolex and recombinant H5N1 HA antigens were diluted 1:10000 and the inactivated H5N1 virus (EID50=$10/^{8.5}$/ml) was diluted 1:32. The anti-H5N1 chicken serum endpoint titer against inactivated H5N1 virus was 640; the titer against Rec. H5N1 HA was 640; and the titer against Biolex H5N1 HA was 80.

FIG. 15 shows the SDS-PAGE (silver staining) and Western-blot. FIGS. 15*a* and 15*b* show in vitro characterization of *Lemna* derived HA. Crude *Lemna* tissue extract was analyzed by SDS-PAGE (A). M refers to Bio-Rad Kaleidoscope MW Standard, lanes 1-2, recombinant HA (positive control) diluted at 1:1 and 1:10, respectively, lanes 3-4, crude *Lemna* extract diluted at 1:1 and 1:10, respectively, lanes 5-6, *Lemna* wild type extract diluted at 1:1 and 1:10, respectively. Crude *Lemna* tissue extract was analyzed by Western blot using monoclonal antibody against H5 Hemagglutinin of A/Vietnam/1203/04 Influenza Virus (B). Lane1: Bio-Rad Kaleidoscope MW Standard, lanes 1-2, Crude *Lemna* extract diluted at 1:10 and 1:1, respectively, lanes 3-4, *Lemna* wild type extract diluted at 1:10 and 1:1, respectively.

FIG. 18 is a table showing the vaccination scheme of the immunogenicity study. One-day-old or 3-week-old SPF chickens (10/group) were vaccinated once or twice with the adjuvanted crude *Lemna* extract at different doses (0.3 ml/dose by IM route), or prime-boost with TROVAC® AI H5 (0.2 ml/dose by SQ in the nape of the neck) followed with *Lemna* HA 6550 HAU.

FIG. 19 provides a summary of protection data after HPAI H5N1 challenge. FIG. 19 shows the summary of protection induced by different formulations against HPAI H5N1 challenge. One-day-old or 3 week-old SPF chickens (10/group) were vaccinated once with the adjuvanted crude *Lemna* extract at different antigenic doses (0.3 ml formulated vaccine /dose by IM route), or prime-boost scheme with TROVAC® AIV H5 (0.2 ml/dose by SQ in the nape of the neck) followed with *Lemna* HA 6550 HAU. Summary of protection induced by different formulations against HPAI H5N1 challenge: One-day-old or 3 week-old SPF chickens (10/group) were vaccinated once with the adjuvanted crude *Lemna* extract at different antigenic doses (0.3 ml formulated vaccine /dose by IM route), or prime-boost scheme with TROVAC® AIV H5 (0.2 ml/dose by SQ in the nape of the neck) followed with *Lemna* HA 6550 HAU. As shown in the table: [1] H5N1 virus shedding determined by quantitative RT-PCR. Quantitative RT-PCR samples with Ct values>38 were confirmed by PCR for the NS1 gene. Titer values for the NS1-positive samples were calculated from the Smart Cycler line equation. ND, not detected after 45 cycles of quantitative RT-PCR (AI matrix gene), or detected by with a Ct value>38 but not detected by the NS1 test. RT-PCR detection limits: 2.9 log EID50/ml (Indo 0/3) and 3.6 log EID50/ml (WJ/06). Negative samples given a value 0.1 Log EID50/ml below the detection limit [2] Mean time to death in days; [3] Days post challenge; [4] A/ck/Indonesia/7/2003 HPAI H5N1; [5] Number of positive/total number; [6] A/ck/WestJava/PWT-WU/2006 HPAI H5N1; [7] Bird was euthanized due to severe torticollis.

FIG. 20 shows hemagglutination inhibition titer (log 2) from sera collected on day 35 in chickens vaccinated with *Lemna* derived HA. (A) One vaccination in 3-wk-old chickens on day 0. (B) Two vaccinations in 3-wk-old chickens on days 0 and 21. (C) Comparison between two vaccination (6550HAU) and prime-boost schemes with TROVAC® AI H5 priming at day 0 and *Lemna* derived HA (6550HAU) boost at day 21 in one-day-old chickens.

FIG. 21 shows a table summarizing serological data on samples collected before challenge on day 42 and after challenge on day 56.

DETAILED DESCRIPTION

Figure 7:
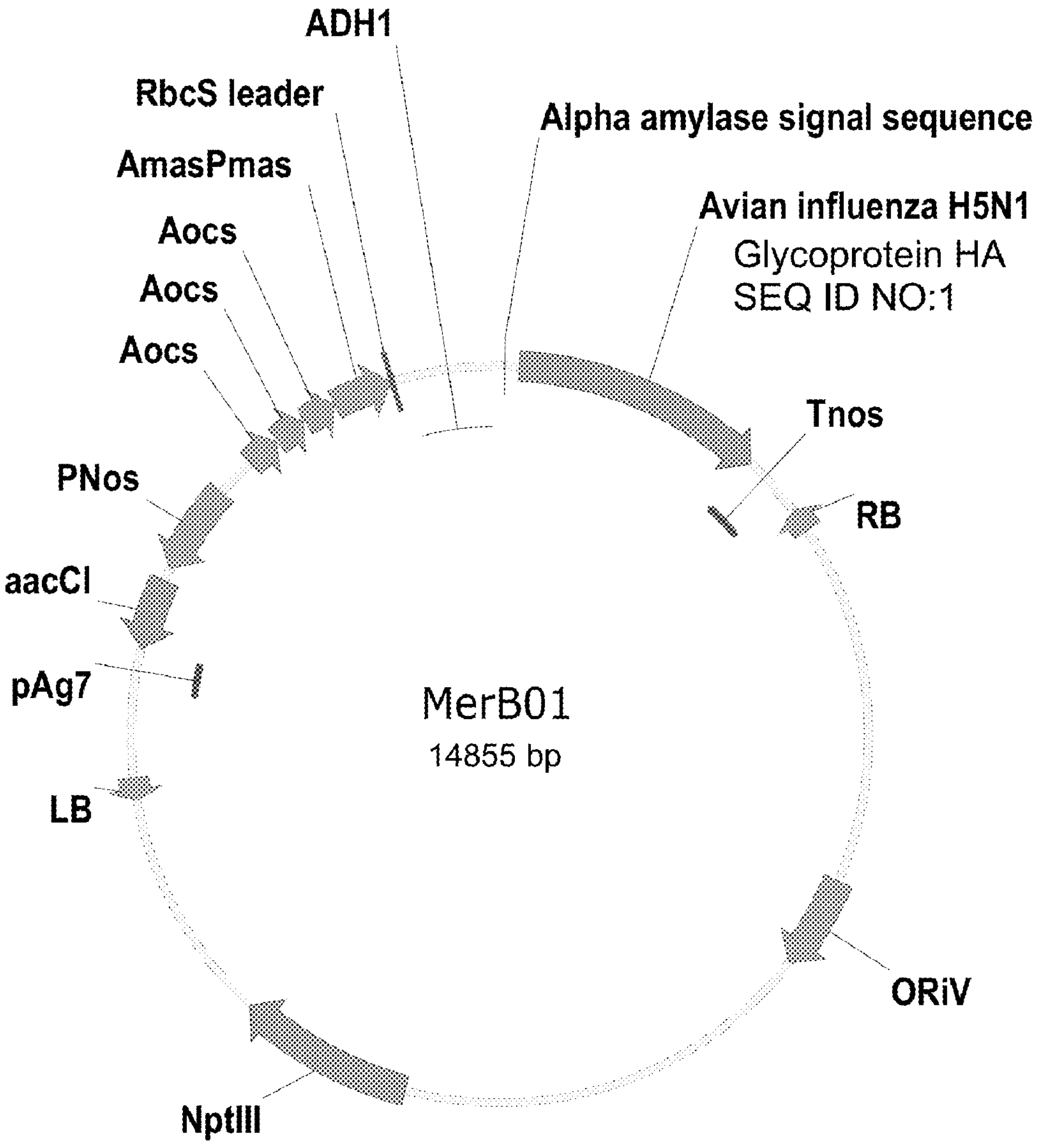
FIG. 7 shows the MerB01 vector map.

Compositions comprising an influenza antigen and fragments and variants thereof that elicit an immunogenic response in an animal are provided. The antigenic polypeptides or fragments or variants thereof may be produced in a duckweed plant. The antigenic polypeptides or fragments or variants may be formulated into vaccines or pharmaceutical or immunological compositions and used to elicit or stimulate a protective response in an animal. In one embodiment the polypeptide antigen is a hemagglutinin polypeptide or active fragment or variant thereof.

It is recognized that the antigenic polypeptides or antigens of the invention may be full length polypeptides or active fragments or variants thereof. By "active fragments" or "active variants" is intended that the fragments or variants retain the antigenic nature of the polypeptide. Thus, the present invention encompasses any influenza polypeptide, antigen, epitope or immunogen that elicits an immunogenic response in an animal. The influenza polypeptide, antigen, epitope or immunogen may be any influenza polypeptide, antigen, epitope or immunogen, such as, but not limited to, a protein, peptide or fragment or variant thereof, that elicits, induces or stimulates a response in an animal.

A particular antigenic polypeptide of interest is hemagglutinin (HA). Influenze hemagglutinin refers to a type of hemagglutinin found on the surface of the influenza viruses. It is an antigenic glycoprotein and is responsible for binding the virus to the cell that is being infected. There are different HA antigens, any of which can be used in the practice of the invention. Of interest is the HA from H5N1, a highly pathogenic avian flu virus. More particularly, the HA may be isolated from H5N1 isolated from the A/chicken/Indonesia/7/2003 strain. However, HA from other influenza viruses (i.e. H1-H16) may be used in the practice of the invention including H1, H3, H5, H6, H7, H9 and the like. It is further recognized that HA precursors of any of the HA proteins can be used.

HA is a homotrimeric transmembrane protein with an ectodomain composed of a globular head and a stem region. Both regions carry N-linked oligosaccharides, which plays an important role in the biological function of HA (Schulze, I. T., J Infect Dis, 1997. 176 Suppl 1: p. S24-8; Deshpande, K. L., et al., PNAS USA, 1987, 84(1): p. 36-40). Among different subtypes of influenza A viruses, there is significant variation in the glycosylation sites of the head region, whereas the stem oligosaccharides are more conserved and required for fusion activity (Ohuchi, R., et al., J Virol, 1997, 71(5): p. 3719-25). Glycans near antigenic peptide epitopes interfere with antibody recognition (Skehel, J. J., et al., *PNAS* USA, 1984, 81(6): p. 1779-83), and glycans near the proteolytic site modulate cleavage and influence the infectivity of influenza virus (Deshpande, K. L., et al., 1987). Nucleotide sequence analysis of 62 H5 genes supported the hypothesis that additional glycosylation near the receptor binding site within the HA globular head is an adaptation of the virus following interspecies transmission from wild birds, particularly waterfowl, to poultry (Banks, J., et al., Avian Dis, 2003, 47(3 Suppl): p. 942-50).

Over 150 B cell epitopes as well as 113 CD4+ and 35 CD8+ T cell epitopes have been identified for HA protein of influenza virus, however, only a limited number of epitopes reported for avian influenza strains/subtybtypes (Bui, H. H., et al., PNAS USA, 2007, 104(1): p. 246-51). Examination of the sites of amino acid substitutions in natural and monoclonal antibody-selected antigenic variants indicated that all antigenic sites are on the surface of the membrane distal HA1 domain predominantly surrounding the receptor-binding sites. There are two notable features of the antigenic sites: the loop like structure of several of them and the incidence of carbohydrate side chains (Skehel, J. J., et al., Annu Rev Biochem, 2000, 69: p. 531-69). The localization and fine structure of two H5 antigenic sites have been described (Kaverin, N. V., et al., J Gen Virol, 2002. 83(Pt 10): p. 2497-505). Site 1 is an exposed loop comprising HA1 residues 140-145 that corresponds to antigenic sites A of H3 and Ca2 of H1, and site 2 comprised two subsites, one (HA1 residues 156 and 157) that corresponds to site B in the H3 subtype and one (HA1 residues 129 to 133) that corresponds to site Sa in the H1 subtype. An epitope mapping study suggested that HA antigenic structure of recent H5N1 isolated differs substantially from that of a low-pathogencity H5 strain and is rapidly evolving (Kaverin, N. V., et al., J Virol, 2007. 81(23): p. 12911-7). An epitope conservancy analysis suggested significant levels of interstrain cross-reactivity are likely for T cell epitopes, but much less so for Ab epitopes. Using an overlapping peptide library, a T cell epitope of AIV was identified for the first time, which is a 15-mer peptide, $H_{246-260}$ within the HA1 domain which induced action of T cells in chickens immunized against H5 HA (Haghighi, H. R., et al., PLoS ONE, 2009. 4(11): p. e7772).

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicate otherwise.

By "animal" is intended mammals, birds, and the like. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The antigenic polypeptides of the invention are capable of protecting against influenza. That is, they are capable of stimulating an immune response in an animal. By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic or antigenic" polypeptide, as used herein, includes the full-length sequence of the protein, analogs thereof, or immunogenic fragments thereof. By "immunogenic or antigenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of an influenza polypeptide. A polynucleotide encoding a fragment of an influenza polypeptide may comprise or consist essentially of or consist of a minimum of 15 nucleotides, about 30-45 nucleotides, about 45-75, or at least 57, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding an influenza antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. That is the polypeptide is separated from cellular components. By "substantially purified" is intended that such that at least 60%, at least 70%, at least 80%, at least 90%, at least 95%, or at least 98%, or more of the cellular components or materials have been removed. Likewise, the polypeptide may be partially purified. By "partially purified" is intended that less than 60% of the cellular components or material is removed. The same applies to polynucleotides. The polypeptides disclosed herein can be purified by any of the means known in the art.

As noted above, the antigenic polypeptides or fragments or variants thereof are influenza antigenic polypeptides that are produced in duckweed. Fragments and variants of the disclosed polynucleotides and polypeptides encoded thereby are also encompassed by the present invention. By "fragment" is intended a portion of the polynucleotide or a portion of the antigenic amino acid sequence encoded thereby. Fragments of a polynucleotide may encode protein fragments that retain the biological activity of the native protein and hence have immunogenic activity as noted elsewhere herein. Fragments of the polypeptide sequence retain the ability to induce a protective immune response in an animal.

"Variants" is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they the ability to elicit an immune response.

Homologs of influenza polypeptides from avian, pigs, equine, cats, dogs, ducks, turkeys, chickens, quails and other species including wild animals are intended to be within the scope of the present invention. As used herein, the term "homologs" includes orthologs, analogs and paralogs. The term "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type influenza polypeptide can differ from the wild-type influenza polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type influenza polypeptide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the influenza polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein. The term "variant" also includes the modification of a polypeptide where the native signal peptide is replaced with a heterologous signal peptide to facilitate the expression or secretion of the polypeptide from a host species. It includes also the modification of a polypeptide where the transmembrane domain and/or cytoplasmic tail is replaced with similar heterologous sequences to facilitate membrane expression of the polypeptide in a host species.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for influenza polypeptides, the DNA sequence of the influenza protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of influenza protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the influenza polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The present invention relates to an avian vaccine or a pharmaceutical or immunological composition which may comprise an effective amount of a recombinant avian influenza antigen and a pharmaceutically or veterinarily acceptable carrier, excipient, or vehicle.

The subject matter described herein is directed in part, to compositions and methods related to the surprising discovery that an avian influenza antigen prepared in a plant protein expression system was highly immunogenic and protected chickens against challenge from homologous and heterologous avian influenza strains.

Compositions

In an embodiment, the subject matter disclosed herein is directed to a composition comprising an influenza antigen and a pharmaceutical or veterinarily acceptable carrier, excipient or vehicle.

In an embodiment, the subject matter disclosed herein is directed to a composition comprising an avian influenza antigen produced by a *Lemna* expression system and a pharmaceutical or veterinarily acceptable carrier, excipient or vehicle.

In an embodiment, the subject matter disclosed herein is directed to a composition comprising an avian influenza antigen produced by a *Lemna* expression system and plant material from the genus *Lemna* and a pharmaceutical or veterinarily acceptable carrier, excipient or vehicle.

In an embodiment, the subject matter disclosed herein is directed to a protein produced by a *Lemna* expression system comprising an avian influenza antigen. The protein may be glycosylated.

In an embodiment, the subject matter disclosed herein is directed to a protein produced by a *Lemna* expression system comprising an avian influenza antigen and plant material from the genus *Lemna*.

In an embodiment, the subject matter disclosed herein is directed to a stably transformed plant or plant culture that expresses an avian influenza antigen wherein the plant or plant culture is selected from the genus *Lemna*.

In an embodiment wherein the avian influenza immunological composition or vaccine is a recombinant immunological composition or vaccine, the composition or vaccine comprising a recombinant vector and a pharmaceutical or veterinary acceptable excipient, carrier or vehicle; the recombinant vector is plant expression vector which may comprise a polynucleotide encoding an influenza polypeptide, antigen, epitope or immunogen. The influenza polypeptide, antigen, epitope or immunogen, may be a hemagglutinin, matrix protein, neuraminidase, nonstructural protein, nucleoprotein, polymerase or any fragment thereof.

In another embodiment, the influenza polypeptide, antigen, epitope or immunogen may be derived from an avian infected with influenza or an avian influenza strain. In one embodiment, the avian influenza antigen, epitope or immunogen is a hemagglutinin (HA) (e.g., HA0 precursor, HA1 and/or HA2), H1, H2, protein, matrix protein (e.g., matrix protein M1 or M2), neuraminidase, nonstructural (NS) protein (e.g., NS1 or NS2), nucleoprotein (NP) and polymerase (e.g., PA polymerase, PB1 polymerase 1 or PB2 polymerase 2). Influenza type A viruses can infect people, birds, pigs, horses, dogs, cats, and other animals, but wild birds are the natural hosts for these viruses.

In another embodiment, the avian influenza antigen may be a hemagglutinin (HA) from different influenza A subtypes (examples: H1, H3, H5, H6, H7, H9). In yet another embodiment, the avian influenza antigen may be the HA from H5N1 isolate. In another embodiment, the H5N1 antigen is isolated from the A/chicken/Indonesia/7/2003 strain.

The present invention relates to an avian vaccine or composition which may comprise an effective amount of a recombinant avian influenza antigen and a pharmaceutically or veterinarily acceptable carrier, excipient, or vehicle. In one embodiment, the avian influenza antigen may be a hemagglutinin.

In another embodiment, the recombinant influenza antigen is expressed in a plant. In yet another embodiment, the plant is a duckweed. In yet another embodiment, the plant is a *Lemna* plant. In one embodiment, the recombinant influenza antigen may be expressed in a proprietary *Lemna* minor protein expression system, the Biolex's LEX system$^{SM}$.

In another embodiment, the pharmaceutically or veterinarily acceptable carrier, excipient, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, or vehicle may be an oil-in-water emulsion.

The invention further encompasses the influenza polynucleotides contained in a vector molecule or an expression vector and operably linked to a promoter element and optionally to an enhancer.

In one aspect, the present invention provides influenza polypeptides, particularly avian influenza polypeptides. In another aspect, the present invention provides a polypeptide having a sequence as set forth in SEQ ID NO: 2, 4, 5, 8, 10, 12, or 14 and variant or fragment thereof.

In another aspect, the present invention provides a polypeptide having at least 70%, at least 75%, at least 80%, at least 85%, at least 90%, at least 95%, 96%, 97%, 98% or 99% sequence identity to an antigenic polypeptide of the invention, particularly to the polypeptides having a sequence as set forth in SEQ ID NO: 2, 4, 5, 8, 10, 12, or 14.

In yet another aspect, the present invention provides fragments and variants of the influenza polypeptides identified above (SEQ ID NO: 2, 4, 5, 8, 10, 12, or 14) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 2, 4, 5, 8, 10, 12, or 14.

An immunogenic fragment of an influenza polypeptide includes at least 8, 10, 15, or consecutive amino acids, at least 21 amino acids, at least 23 amino acids, at least 25 amino acids, or at least 30 amino acids of an influenza polypeptide having a sequence as set forth in SEQ ID NO: 2, 4, 5, 8, 10, 12, or 14, or variants thereof. In another embodiment, a fragment of an influenza polypeptide includes a specific antigenic epitope found on a full-length influenza polypeptide.

In another aspect, the present invention provides a polynucleotide encoding an influenza polypeptide, such as a polynucleotide encoding a polypeptide having a sequence as set forth in SEQ ID NO: 2, 4, 5, 8, 10, 12, or 14. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 5, 8, 10, 12, or 14, or a conservative variant, an allelic variant, a homolog or an immunogenic fragment comprising at least eight or at east ten consecutive amino acids of one of these polypeptides, or a combination of these polypeptides.

In another aspect, the present invention provides a polynucleotide having a nucleotide sequence as set forth in SEQ ID NO: 1, 3, 7, 9, 11, or 13, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 1, 3, 7, 9, 11, or 13, or a variant thereof.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of an influenza polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. an influenza peptide, advantageously, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to preparations comprising vectors, such as expression vectors, e.g., therapeutic compositions. The preparations can comprise one or more vectors, e.g., expression vectors, such as in vivo expression vectors, comprising and expressing one or more influenza polypeptides, antigens, epitopes or immunogens. In one embodiment, the vector contains and expresses a polynucleotide that comprises, consists essentially of, or consists of a polynucleotide coding for (and advantageously expressing) an influenza antigen, epitope or immunogen, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of an influenza polypeptide, antigen, epitope or immunogen (e.g., hemagglutinin, neuraminidase, nucleoprotein) or a fragment thereof.

According to another embodiment, the vector or vectors in the preparation comprise, or consist essentially of, or consist of polynucleotide(s) encoding one or more proteins or fragment(s) thereof of an influenza polypeptide, antigen, epitope or immunogen, the vector or vectors expressing the polynucleotide(s). In another embodiment, the preparation comprises one, two, or more vectors comprising polynucleotides encoding and expressing, advantageously in vivo, an influenza polypeptide, antigen, fusion protein or an epitope thereof. The invention is also directed at mixtures of vectors that comprise polynucleotides encoding and expressing different influenza polypeptides, antigens, epitopes or immunogens, e.g., an influenza polypeptide, antigen, epitope or immunogen from different species such as, but not limited to, humans, horses, pigs, dogs, cats in addition to avian species including chicken, ducks, turkeys, quails and geese.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846,946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) in Genbank under the accession number HUMTPA14. In another specific, non-limiting example, the plasmid utilized as a vector for the insertion of a polynucleotide sequence can contain the signal peptide sequence of equine IGF1 from amino acid M(24) to amino acid A(48) in Genbank under the accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding an influenza antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig, the Super promoter (Ni, M. et al., Plant J. 7, 661-676, 1995). The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter has a viral, a plant, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Any of constitutive, regulatable, or stimulus-dependent promoters may be used. For example, constitutive promoters may include the mannopine synthase promoter from *Agrobacterium tumefaciens*. Alternatively, it may be advantageous to use heat shock gene promoters, drought-inducible gene promoters, pathogen-inducible gene promoters, wound-inducible gene promoters, and light/dark-inducible gene promoters. It may be useful to use promoters that are controlled by plant growth regulators, such as abscissic acid, auxins, cytokinins, and gibberellic acid. Promoters may also be chosen that give tissue-specific expression (e.g., root, leaf, and floral-specific promoters).

The plasmids may comprise other expression control elements. It is particularly advantageous to incorporate stabilizing sequence(s), e.g., intron sequence(s), for example, maize alcohol dehydrogenase intron (maize ADHI intron), the first intron of the hCMV-IE (PCT Application No. WO1989/01036), the intron II of the rabbit β-globin gene (van Ooyen et al., 1979). In another embodiment, the plasmids may comprise 3' UTR. The 3' UTR may be, but not limited to, *agrobacterium* nopaline synthase (Nos) 3' UTR.

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

In one embodiment, the recombinant influenza antigen is expressed in a transgenic duckweed plant. In another embodiment, the transgenic plant is a *Lemna* plant. In yet another embodiment, the transgenic plant is *Lemna minor*. In yet another embodiment, the recombinant influenza antigen may be expressed in the *Lemna minor* protein expression system, the Biolex's LEX system$^{SM}$. Details of the *Lemna minor* protein expression system may be found, for example, in U.S. Pat. Nos. 6,815,184; 7,022,309; 7,160,717; 7,176,024, 6,040,498, 7,161,064, and 7,326,38; the disclosures of which are incorporated by reference in their entireties. The influenza antigen in the embodiments may be any polypeptide disclosed herein, or a polypeptide encoded by any polynucleotide disclosed herein.

Methods for Expressing Antigenic Influenza Polypeptides in Duckweed

Thus, in some embodiments of the invention, influenza polypeptides, or fragments or variants thereof, are expressed in duckweed. These methods comprise the use of expression cassettes that are introduced into a duckweed plant using any suitable transformation method known in the art. Polynucleotides within these expression cassettes can be modified for enhanced expression of the antigenic influenza polypeptide, or fragment or variant thereof, in duckweed, as follows.

Cassettes for Duckweed Expression of Antigenic Influenza Polypeptides

Transgenic duckweed expressing an influenza polypeptide, or fragment or variant thereof, is obtained by transformation of duckweed with an expression cassette comprising a polynucleotide encoding the influenza polypeptide, or fragment or variant thereof. In this manner, a polynucleotide encoding the influenza polypeptide of interest, or fragment or variant thereof, is constructed within an expression cassette and introduced into a duckweed plant by any suitable transformation method known in the art.

In some embodiments, the duckweed plant that is transformed with an expression cassette comprising polynucleotide encoding the influenza polypeptide of interest, or fragment or variant thereof, has also been transformed with an expression cassette that provides for expression of another heterologous polypeptide of interest, for example, another influenza polypeptide, fragment, or variant thereof. The expression cassette providing for expression of another heterologous polypeptide of interest can be provided on the same polynucleotide (for example, on the same transformation vector) for introduction into a duckweed plant, or on a different polynucleotide (for example, on different transformation vectors) for introduction into the duckweed plant at the same time or at different times, by the same or by different methods of introduction, for example, by the same or different transformation methods.

The expression cassettes for use in transformation of duckweed comprise expression control elements that at least comprise a transcriptional initiation region (e.g., a promoter) operably linked to the polynucleotide of interest, i.e., a polynucleotide encoding an antigenic influenza polypeptide, fragment, or variant thereof "Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame. Such an expression cassette is provided with a plurality of restriction sites for insertion of the polynucleotide or polynucleotides of interest (e.g., one polynucleotide of interest, two polynucleotides of interest, etc.) to be under the transcriptional regulation of the promoter and other expression control elements. In particular embodiments of the invention, the polynucleotide to be transferred contains two or more expression cassettes, each of which contains at least one polynucleotide of interest.

By "expression control element" is intended a regulatory region of DNA, usually comprising a TATA box, capable of directing RNA polymerase II, or in some embodiments, RNA polymerase III, to initiate RNA synthesis at the appropriate transcription initiation site for a particular coding sequence. An expression control element may additionally comprise other recognition sequences generally positioned upstream or 5' to the TATA box, which influence (e.g., enhance) the transcription initiation rate. Furthermore, an expression control element may additionally comprise sequences generally positioned downstream or 3' to the TATA box, which influence (e.g., enhance) the transcription initiation rate.

The transcriptional initiation region (e.g., a promoter) may be native or homologous or foreign or heterologous to the duckweed host, or could be the natural sequence or a synthetic sequence. By foreign, it is intended that the transcriptional initiation region is not found in the wild-type duckweed host into which the transcriptional initiation region is introduced. By "functional promoter" is intended the promoter, when operably linked to a sequence encoding an antigenic influenza polypeptide of interest, or fragment or variant thereof, is capable of driving expression (i.e., transcription and translation) of the encoded polypeptide, fragment, or variant. The promoters can be selected based on the desired outcome. Thus the expression cassettes of the invention can comprise constitutive, inducible, tissue-preferred, or other promoters for expression in duckweed.

Any suitable promoter known in the art can be employed in the expression cassettes according to the present invention, including bacterial, yeast, fungal, insect, mammalian, and plant promoters. For example, plant promoters, including duckweed promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthorne et al. (1990) *Plant Mol. Biol.* 15:49). Other promoters from viruses that infect plants, preferably duckweed, are also suitable including, but not limited to, promoters isolated from Dasheen mosaic virus, *Chlorella* virus (e.g., the *Chlorella* virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Expression control elements, including promoters, can be chosen to give a desired level of regulation. For example, in some instances, it may be advantageous to use a promoter that confers constitutive expression (e.g, the mannopine synthase promoter from *Agrobacterium tumefaciens*). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid). As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646 to Gelvin et al.). In the present invention, the expression cassette can contain activating nucleotide sequences inserted upstream of the promoter sequence to enhance the expression of the antigenic influenza polypeptide of interest, or fragment or variant thereof. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955,646, herein incorporated by reference).

The expression cassette thus includes in the 5'-3' direction of transcription, an expression control element comprising a transcriptional and translational initiation region, a polynucleotide of encoding an antigenic influenza polypeptide of interest (or fragment or variant thereof), and a transcriptional and translational termination region functional in plants. Any suitable termination sequence known in the art may be used in accordance with the present invention. The termination region may be native with the transcriptional initiation region, may be native with the coding sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence.

Generally, the expression cassette will comprise a selectable marker gene for the selection of transformed duckweed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) *EMBO J.* 6:2513; DeBlock et al. (1989) *Plant Physiol.* 91:691; Fromm et al. (1990) *BioTechnology* 8:833; Gordon-Kamm et al. (1990) *Plant Cell* 2:603. For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) *CRC Critical Reviews in Plant Science* 4:1); cyanamide hydratase (Maier-Greiner et al. (1991) *Proc. Natl. Acad. Sci. USA* 88:4250); aspartate kinase; dihydrodipicolinate synthase (Perl et al. (1993) *BioTechnology* 11:715); bar gene (Toki et al. (1992) *Plant Physiol.* 100:1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761,373 to Anderson et al.; Haughn et al. (1988) *Mol. Gen. Genet.* 221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to: gentamycin (e.g., aacC1, Wohlleben et al. (1989) *Mol. Gen. Genet.* 217:202-208); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Bio.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Bio.* 15:127); bromoxynil (Stalker et al. (1988) *Science* 242:419); 2,4-D (Streber et al. (1989) *BioTechnology* 7:811); phosphinothricin (DeBlock et al. (1987) *EMBO J.* 6:2513); spectinomycin (Bretagne-Sagnard and Chupeau, *Transgenic Research* 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff (1992) *Mol. Microbiol.* 6:2419; Barkley et al. (1980) *The Operon* 177-220; Hu et al. (1987) *Cell* 48:555; Brown et al. (1987) *Cell* 49:603; Figge et al. (1988) *Cell* 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al. (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes is not meant to be limiting. Any selectable marker gene can be used in the present invention.

Modification of Nucleotide Sequences for Enhanced Expression in a Plant Host

Where the antigenic influenza polypeptide or fragment or variant thereof is expressed within duckweed, the expressed polynucleotide sequence encoding the influenza polypeptide or fragment or variant thereof can be modified to enhance its expression in duckweed. One such modification is the synthesis of the polynucleotide using plant-preferred codons, particularly duckweed-preferred codons. Methods are available in the art for synthesizing nucleotide sequences with plant-preferred codons. See, e.g., U.S. Pat. Nos. 5,380,831 and 5,436,391; EP 0 359 472; EP 0 385 962; WO 91/16432; Perlak et al. (1991) *Proc. Natl. Acad. Sci. USA* 15:3324; Iannacome et al. (1997) *Plant Mol. Biol.* 34:485; and Murray et al. (1989) *Nucleic Acids. Res.* 17:477, herein incorporated by reference. Synthesis can be accomplished using any method known to one of skill in the art. The preferred codons may be determined from the codons of highest frequency in the proteins expressed in duckweed. For example, the frequency of codon usage for *Lemna minor* is found in the following Table.

| Lemna minor [gbpln]: 4 CDS's (1597 codons) fields: [triplet] [frequency: per thousand] ([number]) | | | | | | | |
|---|---|---|---|---|---|---|---|
| UUU | 17.5(28) | UCU | 13.8(22) | UAU | 8.8(14) | UGU | 5.0(8) |
| UUC | 36.3(58) | UCC | 17.5(28) | UAC | 15.7(25) | UGC | 14.4(23) |
| UUA | 5.6(9) | UCA | 14.4(23) | UAA | 0.0(0) | UGA | 1.9(3) |
| UUG | 13.8(22) | UCG | 13.8(22) | UAG | 0.6(1) | UGG | 16.3(26) |
| CUU | 15.7(25) | CCU | 11.9(19) | CAU | 6.9(11) | CGU | 4.4(7) |
| CUC | 25.7(41) | CCC | 15.7(25) | CAC | 16.9(27) | CGC | 18.2(29) |
| CUA | 5.0(8) | CCA | 11.3(18) | CAA | 10.0(16) | CGA | 6.3(10) |
| CUG | 21.3(34) | CCG | 14.4(23) | CAG | 22.5(36) | CGG | 10.6(17) |
| AUU | 18.8(30) | ACU | 9.4(15) | AAU | 13.8(22) | AGU | 10.0(16) |
| AUC | 19.4(31) | ACC | 17.5(28) | AAC | 21.9(35) | AGC | 15.0(24) |
| AUA | 1.9(3) | ACA | 5.0 (8) | AAA | 15.7(25) | AGA | 20.7(33) |
| AUG | 20.7(33) | ACG | 10.0(16) | AAG | 35.7(57) | AGG | 17.5(28) |
| GUU | 15.0(24) | GCU | 25.0(40) | GAU | 20.0(32) | GGU | 8.1(13) |
| GUC | 25.0(40) | GCC | 22.5(36) | GAC | 26.3(42) | GGC | 21.9(35) |
| GUA | 6.3(10) | GCA | 14.4(23) | GAA | 26.3(42) | GGA | 16.9(27) |
| GUG | 30.7(49) | GCG | 18.2(29) | GAG | 40.1(64) | GGG | 18.2(29) |

For purposes of the present invention, "duckweed-preferred codons" refers to codons that have a frequency of codon usage in duckweed of greater than 17%. "*Lemna*-preferred codons" as used herein refers to codons that have a frequency of codon usage in the genus *Lemna* of greater than 17%. "*Lemna minor*-preferred codons" as used herein refers to codons that have a frequency of codon usage in *Lemna minor* of greater than 17% where the frequency of codon usage in *Lemna minor* is obtained from the Codon Usage Database (GenBank Release 160.0 (Jun. 15, 2007).

It is further recognized that all or any part of the polynucleotide encoding the antigenic influenza polypeptide of interest, or fragment or variant thereof, may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be duckweed-preferred codons. In one embodiment, between 90 and 96% of the codons are duckweed-preferred codons. The coding sequence of a polynucleotide sequence encoding an antigenic influenza polypeptide of interest, or fragment or variant thereof, may comprise codons used with a frequency of at least 17% in *Lemna gibba* or at least 17% in *Lemna minor*. In one embodiment, the influenza polypeptide is an HA polypeptide, for example, the HA polypeptide set forth in SEQ ID NO:2, and the expression cassette comprises an optimized coding sequence for this HA polypeptide, where the coding sequence comprises duckweed-preferred codons, for example, *Lemna minor*-preferred or *Lemna gibba*-preferred codons. In one such embodiment, the expression cassette comprises SEQ ID NO:1, which contains *Lemna minor*-preferred codons encoding the HA polypeptide set forth in SEQ ID NO:2.

Other modifications can also be made to the polynucleotide encoding the antigenic influenza polypeptide of interest, or fragment or variant thereof, to enhance its expression in duckweed. These modifications include, but are not limited to, elimination of sequences encoding spurious polyadenylation signals, exon-intron splice site signals, transposon-like repeats, and other such well characterized sequences that may be deleterious to gene expression. The G-C content of the sequence may be adjusted to levels average for duckweed, as calculated by reference to known genes expressed in this plant. When possible, the polynucleotide encoding the heterologous polypeptide of interest may be modified to avoid predicted hairpin secondary mRNA structures.

There are known differences between the optimal translation initiation context nucleotide sequences for translation initiation codons in animals and plants. "Translation initiation context nucleotide sequence" as used herein refers to the identity of the three nucleotides directly 5' of the translation initiation codon. "Translation initiation codon" refers to the codon that initiates the translation of the mRNA transcribed from the nucleotide sequence of interest. The composition of these translation initiation context nucleotide sequences can influence the efficiency of translation initiation. See, for example, Lukaszewicz et al. (2000) *Plant Science* 154:89-98; and Joshi et al. (1997); *Plant Mol. Biol.* 35:993-1001. In the present invention, the translation initiation context nucleotide sequence for the translation initiation codon of the polynucleotide encoding the antigenic influenza polypeptide of interest, or fragment or variant thereof, may be modified to enhance expression in duckweed. In one embodiment, the nucleotide sequence is modified such that the three nucleotides directly upstream of the translation initiation codon are "ACC." In a second embodiment, these nucleotides are "ACA."

Expression of an antigenic influenza polypeptide in duckweed can also be enhanced by the use of 5' leader sequences. Such leader sequences can act to enhance translation. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci. USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA,* 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthorne et al. (1990) *J. Plant. Mol. Biol.* 15:49-58); and maize chlorotic mottle virus leader (MCMV; Lommel et al. (1991) Virology 81:382). See also, Della-Cioppa et al. (1987) *Plant Physiology* 84:965. Leader sequence comprising plant intron sequence, including intron sequence from the maize alcohol dehydrogenase 1 (ADH1) gene, the castor bean catalase gene, or the *Arabidopsis* tryptophan pathway gene PAT1 has also been shown to increase translational efficiency in plants (Callis et al. (1987) *Genes Dev.* 1:1183-1200; Mascarenhas et al. (1990) *Plant Mol. Biol.* 15:913-920).

In some embodiments of the present invention, nucleotide sequence corresponding to nucleotides 1222-1775 of the maize alcohol dehydrogenase 1 gene (ADH1; GenBank Accession Number X04049) is inserted upstream of the polynucleotide encoding the antigenic influenza polypeptide of interest, or fragment or variant thereof, to enhance the efficiency of its translation. In another embodiment, the expression cassette contains the leader from the *Lemna gibba* ribulose-bis-phosphate carboxylase small subunit 5B gene (RbcS leader; see Buzby et al. (1990) *Plant Cell* 2:805-814).

It is recognized that any of the expression-enhancing nucleotide sequence modifications described above can be used in the present invention, including any single modification or any possible combination of modifications. The phrase "modified for enhanced expression" in duckweed, as used herein, refers to a polynucleotide sequence that contains any one or any combination of these modifications.

Signal Peptides.

The influenza polypeptide of interest can be normally or advantageously expressed as a secreted protein. Secreted proteins are usually translated from precursor polypeptides that include a "signal peptide" that interacts with a receptor protein on the membrane of the endoplasmic reticulum (ER) to direct the translocation of the growing polypeptide chain across the membrane and into the endoplasmic reticulum for secretion from the cell. This signal peptide is often cleaved from the precursor polypeptide to produce a "mature" polypeptide lacking the signal peptide. In an embodiment of the present invention, an influenza polypeptide, or fragment or variant thereof, is expressed in duckweed from a polynucleotide sequence that is operably linked with a nucleotide sequence encoding a signal peptide that directs secretion of the antigenic influenza polypeptide, or fragment or variant thereof, into the culture medium. Plant signal peptides that target protein translocation to the endoplasmic reticulum (for secretion outside of the cell) are known in the art. See, for example, U.S. Pat. No. 6,020,169. In the present invention, any plant signal peptide can be used to target the expressed polypeptide to the ER.

In some embodiments, the signal peptide is the *Arabidopsis thaliana* basic endochitinase signal peptide (amino acids 14-34 of NCBI Protein Accession No. BAA82823), the extensin signal peptide (Stiefel et al. (1990) *Plant Cell* 2:785-793), the rice α-amylase signal peptide (amino acids 1-31 of NCBI Protein Accession No. AAA33885; see also GenBank M24286). In another embodiment, the signal peptide corresponds to the signal peptide of a secreted duckweed protein.

Alternatively, a mammalian signal peptide can be used to target the recombinantly produced antigenic influenza polypeptide for secretion from duckweed. It has been demonstrated that plant cells recognize mammalian signal peptides that target the endoplasmic reticulum, and that these signal peptides can direct the secretion of polypeptides not only through the plasma membrane but also through the plant cell wall. See U.S. Pat. Nos. 5,202,422 and 5,639,947.

In one embodiment, the nucleotide sequence encoding the signal peptide is modified for enhanced expression in duckweed, utilizing any modification or combination of modifications disclosed above for the polynucleotide sequence of interest.

The secreted antigenic influenza polypeptide, or fragment or variant thereof, can be harvested from the culture medium by any conventional means known in the art, including, but not limited to, chromatography, electrophoresis, dialysis, solvent-solvent extraction, and the like. In so doing, partially or substantially purified antigenic influenza polypeptide, or fragment or variant thereof, can be obtained from the culture medium.

Transformed Duckweed Plants and Duckweed Nodule Cultures.

The present invention provides transformed duckweed plants expressing an influenza polypeptide of interest, or fragment or variant thereof. The term "duckweed" refers to members of the family Lemnaceae. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*); genus *Wolfiella* (*Wl. caudata, Wl. denticulata, Wl. gladiata, Wl. hyalina, Wl. lingulata, Wl. repunda, Wl. rotunda*, and *Wl. neotropica*) and genus *Landoltia* (*L. punctata*). Any other genera or species of Lemnaceae, if they exist, are also aspects of the present invention. *Lemna* species can be classified using the taxonomic scheme described by Landolt (1986) *Biosystematic Investigation on the Family of Duckweeds: The family of Lemnaceae—A Monograph Study* (Geobatanischen Institut ETH, Stiftung Rubel, Zurich).

As used herein, "plant" includes whole plants, plant organs (e.g., fronds (leaves), stems, roots, etc.), seeds, plant cells, and progeny of same. Parts of transgenic plants are to be understood within the scope of the invention to comprise, e.g., plant cells, plant protoplasts, plant cell tissue cultures from which plants can be regenerated, tissues, plant calli, embryos as well as flowers, ovules, stems, fruits, leaves, roots, root tips, nodules, and the like originating in transgenic plants or their progeny previously transformed with a polynucleotide of interest and therefore consisting at least in part of transgenic cells. As used herein, the term "plant cell" includes cells of seeds, embryos, ovules, meristematic regions, callus tissue, leaves, fronds, roots, nodules, shoots, anthers, and pollen.

As used herein, "duckweed nodule" means duckweed tissue comprising duckweed cells where at least about 50%, 55%, 60%, 65%, 70%, 75%, 80%, 85%, 90%, 95% or 100% of the cells are differentiated cells. As used herein, "differentiated cell," means a cell with at least one phenotypic characteristic (e.g., a distinctive cell morphology or the expression of a marker nucleic acid or protein) that distinguishes it from undifferentiated cells or from cells found in other tissue types. The differentiated cells of the duckweed nodule culture described herein form a tiled smooth surface of interconnected cells fused at their adjacent cell walls, with nodules that have begun to organize into frond primordium scattered throughout the tissue. The surface of the tissue of the nodule culture has epidermal cells connected to each other via plasmadesmata.

The growth habit of the duckweeds is ideal for culturing methods. The plant rapidly proliferates through vegetative budding of new fronds, in a macroscopic manner analogous to asexual propagation in yeast. This proliferation occurs by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20-24 hours (Landolt (1957) *Ber. Schweiz. Bot. Ges.* 67:271; Chang et al. (1977) *Bull. Inst. Chem. Acad. Sin.* 24:19; Datko and Mudd (1970) *Plant Physiol.* 65:16; Venkataraman et al. (1970) *Z. Pflanzenphysiol.* 62: 316). Intensive culture of duckweed results in the highest rates of biomass accumulation per unit time (Landolt and Kandeler (1987) *The Family of Lemnaceae—A Monographic Study Vol.* 2: *Phytochemistry, Physiology, Application, Bibliography* (Veroffentlichungen des Geobotanischen Institutes ETH, Stiftung Rubel, Zurich)), with dry weight accumulation ranging from 6-15% of fresh weight (Tillberg et al. (1979) *Physiol. Plant.* 46:5; Landolt (1957) *Ber. Schweiz. Bot. Ges.* 67:271; Stomp, unpublished data). Protein content of a number of duckweed species grown under varying conditions has been reported to range from 15-45% dry weight (Chang et al. (1977) *Bull. Inst. Chem. Acad. Sin.* 24:19; Chang and Chui (1978) *Z. Pflanzenphysiol.* 89:91; Porath et al. (1979) *Aquatic Botany* 7:272; Appenroth et al. (1982) *Biochem. Physiol. Pflanz.* 177:251). Using these values, the level of protein production per liter of medium in duckweed is on the same order of magnitude as yeast gene expression systems.

The transformed duckweed plants of the invention can be obtained by introducing an expression construct comprising a polynucleotide encoding an antigenic influenza polypeptide, or fragment or variant thereof, into the duckweed plant of interest.

The term "introducing" in the context of a polynucleotide, for example, an expression construct comprising a polynucleotide encoding an antigenic influenza polypeptide, or fragment or variant thereof, is intended to mean presenting to the duckweed plant the polynucleotide in such a manner that the polynucleotide gains access to the interior of a cell of the duckweed plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the duckweed host cell of interest in a single transformation event, in separate transformation events, or, for example, as part of a breeding protocol. The compositions and methods of the invention do not depend on a particular method for introducing one or more polynucleotides into a duckweed plant, only that the polynucleotide(s) gains access to the interior of at least one cell of the duckweed plant. Methods for introducing polynucleotides into plants are known in the art including, but not limited to, transient transformation methods, stable transformation methods, and virus-mediated methods.

"Transient transformation" in the context of a polynucleotide such as a polynucleotide encoding an antigenic influenza polypeptide, or fragment or variant thereof, is intended to mean that a polynucleotide is introduced into the duckweed plant and does not integrate into the genome of the duckweed plant.

By "stably introducing" or "stably introduced" in the context of a polynucleotide (such as a polynucleotide encoding an antigenic influenza polypeptide, or fragment or variant thereof) introduced into a duckweed plant is intended the introduced polynucleotide is stably incorporated into the duckweed genome, and thus the duckweed plant is stably transformed with the polynucleotide.

"Stable transformation" or "stably transformed" is intended to mean that a polynucleotide, for example, a polynucleotide encoding an antigenic influenza polypeptide, or fragment or variant thereof, introduced into a duckweed plant integrates into the genome of the plant and is capable of being inherited by the progeny thereof, more particularly, by the progeny of multiple successive generations. In some embodiments, successive generations include progeny produced vegetatively (i.e., asexual reproduction), for example, with clonal propagation. In other embodiments, successive generations include progeny produced via sexual reproduction.

An expression construct comprising a polynucleotide encoding an antigenic influenza polypeptide, or fragment or variant thereof, can be introduced into a duckweed plant of interest using any transformation protocol known to those of skill in art. Suitable methods of introducing nucleotide sequences into duckweed plants or plant cells or nodules include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,563,055 and 5,981,840, both of which are herein incorporated by reference), direct gene transfer (Paszkowski et al. (1984) *EMBO J.* 3:2717-2722), ballistic particle acceleration (see, e.g., U.S. Pat. Nos. 4,945,050; 5,879,918; 5,886,244; and 5,932,782 (each of which is herein incorporated by reference); and Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926). The cells that have been transformed may be grown into plants in accordance with conventional ways.

As noted above, stably transformed duckweed can be obtained by any gene transfer method known in the art, such as one of the gene transfer methods disclosed in U.S. Pat. No. 6,040,498 or U.S. Patent Application Publication Nos. 2003/0115640, 2003/0033630 or 2002/0088027; each of which is incorporated herein by reference as if set forth in its entirety. Duckweed plant or nodule cultures can be efficiently transformed with an expression cassette containing a nucleic acid sequence as described herein by any one of a number of methods including *Agrobacterium*-mediated gene transfer, ballistic bombardment or electroporation. The *Agrobacterium* used can be *Agrobacterium tumefaciens* or *Agrobacterium rhizogenes*. Stable duckweed transformants can be isolated by transforming the duckweed cells with both the nucleic acid sequence of interest and a gene that confers resistance to a selection agent, followed by culturing the transformed cells in a medium containing the selection agent. See, for example, U.S. Pat. No. 6,040,498, the contents of which are herein incorporated by reference in their entirety.

The stably transformed duckweed plants utilized in these methods should exhibit normal morphology and be fertile by sexual reproduction and/or able to reproduce vegetatively (i.e., asexual reproduction), for example, with clonal propogation. Preferably, transformed duckweed plants of the present invention contain a single copy of the transferred nucleic acid comprising a polynucleotide encoding an antigenic influenza polypeptide, or fragment or variant thereof, and the transferred nucleic acid has no notable rearrangements therein. It is recognized that the transformed duckweed plants of the invention may contain the transferred nucleic acid present in low copy numbers (i.e., no more than twelve copies, no more than eight copies, no more than five copies, alternatively, no more than three copies, as a further alternative, fewer than three copies of the nucleic acid per transformed cell).

Transformed plants expressing an antigenic influenza polypeptide, or fragment or variant thereof, can be cultured under suitable conditions for expressing the antigenic influenza polypeptide, or fragment or variant thereof. The antigenic influenza polypeptide, or fragment or variant thereof, can then be harvested from the duckweed plant, the culture medium, or the duckweed plant and the culture medium, and, where desired, purified using any conventional isolation and purification method known in the art, including chromatography, electrophoresis, dialysis, solvent-solvent extraction, and the like. The antigenic influenza polypeptide, or fragment or variant thereof, can then be formulated as a vaccine for therapeutic applications, as described elsewhere herein.

Methods of Preparing an Avian Influenza Polypeptide

As described fully herein, in an embodiment, a method of producing an antigenic avian influenza polypeptide comprises: (a) culturing within a duckweed culture medium a duckweed plant culture or a duckweed nodule culture, wherein the duckweed plant culture or duckweed nodule culture is stably transformed to express the antigenic polypeptide, and wherein the antigenic polypeptide is expressed from a nucleotide sequence comprising a coding sequence for said antigenic polypeptide and an operably linked coding sequence for a signal peptide that directs secretion of the antigenic polypeptide into the culture medium; and (b) collecting the antigenic polypeptide from said culture medium. The term collecting includes but is not limited to harvesting from the culture medium or purifying.

After production of the recombinant polypeptide in duckweed, any method available in the art may be used for protein purification. The various steps include freeing the protein from the nonprotein or plant material, followed by the purification of the protein of interest from other proteins. Initial steps in the purification process include centrifugation, filtration or a combination thereof. Proteins secreted within the extracellular space of tissues can be obtained using vacuum or centrifugal extraction. Minimal processing could also involve preparation of crude products. Other methods include maceration and extraction in order to permit the direct use of the extract.

Such methods to purify the protein of interest can exploit differences in protein size, physio-chemical properties, and binding affinity. Such methods include chromatography, including procainamide affinity, size exclusion, high pressure liquid, reversed-phase, and anion-exchange chromatography, affinity tags, filtration, etc. In particular, immobilized Ni-ion affinity chromatography can be used to purify the expressed protein. See, Favacho et al. (2006) Protein expression and purification 46:196-203. See also, Zhou et al. (2007) The Protein J 26:29-37; Wang et al. (2006) Vaccine 15:2176-2185; and WO/2009/076778; all of which are herein incorporated by reference. Protectants may be used in the purification process such as osmotica, antioxidants, phenolic oxidation inhibitors, protease inhibitors, and the like.

Methods of Use

In an embodiment, the subject matter disclosed herein is directed to a method of vaccinating an animal comprising administering to the animal an effective amount of a vaccine which may comprise an effective amount of a recombinant avian influenza antigen and a pharmaceutically or veterinarily acceptable carrier, excipient, or vehicle.

The vaccine or composition comprises a recombinant influenza polypeptide. The recombinant polypeptide may be produced in duckweed plant. The recombinant polypeptide may be partially or substantially purified. The recombinant polypeptide may be glycosylated.

In an embodiment, the subject matter disclosed herein is directed to a method of eliciting an immune response comprising administering to the avian a vaccine comprising an avian influenza antigen expressed, wherein an immune response is elicited.

In an embodiment, the subject matter disclosed herein is directed to a method of eliciting an immune response comprising administering to the avian a vaccine comprising an avian influenza antigen produced in duckweed and plant material from the duckweed, wherein an immune response is elicited.

In an embodiment, the subject matter disclosed herein is directed to a method of preparing a stably transformed plant or plant culture selected from the genus *Lemna* comprising, (a) introducing into the plant a genetic construct comprising an avian influenza antigen gene; and (b) cultivating the plant. Methods for transformation of duckweed are available in the art and set forth herein.

In an embodiment, the subject matter disclosed herein is directed to a method of preparing a vaccine or composition comprising isolating an avian influenza antigen produced by a *Lemna* expression system and optionally combining with a pharmaceutically or veterinarily acceptable carrier, excipient or vehicle.

In an embodiment, the subject matter disclosed herein is directed to a method of preparing a vaccine or composition comprising combining an avian influenza antigen produced by a *Lemna* expression system and plant material from the genus *Lemna* and optionally a pharmaceutically or veterinarily acceptable carrier, excipient, or vehicle.

In yet another embodiment, the vaccine or composition may be administered to a one-day-old or older chickens.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the boost. This administration protocol is called "prime-boost".

In the present invention a recombinant viral vector is used to express an influenza coding sequence or fragments thereof encoding an antigenic influenza polypeptide or fragment or variant thereof. Specifically, the viral vector can express an avian influenza sequence, more specifically an HA gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. Nos. 5,505,941, 5,494,8070), raccoonpox virus, swinepox virus, etc.], adenovirus (e.g., human adenovirus, canine adenovirus), herpesvirus (e.g. canine herpesvirus, herpesvirus of turkey, Marek's disease virus, infectious laryngotracheitis virus, feline herpesvirus, bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The influenza antigen, epitope or immunogen may be a hemagglutinin, such as H5. The fowlpox vector may be vFP89 or vFP2211. The canarypox vector may be vCP2241 (see, US 2008/0107681 and US 2008/0107687). The avian influenza antigen of the invention to be expressed is inserted under the control of a specific poxvirus promoter, e.g., the vaccinia promoter 7.5 kDa (Cochran et al., 1985), the vaccinia promoter 13L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

In another aspect of the prime-boost protocol or regime of the invention, a composition comprising an avian influenza antigen of the invention is administered followed by the administration of a recombinant viral vector that contains and expresses an avian influenza antigen and/or variants or fragments thereof in vivo. Likewise, a prime-boost protocol may comprise the administration of a recombinant viral vector followed by the administration of a recombinant avian influenza antigen of the invention. It is further noted that both the primary and the secondary administrations may comprise the recombinant avian influenza antigen of the invention. Thus, the recombinant avian influenza antigen of the invention may be administered in any order with a viral vector or alternatively may be used alone as both the primary and secondary compositions.

In yet another aspect of the prime-boost protocol of the invention, a composition comprising an avian influenza antigen of the invention is administered followed by the administration of an inactivated viral composition or vaccine comprising the avian influenza antigen. Likewise, a prime-boost protocol may comprise the administration of an inactivated viral composition or vaccine followed by the administration of a recombinant avian influenza antigen of the invention. It is further noted that both the primary and the secondary administrations may comprise the recombinant antigenic polypeptide of the invention. The antigenic polypeptides of the invention may be administered in any order with an inactivated viral composition or vaccine or alternatively may be used alone as both the primary and secondary compositions.

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

The dose volume of compositions for target species that are mammals, e.g., the dose volume of avian compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as avian, with a virulent strain of influenza, advantageously the influenza belonging to the H5 subtypes such as H5N1, H5N2, H5N8 or H5N9 strains. Both homologous and heterologous strains are used for challenge to test the efficacy of the vaccine. The animal may be challenged by spray, intranasally, intra-ocularly, intra-tracheally, and/or orally. The challenge viral may be about $10^{5-8}$ $EID_{50}$ in a volume depending upon the route of administration. For example, if the administration is by spray, a virus suspension is aerosolized to generate about 1 to 100 μm droplets, if the administration is intra-nasal, intra-tracheal or oral, the volume of the challenge virus is about 0.5 ml, 1-2 ml, and 5-10 ml, respectively. Animals may be observed daily for 14 days following challenge for clinical signs, for example, dehydration and pasty vents. In addition, the groups of animals may be euthanized and evaluated for pathological findings of pulmonary and pleural hemorrhage, tracheitis, bronchitis, bronchiolitis, and bronchopneumonia. Orophayngeal swabs may be collected from all animals post challenge for virus isolation. The presence or absence of viral antigens in respiratory tissues may be evaluated by quantitative real time reverse transcriptase polymerase chain reaction (qRRT-PCR). Blood samples may be collected before and post-challenge and may be analyzed for the presence of anti-influenza H5N1 virus-specific antibody.

The compositions comprising the recombinant antigenic polypeptides of the invention used in the prime-boost protocols are contained in a pharmaceutically or veterinary acceptable vehicle, diluent or excipient. The protocols of the invention protect the animal from avian influenza and/or prevent disease progression in an infected animal.

The various administrations are preferably carried out 1 to 6 weeks apart. According to one embodiment, an annual booster is also envisioned. The animals are at least one-day-old at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is an avian.

In one embodiment, the invention provides for the administration of a therapeutically effective amount of a formulation for the delivery and expression of an influenza antigen or epitope in a target cell. Determination of the therapeutically effective amount is routine experimentation for one of ordinary skill in the art. In one embodiment, the formulation comprises an expression vector comprising a polynucleotide that expresses an influenza antigen or epitope and a pharmaceutically or veterinarily acceptable carrier, vehicle or excipient. In another embodiment, the pharmaceutically or veterinarily acceptable carrier, vehicle or excipient facilitates transfection or infection and/or improves preservation of the vector or protein in a host.

In one embodiment, the subject matter disclosed herein provides a vaccination regime and detection method for differentiation between infected and vaccinated animals (DIVA). Currently, there are two types of avian influenza vaccines, inactivated whole AI virus (AIV) and live recombinant vaccines, based on fowlpox and Newcastle disease virus, where hemagglutinin (HA) has been proved to be the primary target for generating protective immunity [Peyre, et al., Epidemiol Infect, 2009. 137(1): p. 1-21; Bublot, et al., Ann N Y Acad Sci, 2006. 1081: p. 193-201; Skehel, et al., Annu Rev Biochem, 2000. 69: p. 531-69]. Conventional inactivated vaccine requires growing the AIV in embryonated eggs or in cell culture, which necessitates highly contained facility with potential hazard of affecting the environment and personnel. In addition, there is currently no commercially available DIVA test compatible with the use of inactivated vaccines [Bublot, et al., 2006; El Sahly, et al., Expert Rev Vaccines, 2008. 7(2): p. 241-7; Veits, et al., Vaccine, 2008. 26(13): p. 1688-96]. A strategy that allows "differentiation of infected from vaccinated animals" (DIVA), has been put forward as a possible solution for the eventual eradication of AI without involving mass culling of birds and the consequent economic damage, especially in developing countries (Food and Agriculture Organization of the United (FAO) (2004). FAO, OIE & WHO Technical consultation on the Control of Avian Influenza. Animal health special report). This strategy has the benefits of vaccination (less virus in the environment) with the ability to identify infected flocks which still allows the implementation of other control measures, including stamping out. At the flock level, a simple approach is to regularly monitor sentinel birds left unvaccinated in each vaccinated flock, but this may cause some management problems, particularly in identifying the sentinels in large flocks. As an alternative, testing for field exposure may be performed on the vaccinated birds. In order to achieve this, vaccination systems that enable the detection of field exposure in vaccinated populations should be used. Several systems have been developed in recent years, including the use of a vaccine containing a virus of the same H subtype but a different N from the field virus. Antibodies to the N of the field virus act as natural markers of infection, however, problems would arise if a field virus emerges that has a different N antigen to the existing field virus or if subtypes with different N antigens are already circulating in the field. Alternatively the use of vaccines that contains only HA would allow classical AGID and NP- or matrix-based ELISAs to be used to detect infection in vaccinated birds.

It is disclosed herein that the use of the vaccine or composition of the present invention allows the detection of influenza infection in a vaccinated animal using available diagnosis test aiming to detect antibody response against influenza proteins other than HA such as agar gel immunodiffusion or NP-based ELISA. It is disclosed herein that the use of the vaccine or composition of the present invention allows the detection of the infection in animals by differentiating between infected and vaccinated animals (DIVA). A method is disclosed herein for diagnosing the infection of influenza in an animal using NP-based immunogenic detection method, such as, NP-based ELISA. In one embodiment, the subject matter disclosed herein is directed to a method of diagnosing influenza infection in an animal, comprising: a) contacting a solid substrate comprising a nucleoprotein (NP) with a sample obtained from the animal; b) contacting the solid substrate with a monoclonal antibody (MAb) against the NP; and c) detecting binding of the MAb to the sample captured by the NP on the solid substrate, wherein the percentage inhibition of test sample relative to the negative control indicates that the subject is infected with influenza, thereby diagnosing influenza infection in the subject.

Article of Manufacture

In an embodiment, the subject matter disclosed herein is directed to a kit for performing a method of eliciting or inducing an immune response which may comprise any one of the recombinant influenza immunological compositions or vaccines, or inactivated influenza immunological compositions or vaccines, recombinant influenza viral compositions or vaccines, and instructions for performing the method.

Another embodiment of the invention is a kit for performing a method of inducing an immunological or protective response against influenza in an animal comprising a composition or vaccine comprising an avian influenza antigen of the invention and a recombinant influenza viral immunological composition or vaccine, and instructions for performing the method of delivery in an effective amount for eliciting an immune response in the animal.

Another embodiment of the invention is a kit for performing a method of inducing an immunological or protective response against influenza in an animal comprising a composition or vaccine comprising an avian influenza antigen of the invention and an inactivated influenza immunological composition or vaccine, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The following embodiments are encompassed by the invention. In an embodiment, a composition comprising an avian influenza antigen or fragment or variant thereof and a pharmaceutical or veterinarily acceptable carrier, excipient, or vehicle is disclosed. In another embodiment, the composition described above wherein the avian influenza antigen or fragment or variant thereof comprises an immunogenic fragment comprising at least 15 amino acids of an avian influenza antigen is disclosed. In yet another embodiment, the above compositions wherein the avian influenza antigen or fragment or variant thereof is produced in duckweed are disclosed. In an embodiment, the above compositions wherein the avian influenza antigen or fragment or variant thereof is partially purified are disclosed. In an embodiment, the above compositions wherein the avian influenza antigen or fragment or variant thereof is substantially purified are disclosed. In an embodiment, the above compositions wherein the avian influenza antigen or fragment or variant thereof is an avian H5N1 polypeptide are disclosed. In an embodiment, the above compositions wherein the H5N1 polypeptide is a hemagglutinin polypeptide are disclosed. In an embodiment, the above compositions wherein the avian influenza antigen or fragment or variant thereof has at least 80% sequence identity to the sequence as set forth in SEQ ID NO:2, 4, 5, 8, 10, 12, or 14 are disclosed. In one embodiment, the above compositions wherein the avian influenza antigen is encoded by a polynucleotide having at least 70% sequence identity to the sequence as set forth in SEQ ID NO: 1, 3, 6, 7, 9, 11, or 13 are disclosed. In an embodiment, the above compositions wherein the pharmaceutical or veterinarily acceptable carrier, excipient, or vehicle is a water-in-oil emulsion or water in-oil-in-water or an oil-in-water emulsion are disclosed. In another embodiment, a method of vaccinating an animal susceptible to avian influenza comprising administering the compositions above to the animal is disclosed. In an embodiment, a method of vaccinating an animal susceptible to avian influenza comprising a prime-boost regime is disclosed. In an embodiment, a substantially purified antigenic polypeptide expressed in duckweed, wherein the polypeptide comprises: an amino acid sequence having at least 80% sequence identity to a polypeptide having the sequence as set forth in SEQ ID NO: 2, 4, 5, 10, 12 or 14 is disclosed. In any embodiment the animal is preferably an avian, an equine, a canine, a feline or a porcine. In one embodiment, a method of diagnosing influenza infection in an animal is disclosed. In yet another embodiment, a kit for prime-boost vaccination comprising at least two vials, wherein a first vial containing the composition of the present invention, and a second vial containing a composition for the boost-vaccination comprising a composition comprising a recombinant rival vector or a composition comprising an inactivated viral composition is disclosed.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

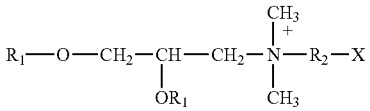

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and about 1:about 1 and about 1:about 2, e.g., 1:1 and 1:2.

The pharmaceutically or veterinarily acceptable carrier, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (Tween 80®), available from AppliChem, Inc., Cheshire, Conn.) and sorbitan esters (e.g., sorbitan monooleate (Span 80®), available from Sigma Aldrich, St. Louis, Mo.). In addition, with respect to a water-in-oil emulsion, see also U.S. Pat. No. 6,919,084, e.g., Example 8 thereof, incorporated herein by reference. In some embodiments, the antigen-containing aqueous phase comprises a saline solution comprising one or more buffering agents. An example of a suitable buffering solution is phosphate buffered saline. In an advantageous embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., 1960.

With regard to structure, the acrylic or methacrylic acid polymers and EMA are preferably formed by basic units having the following formula:

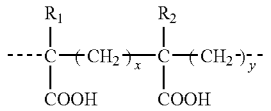

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, an avian cytokine for preparations to be administered to avian).

Examples of suitable emulsions or adjuvants are further described, for example, in U.S. Pat. Nos. 6,235,282; 6,224,882; 7,371,395; US 2006/0233831; US 2005/0238660; US 2006/0233831 (all Merial's patents and patent applications).

The immunological composition and/or vaccine according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

In the case of immunological composition and/or vaccine based on a plasmid vector, a dose can comprise, consist essentially of or consist of, in general terms, about in 1 μg to about 2000 μg, advantageously about 50 μg to about 1000 μg and more advantageously from about 100 μg to about 800 μg of plasmid expressing the influenza antigen, epitope or immunogen. When immunological composition and/or vaccine based on a plasmid vector is administered with electroporation the dose of plasmid is generally between about 0.1 μg and 1 mg, advantageously between about 1 μg and 100 μg, advantageously between about 2 μg and 50 μg. The dose volumes can be between about 0.1 and about 2 ml, advantageously between about 0.2 and about 1 ml.

Advantageously, when the antigen is hemagglutinin, the dosage is measured in hemagglutination units (HAUs) or in μg HA. In an advantageous embodiment, the dosage may be about 655 hemagglutination units (HAU), 0.2 μg HA/dose, about 6550 HAU, 2.3 μg HA/dose or about 65,500 HAU/dose. In certain embodiments, the dosage is about 26,200 HAU, 9.2 μg HA/dose. The volume may be about 0.1 ml to about 1.0 ml and preferably between 0.1 and 0.3 ml in one-day-old chickens and between 0.3 and 0.5 ml in older chickens.

The immunological composition and/or vaccine contains per dose from about $10^4$ to about $10^{11}$, advantageously from about $10^5$ to about $10^{10}$ and more advantageously from about $10^6$ to about $10^9$ viral particles of recombinant adenovirus expressing an influenza antigen, epitope or immunogen. In the case of immunological composition and/or vaccine based on a poxvirus, a dose can be between about $10^2$ pfu and about $10^9$ pfu. The immunological composition and/or vaccine contains per dose from about $10^5$ to $10^9$, advantageously from about $10^2$ to $10^8$ pfu of poxvirus or herpesvirus recombinant expressing the influenza antigen, epitope or immunogen.

The dose volume of compositions for target species that are mammals, e.g., the dose volume of avian compositions, based on viral vectors, e.g., non-poxvirus-viral-vector-based compositions, is generally between about 0.1 to about 2.0 ml, between about 0.1 to about 1.0 ml, and between about 0.1 ml to about 0.5 ml.

The invention will now be further described by way of the following non-limiting examples.

EXAMPLES

Construction of DNA inserts, plasmids and recombinant viral or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Construction of Plasmid and Transformation of Plants

In this study, a synthetic hemagglutinin (HA) gene from the highly pathogenic avian influenza (HPAI) H5N1 A/chicken/Indonesia/7/2003 (ck/Indonesia/03) isolate was expressed using Biolex's LEX System™, a proprietary *Lemna minor* protein expression system.

Hemagglutinin (HA) is a surface virus glycoprotein, responsible for attachment of virus to terminal sialic acids on host cell receptors and mediates fusions between viral particles and cell membranes through its own cleavage. It is a key antigen in the host response to influenza virus in both natural infection and vaccination.

The HA0 precursor is a protein containing 564 amino acids with an approximate molecular weight of 77 kDa, and with ability to agglutinate red blood cells. There are 6 predicted N-linked glycosylation sites in the HA1 region and 1 predicted N-linked glycosylation site in the HA2 region.

HA was highly expressed in the apoplast space of the plant, had the expected size by Western blot analysis, and had hemagglutination activity. Crude plant extract was prepared from transgenic *Lemna* line for evaluation of immunogenicity and efficacy in SPF chicken. Significant serum hemagglutination inhibition titer using both homologous and heterologous antigens indicated that *Lemna* derived HA was highly immunogenic. Three-week-old SPF chickens vaccinated with a single dose of *Lemna* derived HA formulated in a water-in-oil emulsion were challenged with either the A/ck/Indonesia/7/2003 or the antigenic variant A/ck/WestJava/PWT-WU/2006 HPAI H5N1 isolates. Full and 80 to 90% protection were induced against A/ck/Indonesia/07/2003 and A/ck/WestJava/PWT-WU/2006, respectively. A full clinical protection was obtained in HA-vaccinated birds primed at one-day-of-age with a fowlpox avian influenza vector vaccine (prime-boost scheme). Dramatic reduction in oropharyngeal shedding was observed for all vaccinates, and NP-based ELISA performed on sera samples clearly differentiated vaccinates and infected chickens. No protection was observed in chickens fed with grounded HA-expressing duckweed.

In conclusion, *Lemna minor* expressed HA elicited strong immune response and conferred excellent levels of protection against homologous and variant H5N1 challenge. Transgenic duckweed could be a great alternative to current inactivated vaccine with DIVA potential.

Construction of plant transformation plasmid An optimized version of the hemagglutinin (HA) gene from the highly pathogenic avian influenza (HPAI) virus A/chicken/Indonesia/7/2003 (H5N1) isolate was designed to have *L. minor* preferred codon usage (63-67% GC content). The synthetic HA gene was modified at the cleavage site between HA1 and HA2 from a highly pathogenic avian influenza sequence (multiple basic amino acids: RERRRKKR—SEQ ID NO:17) to a low pathogenic avian influenza sequence (RETR—SEQ ID NO:18). The native HA signal sequence was replaced by the rice α-amylase signal sequence (GenBank M24286) fused to the 5' end of the codon-optimized H5N1 coding sequence (SEQ ID NO:1). Restriction endonuclease sites (5'-EcoRI and 3'-SacI) were added for cloning into *Agrobacterium tumefaciens* binary vectors. The *L. minor* optimized HA gene was cloned EcoRI/SacI into a modified pMSP3 *A. tumefaciens* binary vector (Gasdaska, J., et al., Bioprocessing J. 3, 50-56, 2003) between the chimeric octopine and mannopine synthase promoter with *Lemna gibba* RBCS SSU1 5' leader and the Nopaline synthase (Nos) terminator resulting in the plant transformation vector MerB01.

Transgenic line generation and screening Using *A. tumefaciens* C58Z707 (Hepburn, A. G. et al., J. Gen. Microbiol. 131, 2961-2969, 1985) transformed with plant transformation vector MerB01, transgenic plants representing individual clonal lines were generated from rapidly growing *L. minor* nodules as described in Yamamoto, Y. et al., In Vitro Cell. Dev. Biol. 37, 349-353 (2001). For transgenic screening, individual clonal lines were preconditioned for 1 week at 150 to 200 mmol m-2s-1 in vented plant growth vessels containing SH medium (Schenk, R., et al., Can. J. Bot. 50, 199-204, 1972) without sucrose. Fifteen to twenty preconditioned fronds were then placed into vented containers containing fresh SH medium, and allowed to grow for two weeks. Tissue samples from each line were frozen and stored at −70° C. These tissue samples were subsequently screened for HA expression via a hemagglutination assay. In brief, frozen tissue was homogenized, centrifuged and the supernatant was removed for assay. Dilutions of the transgenic samples were incubated with a 10% solution of Turkey red blood cells (Fitzgerald Industries International) and scored for hemagglutination activity. The highest lines selected with this assay at initial dilutions were assayed again using larger dilutions to assess titer. Samples were compared to recombinant H5N1 as a positive control and a *Lemna* wild type control. An example of line screening is shown at FIG. 9.

Example 2

Development of an Avian Influenza H5N1 Line

One hundred and thirty transgenic Avian Influenza H5N1 lines were generated for screening. After the transgenic lines were generated, they were screened for expression of Avian Influenza H5N1 in the media and the tissue. In brief, the plants were grown for two weeks in small research vessels and the resulting media and tissue were collected for analysis. For the tissue analysis, frozen tissue was homogenized, centrifuged and the supernatant was removed for assay.

Samples were screened using a hemagglutination assay method. Briefly, dilutions of the transgenic samples were incubated with a 10% solution of Turkey red blood cells (Fitzgerald Industries International, Concord, Mass., USA) and scored for hemagglutination activity. The highest lines selected with this assay at initial dilutions were assayed again using larger dilutions. Samples were compared to recombinant H5N1 as a positive control and a *Lemna* wild type plant as a negative control. The analysis of culture media in the hemagglutination assay showed no activity on a subset of the lines, and the remainder of the lines were not tested in the assay. A representative plate from the hemagglutination assay and results of the hemagglutination analysis of the screening of the transgenic plants (in bar chart and table format) are depicted in FIG. 9. The highest lines from the initial screening were being scaled up to provide approximately 1 kg of biomass for further characterization.

Example 3

Production of Avian Influenza H5N1 Hemagglutinin in *Lemna minor*

Hemagglutination assay (HA), hemagglutination inhibition assay (HI), ELISA, SDS-PAGE, and Western Blot were used to characterize H5N1 HA. The recombinant protein was also screened against a panel of positive chicken sera by HI test.

Plant extraction Crude tissue extract from a line containing H5N1 HA was prepared according to the procedure described below. All steps were taken place at 4° C. One hundred grams of frozen biomass was mixed with 200 ml extraction buffer (50 mM $NaPO_4$, 0.3M NaCl, 10 mm EDTA, pH 7.4, protease inhibitor cocktail 1:1000 (Sigma P9599, Sigma, St. Louis, Mo., USA)) then homogenized in a Waring Blender with a 20 second burst for 4 times and 10-20 seconds cooling in between. The homogenate was centrifuged at 14,000×g for 30 min at 4° C., clarified by passing through a cheese cloth to remove any large debris and finally passing through cellulose acetate filter (0.22 um). The resulting homogenate was stored at 4° C. or on ice for immediate testing. The homogenate was frozen in aliquots at −80° C. for further analysis to avoid any freeze-thaw cycle. Total soluble protein (TSP) was determined using the Bradford assay with bovine serum albumin as a standard.

Hemagglutination assay (HA) The hemagglutination assay is a presumptive test to detect and quantitate hemagglutinating antigen. The basis of the HA test is that viral hemagglutinin will attach to receptors on the surface of red blood cells (RBCs) resulting in the agglutination of the RBCs. The HA assay was performed using serial dilution of 2-fold on the crude extract in Nunc U-Bottom Plates. Fifty μl of 10% Turkey Red Blood Cells (Fitzgerald Industries International Inc.) were incubated with 50 μl of test samples for 1 hr at room temperature and the titer was scored at the highest dilution before the defined button is observed. Negative controls included duckweed wild type and PBS, and positive controls included baculovirus expressed recombinant Avian Influenza Hemagglutinin A/Vietnam/1203/2004 (87 μg/ml).

Figure 10:
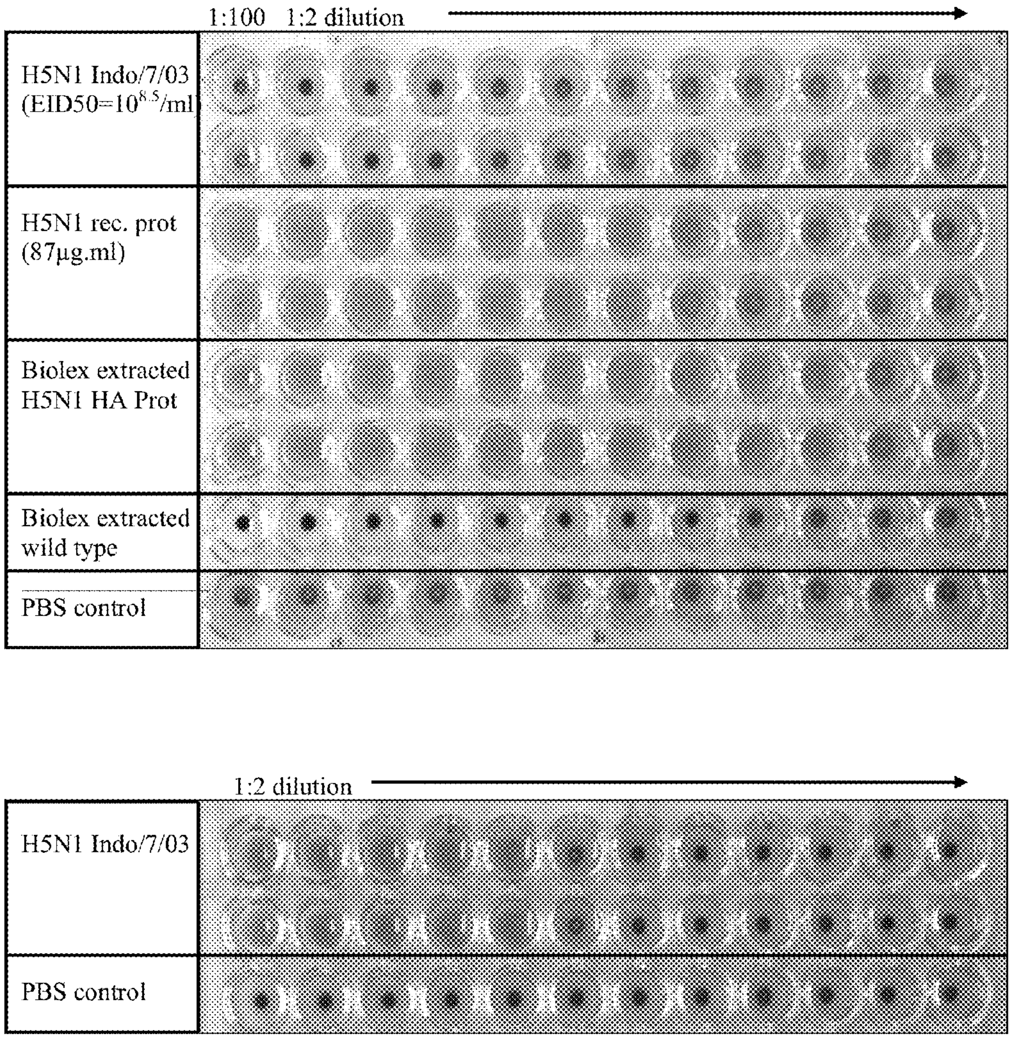
FIG. 10 provides the HA assay results of the transgenic plants expressing H5N1 HA.

A PBS negative control and Duckweed wild type sample did not cause hemagglutination, indicating that H5N1 HA is the sole source for the agglutination (FIG. 10). HA titer was determined to be 64, 12,800, and 51,200-102,400 for inactivated Avian Influenza H5N1 ck/Indonesia/03 (mutated), recombinant HA protein reference, and crude extract containing H5N1 HA, respectively. Results indicated even when diluted 102,400 fold, the crude extract was still capable of agglutinating RBCs and preventing them from forming a tight pellet. As judged by HA assay, the crude extract containing H5N1 HA is biologically active with significant higher activity than both inactivated whole virus at $10^{8.5}$ $EID_{50}$ and recombinant HA reference at 87 μg/ml.

Commercial turkey red blood cells were used for initial screening. To estimate formulation feasibility, the crude H5N1 HA extract was evaluated using a standardized HA assay. Fresh chicken red blood cells were washed 3 times with PBS, and incubated with testing samples for 30 min instead of 1 hr. The results indicated 1-2 fold difference in HA titer between standard HA assay and current HA assay. The estimated yield was determined as shown in FIG. 11.

Hemagglutination inhibition assay (HI) and ELISA The basis of hemagglutination inhibition assay is that the interaction of specific antibodies with homologous viral hemagglutinin will inhibit hemagglutination. The recognition of the expressed HA antigen by specific antibodies confirm the antigenicity of the HA.

Figure 12:
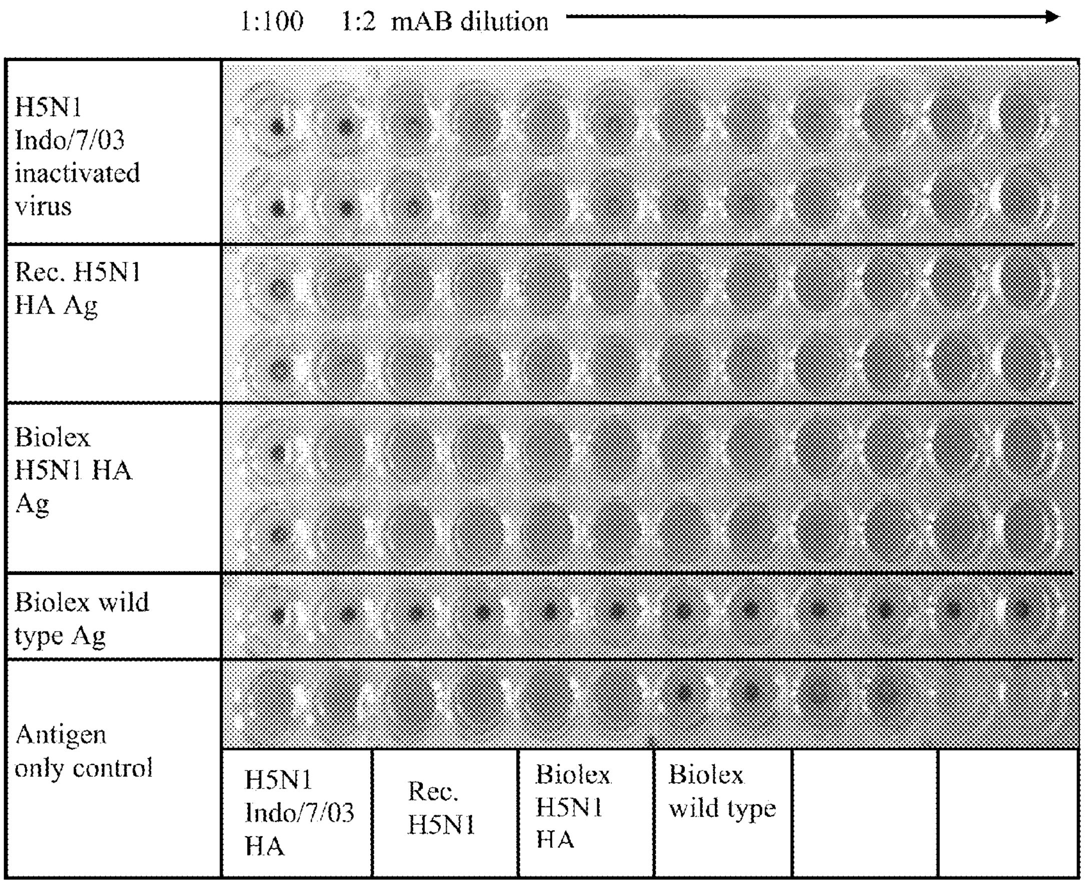
FIGS. 12-14 show the hemagglutination inhibition assay results performed with different antibodies.
Figure 13:
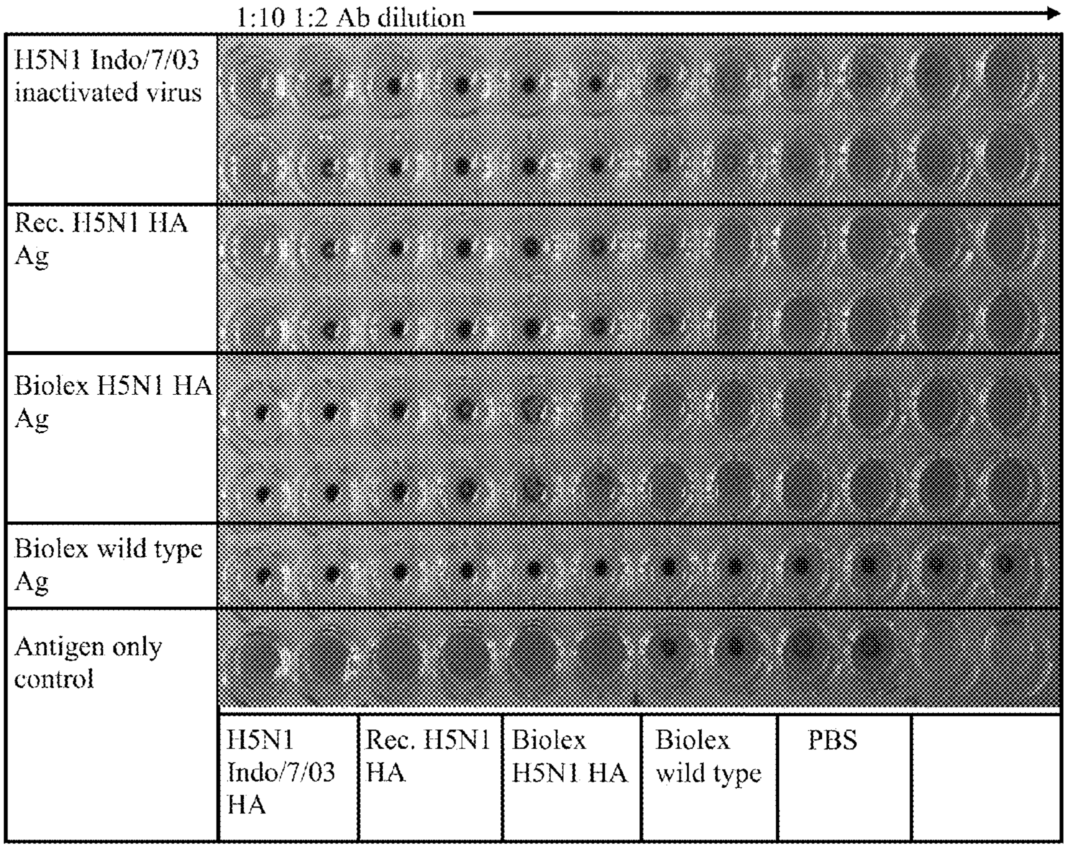
Figure 14:
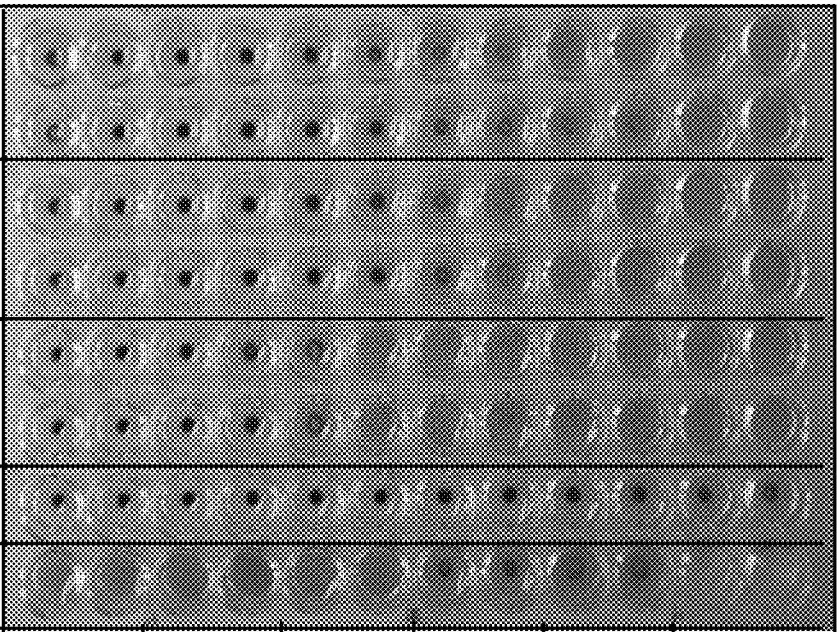

The agglutination activity of H5N1 HA crude extract was successfully neutralized by all HI positive sera, i.e. Monoclonal Anti-H5 Hemagglutinin of A/Vietnam/1203/04 Influenza Virus (Rockland, Gilbertsville, Pa.), Monoclonal Anti-H5N1 Ab pool of CP62 and 364/1 (CDC, Atlanta, Ga., USA), FP2211 chicken serum, and Avian Influenza H5N1 ck/Indonesia/03 (mutated) chicken serum. The negative controls included PBS and duckweed wild type sample which did not cause hemagglutination (FIGS. 12-14). The results confirmed that HA present in the crude H5N1 HA extract had the expected antigenicity.

For serological analysis of samples collected from clinical immunogenicity study, the HI test was performed according to NVSL standard protocol. A panel of antigens was tested for cross-reactivity of the serum: H5N1 clade 2.1 A/chicken/Indonesia/7/2003 (Indo/03), H5N1 clade 2.1 (variant) A/ck/West Java/PWT-WIJ/2006, H5N1 clade 2.2 A/WS/Mongolia/244/05, H5N1 clade 1 A/Vietnam/1203/2004 (VN/04), and H5N8 A/turkey/Ireland/1378/1983 (Ireland/83). Statistical analysis was performed using SAS V9.1. Blocking enzyme linked immunosorbent assay (bELISA) were performed according to the manufacturers instructions (FlockCheck AI MultiS-Screen Antibody Test Kit, IDEXX Laboratories, Westbrook, Me.).

SDS-PAGE and Western Blot Protein samples (crude tissue extracts) were diluted in SDS-PAGE sample buffer, separated on Nu-PAGE 10% Bis-Tris gel (Invitrogen, Carlsbad, Calif.) and transferred to PVDF membrane using Invitrogen iBlot. The membrane was blocked for 1 hr at room temperature (or overnight at 4° C.), probed with Monoclonal antibody against H5 Hemagglutinin of A/Vietnam/1203/04 Influenza Virus (Rockland) for 1 hr at room temperature. After four washes in PBS with 0.1% Tween-20, the membrane was incubated with a HRP-conjugated secondary antibody for 1 hr, washed 4 times in PBS with 0.05% Tween-20, and then developed for 5 min by TMB Membrane peroxidase substrate system (KPL, Gaithersburg, Md.). Image analysis was conducted using Odyssey LICOR infrared imaging system 9120 (LICOR, Lincoln, Nebr.).

Figure 16:
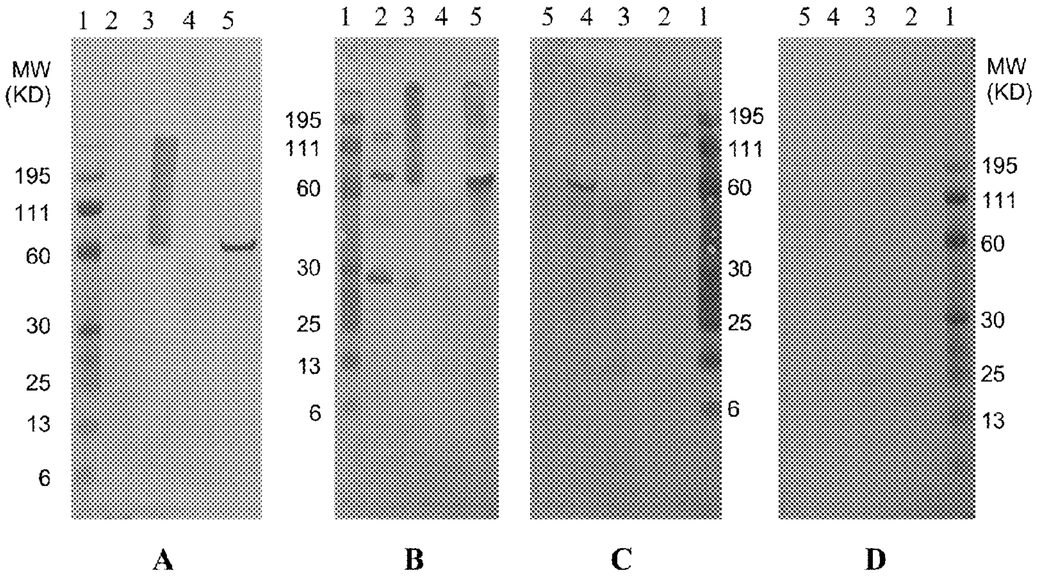
FIG. 16 provides the Western-blot using different sera. Panel A: 1° Ab—Mouse Monoclonal Anti-H5 Hemagglutinin of A/Vietnam/1203/04 Influenza Virus (VN04-10) (Rockland, lot 19012)—1:1000, 2° Ab—HRP-labeled Goat Anti-Mouse (Jackson, lot 75257)—1:2500; Panel B: 1° Ab—H5N1 (+) Chicken Serum—1:125, 2° Ab—HRP-labeled Goat Anti-Chicken (Jackson, lot 74240)—1:2500; Panel C: 1° Ab—FP2211 (Bird #878, Study 07-AI-05, SEPRL HI titer: 128)—1:125, 2° Ab—HRP-labeled Goat Anti-Chicken (Jackson, lot 74240)—1:2500; Panel D: 1° Ab—pAb anti-Avian Influenza A Hemagglutinin (Novus, lot 9F17207)—1:1000, 2° Ab—HRP-labeled Goat Anti-Rabbit (Jackson, lot 56811)—1:2500.

On the silver-stained SDS-PAGE, a distinguished band at 77 kDa was observed in HA expressing line (FIG. 15A). Western blot using Monoclonal Anti-H5 Hemagglutinin of A/Vietnam/1203/04 Influenza Virus confirmed expression of HA with expected molecular weight at 77 kDa, whereas the *Lemna* wild type remained negative (FIG. 15B). On a western blot, under non-reducing conditions, both Monoclonal Anti-H5 Hemagglutinin of A/Vietnam/1203/04 Influenza Virus (Rockland) and Monoclonal Anti-H5N1 Ab pool of CP62 and 364/1 (CDC, Atlanta, Ga.) recognized H5N1 HA as one predominant band with expected molecular weight at 77 kDa, whereas the *Lemna* wild type remained negative (FIG. 15C). FIG. 16 also demonstrated HA recognition by FP2211 chicken serum and Avian Influenza H5N1 ck/Indonesia/03 (mutated) chicken serum as one expected band at 77 kDa, whereas the Biolex wild type remained negative. Both inactivated whole virus and recombinant HA reference showed two bands at 50 kDa and 28 kDa indicating that HA0 was cleaved into two subunits HA1 and HA2. Western blot results were consistent with observations in the hemagglutination inhibition test.

Summary Hemagglutination assay results confirmed biological activity of H5N1 HA with titer of 51,200 HAU/50 μl, which was considerably higher than both purified recombinant HA at 87 μg/ml and inactivated Avian Influenza H5N1 ck/Indonesia/03 (mutated) at 108.5 EID50. The hemagglutination activity of H5N1 HA was successfully neutralized by a panel of HI positive sera, i.e. Monoclonal Anti-H5 Hemagglutinin of A/Vietnam/1203/04 Influenza Virus (Rockland), Monoclonal Anti-H5N1 Ab pool of CP62 and 364/1 (CDC), FP2211 chicken serum, and Avian Influenza H5N1 ck/Indonesia/03 chicken serum. The results suggested that each antibody recognized the antigens in their native form. HA expression was further verified by SDS-PAGE and western blot. A band of 77 kDa corresponding to the expected size of the HA0 precursor was visualized on silver-stained SDS-PAGE. On western blots, H5N1 HA was very well recognized with expected molecular weight at 77 kDa by all tested MAb and chicken serums, i.e. Monoclonal Anti-H5 Hemagglutinin of A/Vietnam/1203/04 Influenza Virus (Rockland), Monoclonal Anti-H5N1 Ab pool of CP62 and 364/1 (CDC), FP2211 chicken serum, and Avian Influenza H5N1 ck/Indonesia/03 chicken serum.

Example 4

Characterization of the Expression of HA from AIV H5N1 Strain Indonesia Produced by *Lemna* (Biolex System) by Immunolocalization in Planta The expression of HA in *Lemna* tissue was analyzed by immunofluorescence assay. A plant was fixed on a slide in MTSB buffer (EGTA 5 mM, Pipes 50 mM, MgSO4 5 mM, pH7.0) with 4% formaldehyde under vacuum, then rinsed with MTSB+0.1% Triton X100 and followed with water+0.1% Triton X100. Cell wall was digested using Driselase (Sigma-Aldrich, St. Louis, Mo.) for 30 minutes at 37° C., washed again with MTSB+0.1% Triton X100, MTSB+10% DMSO+3% NP40, and MTSB+0.1% Triton X100, then blocked with MTSB+3% BSA. The treated plant was then incubated with monoclonal antibody against H5 hemagglutinin of A/Vietnam/1203/04 Influenza Virus for over night at 4° C., and probed with Fluorescein (FITC)-conjugated secondary antibody for 3 hr at room temperature, the slides was examined using Nikkon eclipse 600 fluorescence microscopy.

Figure 17:
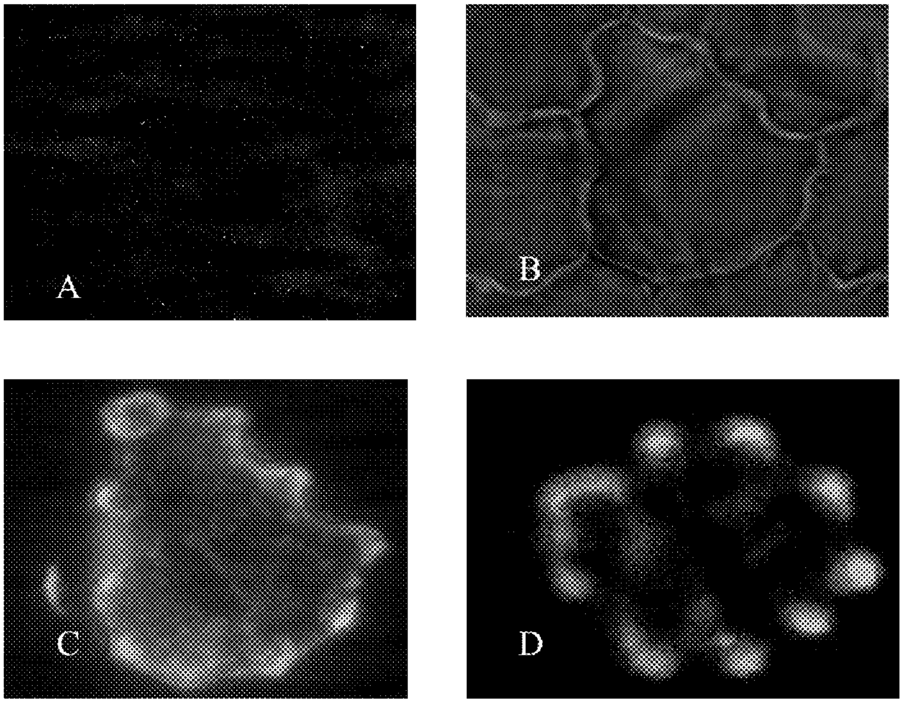
FIG. 17 depicts immunolocalization assay of *Lemna* expressed HA using monoclonal antibody against H5 Hemagglutinin of A/Vietnam/1203/04 Influenza Virus. (A) *Lemna* wild type as negative control under fluorescence microscopy. (B) *Lemna* plant expressing HA under light microscopy. (C, D) *Lemna* plant expressing HA under fluorescence microscopy.

Results indicated that there was no fluorescence background observed in *Lemna* wild type, whereas strong and specific fluorescence signal detected in transformed *Lemna* (FIG. 17). It also suggested that HA was expressed in apoplast of the plant tissue which was consistent with the target cellular location for HA expression.

Example 5

Immunogenicity and Challenge Studies

Immunogenicity and challenge studies were conducted in specific pathogen free (SPF) chickens vaccinated at three-week of age with adjuvanted *Lemna* expressed HA. Ten chickens were assigned to each vaccine group. A Group vaccinated with adjuvanted *Lemna* wild type material was included as a negative control group for both studies, and a group of adjuvanted experimental recombinant HA expressed in baculovirus system was also included for challenge study. One group (group 8) received a fowlpox vector AIV H5 (vFP89, see, US 2008/0107681 and US 2008/0107687) vaccine at one-day-of-age 3 weeks before the adjuvanted *Lemna* expressed HA (see below).

Immunogenicity study Chickens were vaccinated as described in FIG. 18. Six groups of 3-weeks-old chickens were tested using two different schemes: one shot (groups 5-7) or two shots (groups 2-4) at three dosage levels (655 HAU, 6550 HAU, and 26200 HAU). Prime-boost scheme (group 8) was investigated in one-day-old chickens primed with TROVAC® (vFP89) expressing HA gene of a H5N8 (A/turkey/Ireland/1378/83) and boosted with *Lemna* expressed HA at 6550 HAU. TROVAC® was administered subcutaneously in the nape of the neck ($10^3$ $TCID_{50}$/0.2 ml/dose). The water-in-oil emulsions of the crude *Lemna* extract was given by the intramuscular route in the leg (0.3 ml/dose). Blood sample was collected on days 21 and 35 for hemagglutination inhibition test.

None of the chickens showed adverse reaction to plant derived vaccines. The immunogenicity was determined by HI titer of sera collected from vaccinated chickens (FIG. 20). Chickens vaccinated with *Lemna* wild type were negative by the HI assay against all tested H5 antigens. Twenty one days after immunization, specific antibodies were induced in *Lemna* HA groups, the mean HI titers against homologous Indo/03 strains reached 4, 6.5, and 8.1 log 2 at 655 HAU, 6550HAU, and 262000 HAU dosage level, respectively. On day 35 post vaccination (p.v.) HI titers against Indo/03 remained at 4.7, 6.6, and 7.6 log 2 for low to high dose with one shot scheme, while the HI titers increased significantly to 6.8, 9.4 and 9.5 log 2 for two shots scheme, indicating clear boost effect ($p<0.005$) and dose effect ($p<0.005$ between low and medium/high dose). This result was further evidenced in HI titer against heterologous strains Mong/244/05 and VN/1203/04 at 2.9, 5.4, 6.5 log 2 vs. 5.3, 7.7, 8.5 log 2 and 2.6, 3.6, 4.8 vs. 4.2, 6.0, 6.6 log 2 for one shot and two shots scheme at 655 HAU, 6550HAU, and 262000 HAU dosage level, respectively. Immune response was the highest against homologous H5N1 clade 2.1 Indo/03 strain, followed by clade 2.2 Mong/244/05, then clade 1 VN/1203/04 for both vaccination schemes. A prime boost scheme, using a fowlpox recombinant expressing HA as prime, was also investigated with *Lemna* HA at intermediate dose of 6550 HAU. On day 21 after priming, no HI titers were observed for any H5 antigens except TK/Ire/83 with titer of 4.0 log 2. On day 35 after boost, HI titer increased to 5.3, 5.6, 5.4 and 9.2 log 2 against VN/1203/04, Indo/03, Mong/244/05, and Tk/Ire/83, respectively. However, when compared to *Lemna* HA two shot scheme at titers of 6.0, 9.4, 7.7, and 7.3 log 2, antibody response was low except for Tk/Ire/83.

Challenge study Chickens were vaccinated according to FIG. 19. Similar to the immunogenicity study, chickens were vaccinated with *Lemna* HA at three different doses, however by single immunization (groups 2-3, 5-7), with the exception of group 4 (oral vaccination) and group 8 (prime-boost scheme).

On Day 42, chickens were challenged intranasally/orally with HPAI H5N1 virus, A/ck/Indonesia/07/2003 (groups 1-4) or A/ck/WestJava/PWT-WU/2006 (groups 5-8) at $10^{6.0}$ $EID_{50}$ per chicken. After challenge, the chickens were observed daily for morbidity and mortality, and the morbid chickens were counted as infected with influenza. Oropharyngeal swabs to determine challenge virus shedding from respiratory tract were collected at 2 and 4 days post-challenge (DPC) in 1.5 ml of brain heart infusion (BHI) medium (Becton-Dickinson, Sparks, Md.) containing antimicrobial compounds (100 μg/mL gentamicin, 100 units/mL penicillin, and 5 μg/mL amphotericin B). Remaining chickens from all groups were bled for serum collection at days 42 and 56 of age. The birds were euthanized with intravenous sodium pentobarbital (100 mg/kg body weight) at 56 days of age.

It was expected that a challenge with a HPAI H5N1 virus would reproducibly induce 100% mortality of naïve chickens within 2 days. For both negative control groups, chickens vaccinated with *Lemna* wild type and challenged with Indo/03 strain, and chickens vaccinated with experimental recombinant HA control and challenged with PWT/06, died within this period (FIG. 19). In groups challenged with Indo/03, chickens vaccinated with *Lemna* derived HA via IM route survived 100% at both 655 HAU and 6550 HAU dosage levels. In groups challenged with PWT/06, nine and eight out of ten chickens survived after one shot scheme at 6550 HAU and 26200 HAU, respectively. One bird was euthanized at day 10 post challenge (dpc) due to severe torticollis in 6550 HAU group. TROVAC®/*Lemna* prime-boost scheme demonstrated 100% protection against this variant strain.

Viral shedding was investigated using quantitative RT-PCR test on oropharynx swabs samples taken from survivor birds at 2 and 4 dpc. Oropharyngeal swabs were tested by quantitative real time reverse transcriptase polymerase chain reaction (qRRT-PCR) for avian influenza virus, and qRRT-PCR cycle threshold values were converted to equivalent infectious titers in embryonating chicken eggs based on regression line produced using a challenge virus dilutional series (Lee et al., Journal of Virological Methods 119(2):151-158). Briefly, RNA was extracted from oropharyngeal swab material by adding 250 μl of swab medium to 750 μl of Trizol LS (Invitrogen Inc., Carlsbad, Calif.), followed by mixing via vortexing, incubation at room temperature for 10 min, and then 200 μl of chloroform was added. The samples were vortexed again, incubated at room temperature for 10 min, and then centrifuged for 15 min at approximately 12,000×g. The aqueous phase was collected and RNA isolated with the MagMAX AI/ND viral RNA isolation kit (Ambion, Inc. Austin Tex.) in accordance with the kit instructions using the KingFisher magnetic particle processing system (Thermo Scientific, Waltham, Mass.). The avian influenza virus challenge strains were used to produce the RNA for the quantitative standard. Allantoic fluid virus stocks were diluted in BHI broth (Becton-Dickinson) and titrated in embryonating chicken eggs at the time of dilution as per standard methods (Swayne et al., 2008, Avian influenza. In: Isolation and Identification of Avian Pathogens. 5th ed., pp. 128-134). Whole virus RNA was extracted from ten-fold dilutions of titrated virus as described for swab material. qRRT-PCR for the influenza matrix gene was performed as previously described (Lee et al., 2004). Virus titers in samples were calculated based on the standard curves, either calculated by the Smart Cycler II (Cepheid, Inc. Sunnyvale, Calif.) software or extrapolation of the standard curve equation. For the groups challenged with Indo/03, all chickens vaccinated with *Lemna* wild type were found positive at viral titer of $10^{6.9}$ $EID_{50}$, whereas viral shedding for *Lemna* HA groups reduced dramatically to just above detection limit of $10^{2.9}$ and $10^{3.1}$ $EID_{50}$ for 6550 HAU and 655 HAU, respectively, on 2 dpc, and became non-detectable on 4 dpc. For the groups challenged with antigenic variant PWT/06 strain, all chickens immunized with experimental HA at 5000 HAU still shed virus at $10^{7.1}$ $EID_{50}$ on 2 dpc, only one, two and one out of ten birds were detectable for 6550 HAU, 26200 HAU, and TROVAC/Lemna groups, respectively, with 2 still positive for *Lemna* HA groups at both 6550 and 26200 HAU after 4 dpc, however, virus was near or below the detection limit ($10^{3.5}$ $EID_{50}$) in TROVAC®/*Lemna* group.

Samples were also investigated for presence of nucleoprotein (NP) specific antibodies before and after H5N1 challenge using ELISA kit (FIG. 19). NP specific antibodies were absent from all sera samples collected after immunization with *Lemna* HA and before challenge. After PWT/06 challenge, 9 out1 of 9, 8 out of 8, and 8 out of 10 samples demonstrated positive signal for 6550 HAU, 26200 HAU, and prime-boost groups, respectively.

FIG. 21 showed serological analysis of samples collected before challenge on day 42 and post challenge on day 56 (14 dpc). Neither *Lemna* wild type nor oral group developed any humoral immunity to Indo/03 strain, three out of ten vaccinated with experimental baculovirus expressed HA showed detectable antibody titer of 2.4 log 2 against VN/04 strain. All other groups indicated positive immune responses to tested antigens, i.e. Indo/03, VN/04, and Mong/05, which supported the data in immunogenicity study.

After Indo/03 challenge, mean HI titer against Indo/03 increased from 4.5 to 7.1 log 2, and 6.9 to 8.2 log 2 for 655 HAU and 6550 HAU groups, respectively. The sera also indicated noticeable increase against PWT/06 from non-detectable to 2.7 log 2, and 2.2 to 3.8 log 2. After PWT/06 challenge, mean HI titer against homologous PWT/06, jumped from 2.2 to 6.0 log 2, 2.2 to 6.3 log 2, and 2.7 to 4.9 log 2 for 6550 HAU, 26200 HAU, and prime-boost groups, respectively. Similar trend was observed in HI titer against Indo/03 as well, from 6.9 to 8.6 log 2, 6.8 to 9.0 log 2, and 7.1 to 7.7 log 2 for the same groups.

Interestingly, the NP-based ELISA results indicated, as expected, that there was no detectable NP-immune response before the challenge. However, after the challenge, most serums of protected birds became positive. This result indicates clearly that either the *Lemna*-expressed HA vaccine alone or the prime-boost vaccination regimen with a fowlpox vector expressing HA (the so-called prime-boost scheme) is fully compatible with the DIVA (differentiating infected from vaccinated animals) strategy. The use of such vaccine should easily allow the detection of infection in a vaccinated flock by checking for anti-NP antibodies using commercially available ELISA.

Example 6

Purification of Avian Influenza Protein from Duckweed Plant

An avian influenza antigenic polypeptide or fragment or variant thereof is purified by separating the antigenic polypeptide from the culture medium. Initial purification includes centrifugation to remove plant material and cellular debris. Following this partial purification, the crude extract can be clarified by a pH shift and heat treatment followed by filtration on diatomaceous earth. The recombinant HA is purified from these clarified extracts by affinity chromatography on a fetuin column. Purification can be determined by densitometry on the Coomassie Blue stained SDS-PAGE gel.

Plant tissue is homogenized with 50 mM sodium phosphate, 0.3 M sodium chloride and 10 mM EDTA, pH 7.2 using a Silverson high shear mixer. The homogenate is acidified to pH 4.5 with 1 M citric acid, and centrifuged at 7,500 g for 30 min at 4° C. The pH of the supernatant is adjusted to pH 7.2 with 2 M 2-amino-2-[hydroxymethyl]-1,3-propanediol (Tris), before filtration using 0.22-μm filters. The material is loaded directly on mAbSelect SuRe protein A resin (GE Healthcare) equilibrated with a solution containing 50 mM sodium phosphate, 0.3 M sodium chloride and 10 mM EDTA, pH 7.2. After loading, the column is washed to baseline with the equilibration buffer followed by an intermediate wash with five column volumes of 0.1 M sodium acetate, pH 5.0. Bound antibody is eluted with ten column volumes of 0.1 M sodium acetate, pH 3.0. The protein A eluate is immediately neutralized with 2 M Tris. For aggregate removal, the protein A eluate is adjusted to pH 5.5 and applied to a ceramic hydroxyapatite type I (Bio-Rad, CA, USA) column equilibrated with 25 mM sodium phosphate, pH 5.5. After washing the column with five column volumes of equilibration buffer, the protein is eluted in a single step-elution using 0.25 M sodium phosphate, pH 5.5. Fractions containing the protein monitored by $A_{280}$ are pooled and stored at −80° C. (Cox, K. M., et al., 2006. 24(12): p. 1591-7)

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A composition comprising an avian influenza antigen consisting of the sequence as set forth in SEQ ID NO:2 and a pharmaceutically or veterinarily acceptable carrier, excipient, adjuvant, or vehicle.

2. A substantially purified avian influenza antigen expressed in duckweed, wherein the polypeptide consists of an amino acid sequence as set forth in SEQ ID NO:2.

3. The composition of claim 1, wherein the avian influenza antigen comprises a mutated HA cleavage region having the sequence as set forth in SEQ ID NO:18.

4. A composition comprising an avian influenza antigen of claim 2.

5. The composition of claim 4, wherein the avian influenza antigen is partially purified.

6. The composition of claim 4, wherein the avian influenza antigen is substantially purified.

7. The composition of claim 4, wherein the avian influenza antigen is an avian H5N1 polypeptide.

8. The composition of claim 7, wherein the H5N1 polypeptide is a hemagglutinin polypeptide.

9. The composition of claim 1 or 4, wherein the avian influenza antigen is encoded by a polynucleotide consisting of the sequence as set forth in SEQ ID NO:1.

10. The composition of claim 1 or 4, wherein the pharmaceutically or veterinarily acceptable carrier, excipient, adjuvant, or vehicle is a water-in-oil emulsion or an oil-in-water emulsion.

11. A method of vaccinating an animal susceptible to avian influenza comprising at least one administration of the composition according to claim 1.

12. The method of claim 11, wherein the method comprises a prime-boost administration regimen.

13. The method of claim 12, wherein the prime-boost regimen comprises a prime-administration of a composition according to claim 1.

14. The method of claim 12, wherein the prime-boost regimen comprises a boost administration of a composition according to claim 1.

15. The method of claim 12, wherein the prime-boost regimen comprises a prime-administration of a composition according to claim 1, and a boost administration of an inactivated viral composition or vaccine comprising the avian influenza antigen.

16. The method of claim 12, wherein the prime-boost regimen comprises a prime-administration of an inactivated viral composition or vaccine comprising the avian influenza antigen and a boost administration of a composition according to claim 1.

17. The method of claim 11, wherein the animal is avian, equine, canine, feline or porcine.

18. A kit for prime-boost vaccination comprising at least two vials, wherein a first vial contains the composition according to claim 1, and a second vial contains a composition for the boost-vaccination comprising a composition comprising a recombinant viral vector or a composition comprising an inactivated viral composition.

19. A synthetic DNA fragment consisting of the sequence as set forth in SEQ ID NO:1.

20. A plasmid comprising a DNA fragment of claim 19, wherein the DNA fragment is operably linked to a polynucleotide encoding a signal peptide.

21. The plasmid of claim 20, wherein the plasmid is for plant transformation.

22. The composition of claim 4, wherein the avian influenza antigen comprises a mutated HA cleavage region having the sequence as set forth in SEQ ID NO:18.

23. The composition of claim 10, wherein the pharmaceutically or veterinarily acceptable carrier, excipient, adjuvant, or vehicle is a water-in-oil emulsion.

24. The composition of claim 1 or 4, wherein the composition is administered at least once to an animal.

25. The composition of claim 24, wherein the composition is administered to the animal via a prime-boost regimen.

26. The composition of claim 1 or 4, wherein the composition provides a method for differentiation between infected and vaccinated animals (DIVA) when administered to an animal.

* * * * *